(12) United States Patent
Maharbiz et al.

(10) Patent No.: US 12,339,300 B2
(45) Date of Patent: Jun. 24, 2025

(54) THIN-FILM OPTICAL VOLTAGE SENSOR FOR VOLTAGE SENSING

(71) Applicants: THE REGENTS OF THE UNIVERSITY OF CALIFORNIA, Oakland, CA (US); CHAN ZUCKERBERG BIOHUB, INC., San Francisco, CA (US)

(72) Inventors: Michel M. Maharbiz, El Cerrito, CA (US); Jordan Edmunds, Oakland, CA (US); Soner Sonmezoglu, Oakland, CA (US)

(73) Assignees: THE REGENTS OF THE UNIVERSITY OF CALIFORNIA, Oakland, CA (US); CHAN ZUCKERBERG BIOHUB, INC., San Francisco, CA (US)

( * ) Notice: Subject to any disclaimer, the term of this patent is extended or adjusted under 35 U.S.C. 154(b) by 194 days.

(21) Appl. No.: 17/893,068

(22) Filed: Aug. 22, 2022

(65) Prior Publication Data
US 2023/0080274 A1   Mar. 16, 2023

Related U.S. Application Data

(60) Provisional application No. 63/240,704, filed on Sep. 3, 2021.

(51) Int. Cl.
*G01R 15/24* (2006.01)
*H10N 30/30* (2023.01)

(52) U.S. Cl.
CPC ......... *G01R 15/242* (2013.01); *G01R 15/247* (2013.01); *H10N 30/302* (2023.02)

(58) Field of Classification Search
CPC ................ G01R 15/242; G01R 15/247; G01R 15/241–26; G01R 15/144;
(Continued)

(56) References Cited

U.S. PATENT DOCUMENTS 4,595,876 A * 6/1986 Kuhara ................. G02F 1/0322
324/72
5,247,244 A * 9/1993 Miller .................... G02F 1/0305
324/105
(Continued)

FOREIGN PATENT DOCUMENTS

CN        103091529 A  *  5/2013

OTHER PUBLICATIONS

Ackermann et al., Designing the optical interface of a transcutaneous optical telemetry link, IEEE Transcactions on Biomedical Engineering, 55:1365-73 (2008).
(Continued)

*Primary Examiner* — Lee E Rodak
*Assistant Examiner* — Demetrius R Pretlow
(74) *Attorney, Agent, or Firm* — MARSHALL, GERSTEIN & BORUN LLP

(57) ABSTRACT

The following relates generally to optical voltage sensing, and in particular to optical voltage sensing of power grids and of a subject body. For example, some embodiments include an optical resonator comprising: (i) a top electrode layer, (ii) a piezoelectric layer, and (iii) a substrate. A light source may illuminate the optical resonator of the voltage sensor with light comprising an incident optical power at an input wavelength, where the input wavelength is offset from a resonant wavelength of the optical resonator by a baseline voltage. The applied voltage may then be measured by measuring a reflected or transmitted light power.

22 Claims, 31 Drawing Sheets

(58) Field of Classification Search
CPC ...... G01R 31/08–086; G01R 31/31728; G01R 1/36; H10N 30/302; H10N 30/853
See application file for complete search history.

(56) References Cited

U.S. PATENT DOCUMENTS

| | | | | |
|---|---|---|---|---|
| 5,479,106 | A * | 12/1995 | Takahashi | G01R 31/308 324/750.16 |
| 9,823,277 | B1 * | 11/2017 | Lagakos | G01R 19/0092 |
| 2021/0103007 | A1 * | 4/2021 | Gordon | G01R 15/248 |
| 2021/0286129 | A1 * | 9/2021 | Fini | G02B 6/12007 |
| 2023/0024557 | A1 * | 1/2023 | Niewczas | G01R 15/247 |

OTHER PUBLICATIONS

Ayazian et al., Delivering optical power to subcutaneous implanted devices, 2011 Annual International Conference of hte IEEE Engineering in Medicine and Biology Society, pp. 2874-2877 (2011).

Boales et al., Measurement of nonlinear piezoelectric coefficients using a micromechanical resonator, Applied Physics Letters, 113:083501 (2018).

Chaisakul et al., Recent progress on ge/sige quantum well optical modulators, detectors, and emitters for optical interconnects, Photonics, vol. 6, pp. 24, MDPI (2019).

Cho et al., Amorphous si/sio2 distributed bragg reflectors with transfer printed single-crystalline si nanomembranes, Journal of Vacuum Science & Technology B, 34(4):040601 (2016).

Cortese et al., Microscopic sensors using optical wireless integrated circuits, Proc. Natl. Acad. Sci., 117:9173-9 (2020).

Dante et al., A temperature-independent interrogation technique for fbg sensors using monolithic multilayer piezoelectric actuators, IEEE Transactions on Instrumentation Measurements, 65:2476-84 (2016).

Du et al., Crystal orientation dependence of piezoelectric properties of lead zirconate titanate near the morphotropic phase boundary, Applied Physics Letters, 72:2421-3 (1998).

Duan et al., Recent advances of optical imaging in the second near-infrared window, Adv. Materials, 30:1802394 (2018).

Gonçalves et al., A temperature-independent optical voltage transformer based on fbg-pzt for 13.8 kv distribution lines, Measurement, 147:106891 (2019).

Hui et al., Tracking algorithm for the gain of the phase modulator in closed-loop optical voltage sensors, Optics & Laser Technology, 47:214-20 (2013).

Kano et al., Temperature dependence of piezoelectric properties of sputtered AlN on silicon substrate, Sensors Actuators A: Physics, 130:397-402 (2006).

Lee et al., Meeting the electrical, optical, and thermal design challenges of photonic-packaging, IEEE Journal Selected Topics Quantum Electronics, 22:409-17 (2016).

Leung et al., Piezoelectric coefficient of aluminum nitride and gallium nitride, J. Applied Physics, 88:5360-3 (2000).

Li et al., An analysis on hte optimization of closed-loop detection method for optical voltage sensor based on pockels effect, J. Lightwave Technology, 32:1006-13 (2014).

Li et al., Determination of temperature dependence of piezoelectric coefficients matrix of lead zirconate titanate ceramics by quasi-static and resonance method, Journal of Physics D: Applied Physics, 42:095417 (2009).

Molnar et al., Nanoliter-scale autonomous electronics: advances, challenges and opportunities, 2021 IEEE Custom Integrated Circuits Conferece (CICC) pp. 1-6 (2021).

Mujeeb-U-Rahman et al., Optical power transfer and communication methods for wireless implantable sensing platforms, J. Biomed. Optics, 20:1-9 (2015).

Rahmatian et al., 138 kv and 345 kv wide-band sf/sub 6/-free optical voltage transducers, 2002 IEEE Power Engineering Society Winter Meeting. Conference Proceedings (Cat. No. 02CH37309), vol. 2, pp. 1472-1477 (2022).

Rahmatian et al., Sf/sub 6/-free 550 kv combined optical voltage and current transducer system, 2003 IEEE PES Transmission and Distribution Conference and Exposition (IEEE Cat. No. 03CH37495), vol. 1 pp. 379-382 (2003).

Rossel et al., Temperature dependence of the transverse piezoelectric coefficient of thin films and aging effects, J. Applied Physics, 115:034105 (2014).

Rumyantsev et al., Low frequencey noise and long-term stability of noncoherent light sources, J. Applied Physics, 96:966-9 (2004).

Seeley et al., Packaging and performance of a piezo-optic voltage sensor, ASME International Mechanical Engineering Congress and Exposition, vol. 42991, pp. 287-296 (2007).

Sheppard et al., Approximate calculation of the reflection coefficient from a stratified medium, Pure App. Opti. J. Eur. Opt. Soc. Part A, 4:665 (1995).

Sima et al., Temperature characteristics of pockels electro-optic voltage sensor with double crystal compensation, AIP Adv. 6, 055109 (2016).

Stelling et al., Plasmonic nanomeshes: their ambivalent role as transparent electrodes in organic solar cells, Sci. Rep., 7:1-13 (2017).

Vijatovic et al., History and challenges of barium titanate: Part ii, Sci. Sinter., 40:235-44 (2008).

Yang et al., An optical fiber bragg grating and piezo electric ceramic voltage sensor, Rev. Sci. Instruments, 88:105005 (2017).

Yoshino et al., Fiber-optic fabry-perot interferometer and its sensor applications, IEEE Trans Microwave Theory Technology, 30:1612-21 (1982).

* cited by examiner

| | 1 | 2 | 3 | AN EXAMPLE EMBODIMENT OF THE PRESENT DISCLOSURE |
|---|---|---|---|---|
| ARCHITECTURE | DUAL FBG | FBG | FBG | THIN-FILM |
| LIGHT SOURCE | BROADBAND ASE | BROADBAND ASE | SLED | LED |
| $P_{IN}$ | ~1mW | 25mW[c] | 500mW[f] | 110mW |
| $BW$ | 20KHZ | 5KHZ | 1KHZ | 5KHZ |
| $SNR_{MAX}$ | 21dB | 3dB[d] | 54dB | 35dB |
| $E_Q$ | ~370 | 2.5µJ | 1.9pJ | 13pJ |
| THD | -47dB[a] | -23dB | -51dB | -67dB |
| $\frac{(\Delta\beta/\beta)}{\Delta T}$ | 44%/°C[b] | 0.2%/°C[e] | 0.2%/°C[e] | 0.011%/°C |
| COMPENSATION | FBG | THERMAL SCREWS | BIAS POINT TRACKING | NONE |

[a] ESTIMATED FROM $V_{OUT}/V_{IN}$ TRANSFER FUNCTION.

[b] MAXIMUM DIFFERENT CHANGE IN GAIN β FROM 6°C TO 8°C.

[c] INPUT POWER NOT SPECIFIED. ASSUME MAXIMUM POWER OF TYPICAL ASE LIGHT SOURCE (500mW) WITH AN INSERTION LOSS OF 13dB.

[d] ESTIMATED FROM PSD NOISE OF 0.01V IN 16HZ BIN AND SIGNAL (INCLUDING SPECTRAL LEAKAGE) OF 0.93V ACROSS 4 BINS.

[e] ESTIMATED FROM THE TEMPERATURE COEFFICIENT OF PZT, WHICH WAS NOT ACCOUNTED FOR BY THE AUTHORS

[f] INPUT POWER NOT SPECIFIED. ASSUME POWER TYPICAL SLED LIGHT SOURCE (10mW) WITH AN INSERTION LOSS OF 13dB.

FBG: FIBER BRAGG GRATING
Δβ/β: NORMALIZED SENSORS GAIN

1. Q. YANG, Y. HE, S. SUIN, M. LUO, AND R. HAN, "AN OPTICAL FIBER BRAGG GRATING AND PIEZOELECTRIC CERAMIC VOLTAGE SENSOR," REV. SCI. INSTRUMENTS 88, 105005 (2017).

2. M.N GONCALVES AND M.M. WERNECK, "A TEMPERATURE-INDEPENDENT OPTICAL VOLTAGE TRANSFORMER BASED ON FBG-PZT FOR 13.8KV DISTRIBUTION LINES, " MEASUREMENT 147, 106891 (2019).

3. A. DANTE, R. BACURAU, A. W. SPENGLER, E. C. FERREIRA, AND J. A. S. DIAS, " A TEMPERATURE-INDEPENDENT INTERROGATION TECHNIQUE FOR FBG SENSORS USING MONOLITHIC MULTILAYER PIEZOELECTRIC ACTUATORS, " IEEE TRANSACTIONS ON INSTRUMENTATION MEAS. 65, 2476-2484 (2016).

FIG. 7

| PARAMETER | VALUE | |
|---|---|---|
| $r_{33}$ | $1\,pm/V$ | [1] |
| $d_{33}$ | $5\,pm/V$ | [2] |
| $L_0$ | $295\,nm^a$ | |
| $n_0$ | $2.13$ | [3] |
| $R_{max}$ | $0.39^b$ | |
| $Q$ | $4.0^b$ | |

[a] MEASURED USING INTERFEROMETRY.
[b] BEST FIT LORENTZIAN TO MEASURED REFLECTION SPECTRA.

1  P. GRAUPNER, J. POMMIER, A. CACHARD, AND J. COUTAZ., "ELECTRO-OPTICAL EFFECT IN ALUMINUM NITRIDE WAVEGUIDES," J. APPLIED PHYSICS 71, 4136-4139 (1992).

2  C. LUENG, H.L. CHAN, C. SURYA, AND C. CHOY, "PIEZOELECTRIC COEFFICIENT OF ALUMINUM NITRIDE AND GALLIUM NITRIDE," J. APPLIED PHYSICS 88, 5360-5363 (2000).

3  J. PASTRNAK AND L.ROSKOVCOVA, "REFRACTION INDEX MEASUREMENTS ON ALN SINGLE CRYSTALS," PHYSICA STATUS SOLIDI (b) 14, K5-K8 (1996).

FIG. 8F

THIN-FILM OPTICAL VOLTAGE SENSOR FOR VOLTAGE SENSING

TECHNICAL FIELD

The present invention relates generally to optical voltage sensing, and in particular to optical voltage sensing of power grids and of a subject body.

BACKGROUND

Current systems for measuring power grid voltages typically involve instrument transformers. Although these systems are often accurate and robust to environmental conditions, they are bulky, heavy (sometimes weighing even four tons), and expensive, thus limiting their use in microgrids and distributed sensing applications. In addition, some explode when they fail.

The techniques described herein address these problems and others.

SUMMARY

Described herein are systems and methods for optical voltage sensing. Applications of the disclosed techniques include, among other things, voltage sensing of power grids, and voltage sensing within a human or animal subject.

In one aspect, there is provided a method of measuring a voltage, the method comprising: applying a voltage to an optical resonator of a voltage sensor, the optical resonator comprising: (i) a top electrode layer, (ii) a piezoelectric layer, and (iii) a substrate; illuminating, with a light source, the optical resonator of the voltage sensor with light comprising an incident optical power at an input wavelength, wherein the input wavelength is offset from a resonant wavelength of the optical resonator at a baseline voltage; and measuring the applied voltage by measuring a reflected light power reflected from the illumination by the optical resonator.

In another aspect, an optical voltage sensor may be provided. The optical voltage sensor may comprise: optical resonator comprising: (i) a top electrode layer, (ii) a piezoelectric layer, and (iii) a substrate. The optical voltage sensor may further comprise one or more processors configured to: determine a reflected light power created by light incident on the optical resonator, the light incident on the optical resonator comprising an incident optical power at an input wavelength, wherein the input wavelength is offset from a resonant wavelength of the optical resonator; and measure, based on the reflected light power reflected from the optical resonator, an applied voltage applied to the optical resonator.

In yet another aspect, there is provided a method of measuring a voltage, the method comprising: applying a voltage to an optical resonator of a voltage sensor, the optical resonator comprising: (i) a top electrode layer, (ii) a piezoelectric layer, and (iii) a substrate; illuminating, with a light source, the optical resonator of the voltage sensor with light comprising an incident optical power at an input wavelength, wherein the input wavelength is offset from a resonant wavelength of the optical resonator at a baseline voltage; and measuring the applied voltage by measuring a transmitted light power transmitted from the illumination through the optical resonator.

In yet another aspect, an optical voltage sensor may be provided. The optical voltage sensor may comprise: an optical resonator comprising: (i) a top electrode layer, (ii) a piezoelectric layer, and (iii) a substrate. The optical voltage sensor may further comprise one or more processors configured to: determine a transmitted light power created by light incident on the optical resonator, the light incident on the optical resonator comprising an incident optical power at an input wavelength, wherein the input wavelength is offset from a resonant wavelength of the optical resonator; and measure, based on the determined transmitted light power, an applied voltage applied to the optical resonator.

BRIEF DESCRIPTION OF THE DRAWINGS

FIG. 7 illustrates a comparison between an example disclosed sensor and other example sensors.

FIG. 8F illustrates parameters for calculation of senor gain for an analytical model and for a thin-film Fresnel equation model.

DETAILED DESCRIPTION

The present embodiments relate to, among other things, systems and methods for optical voltage sensing. Exemplary applications of the optical voltage sensing techniques described herein include measuring power grid level voltages (e.g., tens to hundreds of KV) over a large range of environmental conditions (e.g., temperature, humidity, etc.), and measuring voltages within a subject (e.g., a human or animal subject). In addition, broadly speaking, the techniques described herein operate by measuring light either reflected by a medium, or transmitted through the medium.

Introduction and Overview

Figure 1A:
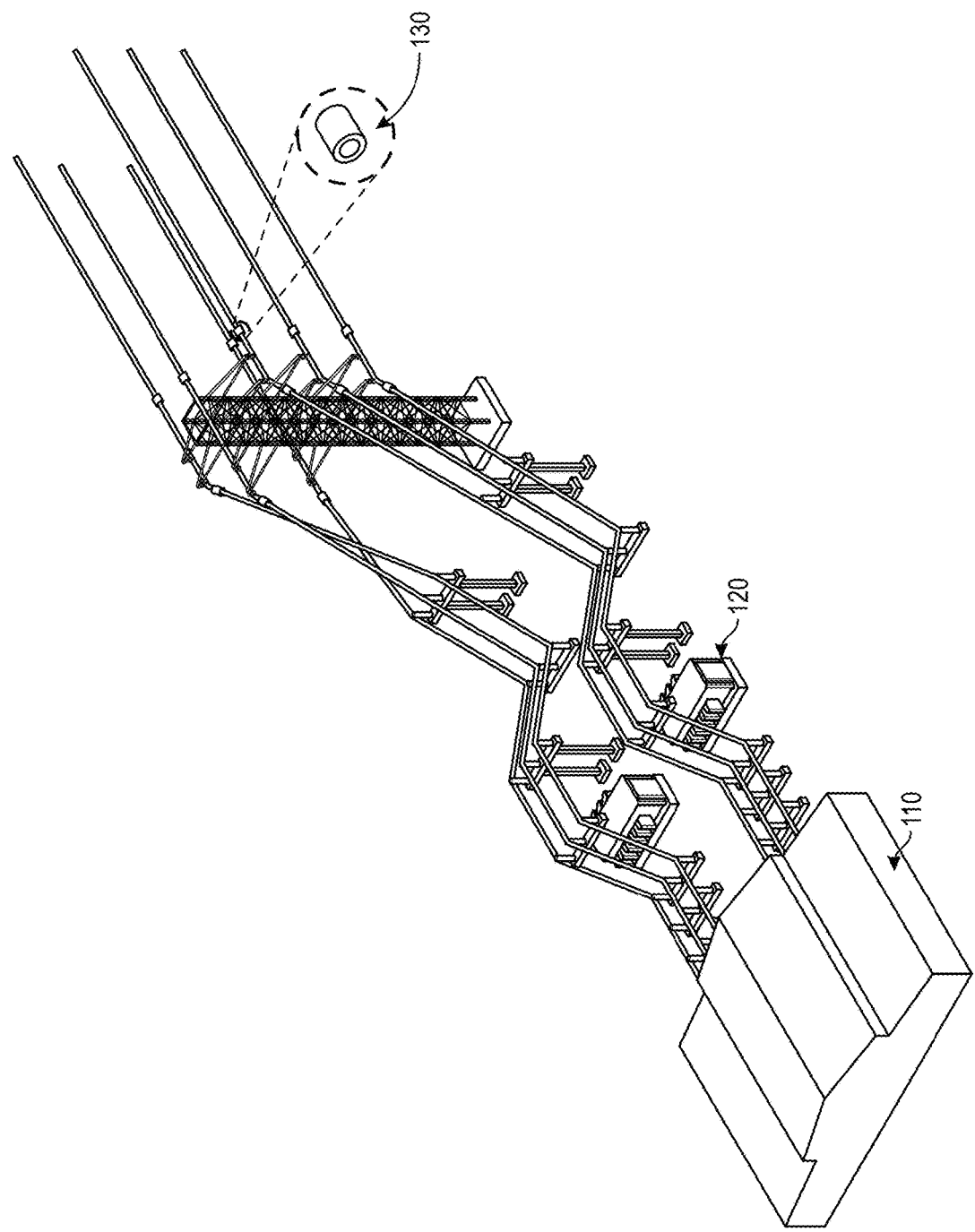
FIG. 1A illustrates an example of a power grid setup.

FIG. 1A illustrates an example of a power grid setup. Here, the power station 110 generates power, which travels to the substations 120. The substations 120 include transformers, which convert the power to high voltages for transmission over long distances. Sensors 130 are placed a key points to monitor voltages, which is useful to determine or predict, for example, where and when the power might go out.

However, safe, accurate, and economical measurement of time-varying voltages in electric power systems is a significant challenge. The standard solution to this challenge is the instrument transformer, which steps down a high voltage (~1 kV+) to an appropriate level (typically less than 100V) and isolates the stepped-down voltage, allowing safe measurement using conventional electronics. However, these transformers are bulky and expensive, and sometimes explode (~3% of all installed instrument transformers [see M. Poljak and B. Bojanić, "Method for the reduction of in-service instrument transformer explosions," Eur. transactions on electrical power 20, 927-937 (2010)]).

Optical methods for direct measurement of high voltages have gained attention since the early 1980s [see T. Yoshino, K. Kurosawa, K. Itoh, and T. Ose, "Fiber-optic fabry-perot interferometer and its sensor applications," IEEE Transactions on Microw. Theory Tech. 30, 1612-1621 (1982)], mainly due to the high available bandwidth (~GHz), intrinsic electrical isolation, and the potential for low cost and remote monitoring. Initial optical voltage sensors consisted of long (several meters) optical fiber wrapped around a piezoelectric material [see Id.]. In these sensors, when the piezo material was excited by a voltage, it grew or shrank proportional to the applied voltage, changing the fiber optical path length; the resulting change in the optical path length was measured using interferometry to infer the voltage amplitude. More recent optical methods include coupling piezoelectric material to the resonant frequency of Bragg fiber gratings [see C. E. Seeley, G. Koste, B. Tran, and T. Dermis, "Packaging and performance of a piezo-optic voltage sensor," in ASME International Mechanical Engineering Congress and Exposition, vol. 42991 (2007), pp. 287-296; Q. Yang, Y. He, S. Sun, M. Luo, and R. Han, "An optical fiber bragg grating and piezoelectric ceramic voltage sensor," Rev. Sci. Instruments 88, 105005 (2017); and M. N. Gonçalves and M. M. Werneck, "A temperature-independent optical voltage transformer based on fbg-pzt for 13.8 kv distribution lines," Measurement 147, 106891 (2019)].

However, the sensors based on the these previous optical methods are inaccurate due to their nonlinearities [M. N. Gonçalves and M. M. Werneck, "A temperature-independent optical voltage transformer based on fbg-pzt for 13.8 kv distribution lines," Measurement 147, 106891 (2019)] or temperature sensitivity [Q. Yang, Y. He, S. Sun, M. Luo, and R. Han, "An optical fiber bragg grating and piezoelectric ceramic voltage sensor," Rev. Sci. Instruments 88, 105005 (2017); M. N. Gonçalves and M. M. Werneck, "A temperature-independent optical voltage transformer based on fbg-pzt for 13.8 kv distribution lines," Measurement 147, 106891 (2019); and A. Dante, R. M. Bacurau, A. W. Spengler, E. C. Ferreira, and J. A. S. Dias, "A temperature-independent interrogation technique for fbg sensors using monolithic multilayer piezoelectric actuators," IEEE Transactions on Instrumentation Meas. 65, 2476-2484 (2016)]. Closed-loop compensation methods were used to improve the accuracy of such sensors [see L. Hui, B. Lan, L. Lijing, H. Shuling, F. Xiujuan, and Z. Chunxi, "Tracking algorithm for the gain of the phase modulator in closed-loop optical voltage sensors," Opt. & Laser Technol. 47, 214-220 (2013); and H. Li, L. Cui, Z. Lin, L. Li, and C. Zhang, "An analysis on the optimization of closed-loop detection method for optical voltage sensor based on pockels effect," J. lightwave technology 32, 1006-1013 (2014)], but these methods reduce system reliability and increase system complexity, electrical hazards, and cost.

To address these drawbacks and others, some embodiments described herein leverage the principle of optical resonance to create a smaller, more durable, and more cost-effective voltage sensor. Fundamentally, output nonlinearity and temperature dependence increase with an increasing quality factor (Q) of the interferometric- or optical resonator-based sensor, where Q is defined as the ratio of the energy stored in the optical resonator to the energy dissipated per oscillation period. Therefore, a low-Q sensor is desirable to minimize nonlinearity and temperature dependence. However, low-Q sensors suffer from low sensitivity, resulting in a low signal-to-noise ratio (SNR) and poor performance. In practice, the SNR, and hence performance, can be improved independently of the sensor sensitivity by increasing the incident optical power ($P_{in}$) or reducing the operating bandwidth (BW). This makes performance comparison of different optical voltage sensors difficult; they must be operated with the same $P_{in}$ and BW, for a fair comparison.

Given this, a $P_{in}$ and BW independent figure of merit (FoM) is required to quantify the noise performance of optical voltage sensors. The techniques described herein propose such a metric, the energy per quanta ($E_Q$), which depends only on the sensor properties and dynamic input range. This metric extends the power efficiency factor used in analog circuit design [see R. Muller, S. Gambini, and J. M. Rabaey, "A 0.013 mm², 5 μw, dc-coupled neural signal acquisition ic with 0.5 v supply," IEEE J. Solid-State Circuits 47, 232-243 (2011)] and the energy per conversion-level of analog-to-digital-converters [see R. H. Walden, "Analog-to-digital converter technology comparison," in Proceedings of 1994 IEEE GaAs IC Symposium, (IEEE, 1994), pp. 217-219; and R. H. Walden, "Analog-to-digital converter technology comparison," in Proceedings of 1994 IEEE GaAs IC Symposium, (IEEE, 1994), pp. 217-219]. Lower Q-factors yield less sensitive sensors and a higher $E_Q$ ($E_Q \propto 1/Q^2$).

In this regard, some embodiments trade $E_Q$ for temperature insensitivity and reduced harmonic distortion, and explore the limits of this approach. To this end, in one example, this disclosure demonstrates a low-Q resonant optical resonator-based voltage sensor based on a piezoelectric AlN thin film that transduces a voltage applied across the piezo terminals into a change in the resonant frequency of the cavity or optical resonator. This sensor can be batch fabricated with high yield and low cost (<$1), which makes it uniquely well-suited to reduce the cost of grid voltage measurement.

In some example implementations, the optical voltage sensor comprises an optical resonator, including a piezoelectric layer. In some embodiments, the optical voltage sensor is millimeter-sized, and the piezoelectric layer is aluminum nitride (AlN) thin film for continuous measurements of AC voltages<350 $kV_{rms}$ (via capacitive division). In some implementations, this sensor operated with 110 μW incident optical power from a low-cost LED, and achieved: a resolution of 170 $mV_{rms}$ a 5 kHz bandwidth, a measurement inaccuracy of 0.04% due to sensor nonlinearity, and a gain deviation of +/−0.2% over the temperature range of ~20-60° C. In some implementations, the sensor has a breakdown voltage of 100V, and its lifetime can meet or exceed that of instrument transformers when operated at voltages<42$V_{rms}$. The sensor, in some embodiments, reduces the cost of grid monitoring, thus providing a path towards more distributed sensing and control of the grid.

Figure 1B:
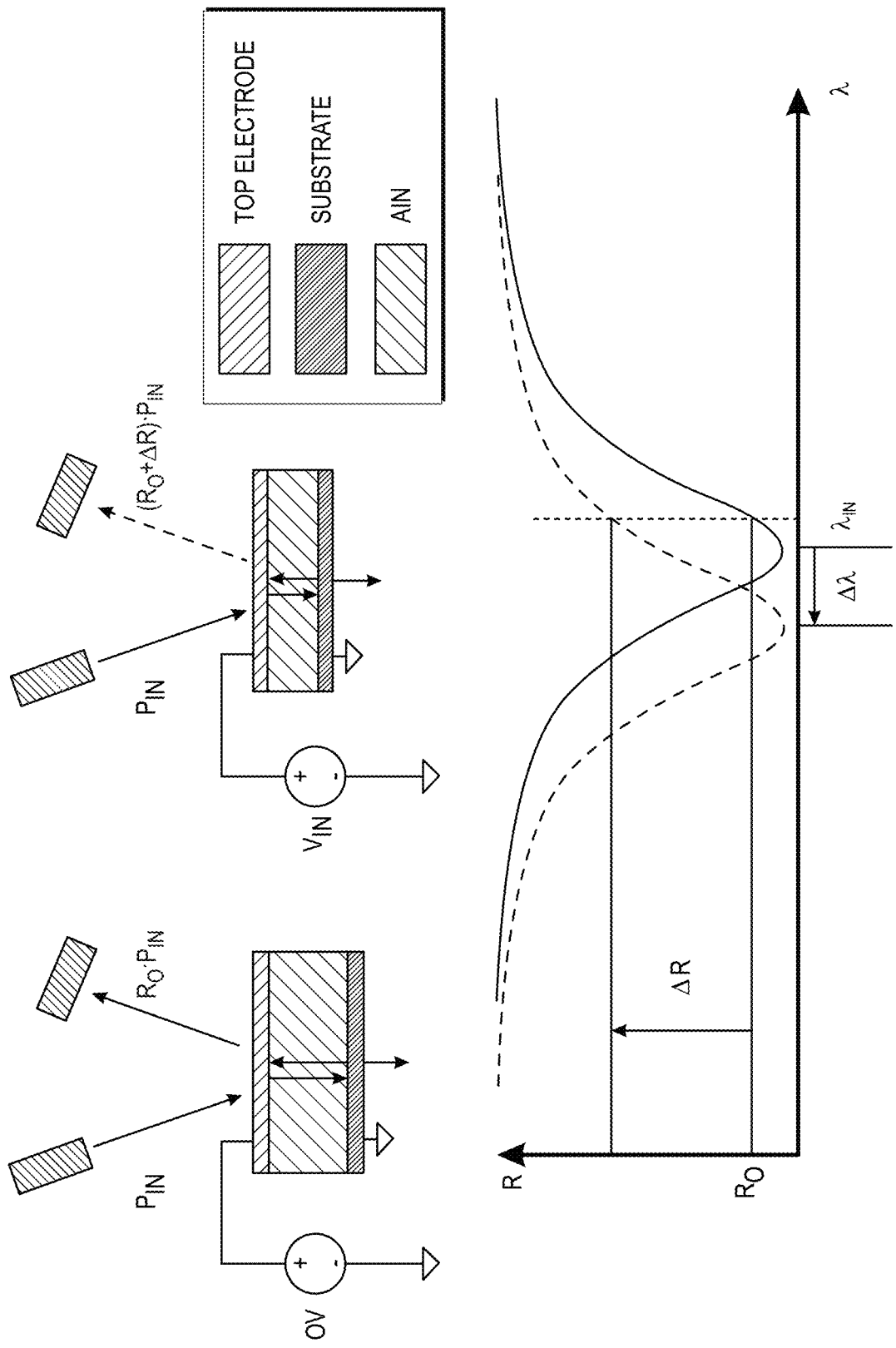
FIG. 1B shows an example of an operating principle of an embodiment of an optical voltage sensor (OVS).

Optical Voltage Sensor Design and Sensor Fabrication
Operating Principle and Fabrication Process of the Sensor FIG. 1B shows an example of an operating principle of an embodiment of an optical voltage sensor (OVS) based on changes in the measured reflectance of an optical resonator, whose thickness varies with applied voltage. The example optical resonator is formed by an AlN thin film sandwiched between the top indium tin oxide (ITO) electrode and the bottom silicon (Si) substrate. During operation, the sensor is illuminated by a light source with an incident optical power ($P_{in}$) at a fixed wavelength ($\lambda_{in}$) near (e.g., offset from) the resonance wavelength of the optical resonator (λr). Some fraction of $P_{in}$ is reflected from the optical resonator, with the remainder dissipated in or transmitted through the optical resonator, as seen in FIG. 1B. Here, the intensity of reflected light ($P_r = P_{in} \times R$, where R is the optical resonator reflectance) is measured by a photodetector to detect the amplitude of an input voltage ($V_{in}$) applied across the optical resonator. $P_r$ depends on Vi, through R as $V_{in}$ (e.g., by $P_r = (R_0 + \Delta R) \cdot P_{in}$) generates an electric field in the optical resonator that changes the AlN film thickness [C. Lueng, H. L. Chan, C. Surya, and C. Choy, "Piezoelectric coefficient of aluminum nitride and gallium nitride," J. applied physics 88, 5360-5363 (2000)] and refractive index [P. Gräupner, J. Pommier, A. Cachard, and J. Coutaz, "Electro-optical effect in aluminum nitride waveguides," J. applied physics 71, 4136-4139 (1992)] and hence results in a shift in resonant wavelength $\Delta\lambda = \lambda_r - \lambda_{r0}$, where $\lambda_{r0}$ is the resonant wavelength at $V_{in} = 0$. The resulting $\lambda_r$ shift leads to a change in the reflectance ($\Delta R = R - R_0$, where $R_0$ is the reflectance at $V_{in} = 0$). The $\Delta R$ value at a known $V_{in}$ can be calculated using the following Equations (1) and (2):

$$\Delta R = \beta V_{in} \quad (1)$$

$$\beta = \frac{3\sqrt{3}}{4} \frac{R_{max} Q}{t} \left( d_{33} + \frac{1}{2} n_0^2 r_{33} \right) \quad (2)$$

Where $R_{max}$ is the amplitude of the resonant dip (always <1), Q and t are the quality factor and thickness of the optical resonator, $d_{33}$ is the thickness mode piezoelectric strain coefficient, $n_0$ is the (unperturbed) refractive index of the AlN thin film, and $r_{33}$ is the Pockels coefficient (which relates the refractive index to the applied electric field). This equation is valid near $\lambda_{in} \approx \pm \lambda_r 1/\sqrt{3} \cdot FWHM$; this corresponds to the steepest point on the reflectance curve, where FWHM is the full-width-half max of the resonant dip.

It may be noted that the example of FIG. 1B illustrates the difference between applied voltages of 0V and $V_{in}$, the difference between any two voltages may be used (e.g., the difference between a baseline voltage, and $V_{in}$).

Moreover, as described herein, the optical power may be measured via the transmitted light power (e.g., light transmitted through the piezoelectric layer), rather than the reflected light power. In this regard, the reflectance measuring and transmittance measuring configurations are similar. However, in the transmittance measuring configuration, the substrate should be transparent to the incident wavelength. Furthermore, it should be noted that the transmittance curve of the device itself is simply one minus the reflectance curve (e.g., transmittance curve=1−reflectance curve), and thus the same considerations apply. In some embodiments, the transmitted light power is measured via a fiber optic cable coupled to the device.

Figure 2A:
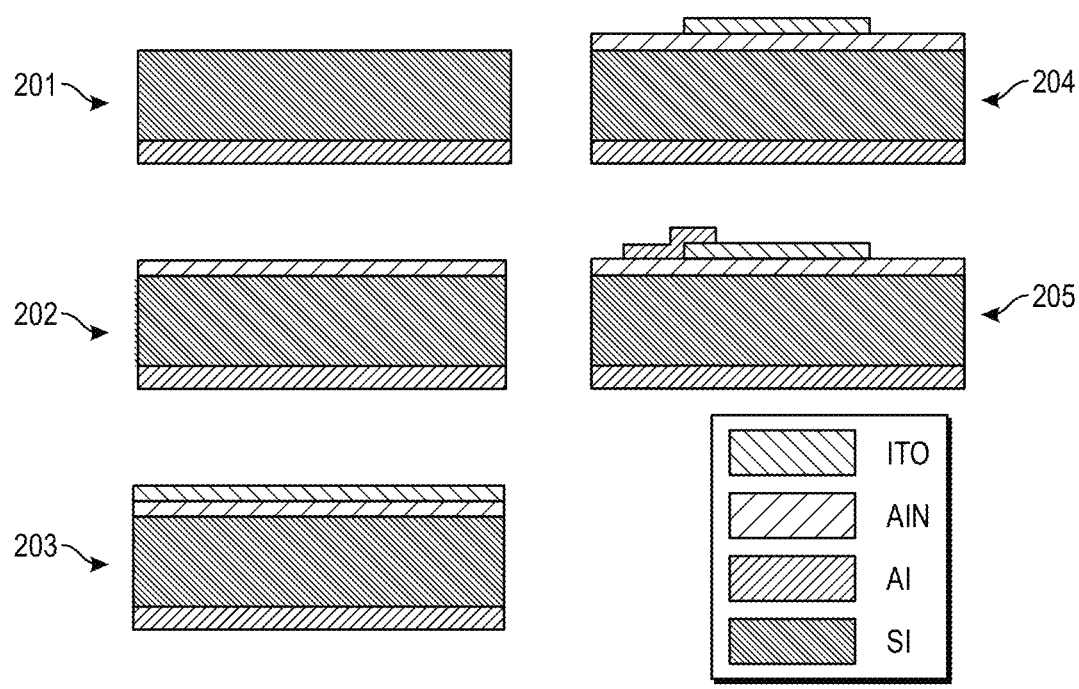
FIG. 2A shows an example optical voltage sensor (OVS) fabrication process.
Figure 2B:
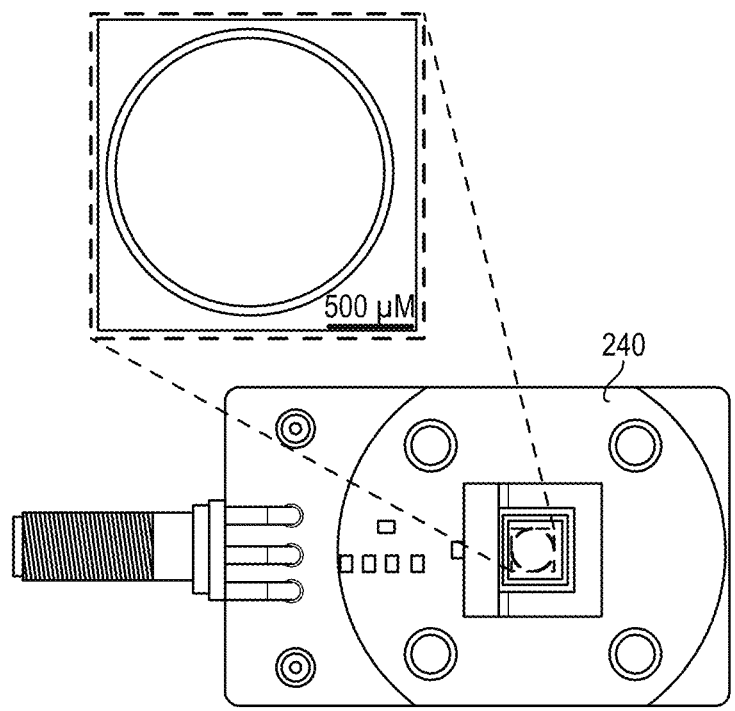
FIG. 2B illustrates an example printed circuit board (PCB), and an optical micrograph of the 2 mm diameter sensor.
Figure 2C:
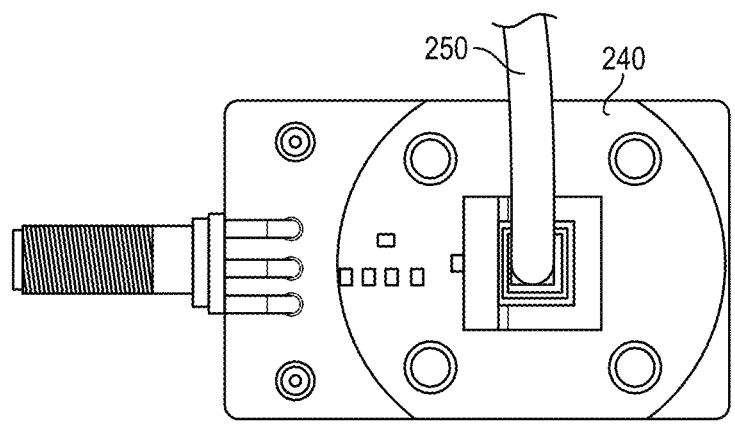
FIG. 2C illustrates an example where a fiber optic cable is coupled to the sensor in order to measure optical power transmitted through the optical resonator.

FIG. 2A shows an example OVS fabrication process. With reference thereto, all lithography in the example is done in a DUV stepper (ASML), on a 150 mm-thick silicon (Si) wafer. At 201, a ~300 nm-thick layer of backside aluminum (AI) is sputtered, and then the wafer is annealed at 300° C. for 15 min in atmosphere to create backside ohmic contacts that serves as the bottom electrode. At 202, a 300 nm-thick aluminum nitride (AlN) film (endeavor AT) is sputtered. At 203, a 20 nm-thick indium tin oxide (ITO) film is sputtered to serve as the transparent top electrode. At 204, lithographic patterning and ion milling create the mesas. At 205, the example process patterned the top ITO contacts to form 2 mm diameter devices and evaporated 20 nm titanium (Ti)/300 nm Al to form bond pads. The fabricated 10×10 mm² sensor die was attached with conductive silver epoxy and wire-bonded to a printed circuit board (PCB) 240. An optical micrograph of the 2 mm diameter sensor on its PCB 240 are shown in FIG. 2B The die size was designed to be larger than the actual device size to facilitate easy handling. FIG. 2C illustrates an example where a fiber optic cable 250 is coupled to the sensor in order to measure optical power transmitted through the optical resonator.

Furthermore, optical shot noise sets a hard limit on OVS performance. The performance of optical detection systems is bounded by shot noise received at the photodetector. For a shot noise limited OVS system, the system SNR is proportional to the input optical power, which is given by $I_{pd}^2/I_{noise}^2 = \Delta I_{pd}^2/(2q(I_{pd}+\Delta I_{pd})\cdot BW)$, where q is the electron charge, $I_{pd}$ is the light-induced photocurrent on the photodetector, $\Delta I_{pd}$ is the change in the rms photocurrent induced by an applied input voltage ($V_{in}$), and BW is the system bandwidth. The SNR can also be expressed in terms of an incident optical power ($P_{in}$), the average device reflectance ($\langle R \rangle$), and an rms modulation depth ($\Delta R$, that is, the change in R due to an applied $V_{in}$) in the following form, using $I_{pd} = P_{in} \cdot \mathfrak{R} \cdot R$:

$$SNR \approx \frac{P_{in} \mathfrak{R} \cdot \Delta R^2}{2q \cdot \langle R \rangle \cdot BW} \quad (3)$$

Where $\mathfrak{R}$, is the responsivity of the photodetector. Equation (3) reveals the system SNR depends not only on $V_{in}$ through R but also $P_{in}$ and BW, consistent with the expectation that larger $P_{in}$ and smaller BW, provide a better SNR in the optical voltage sensing system. However, optical sources can only supply a limited amount of power, and system-level requirements could potentially limit the maximum $P_{in}$ and the minimum BW in the system.

Moreover, the input-referred energy per quanta ($E_Q$) allows quantitative configuration-independent sensor comparison. Since the best choices for $P_{in}$ and BW will vary by application, it is useful to introduce a metric that normalizes SNR to $P_{in}$ and BW. This would allow a rigorous noise performance comparison between optical voltage sensors, independent of the sensor's particular operating $P_{in}$ or BW. In digital systems (optical and otherwise), the energy per bit has become a ubiquitous metric of device performance [see R. S. Tucker, "Green optical communications-part i: Energy limitations in transport," IEEE J. selected topics quantum electronics 17, 245-260 (2010)]. The techniques disclosed herein propose an alternative metric for analog systems, the energy per quanta ($E_Q$), defined as:

$$E_Q \equiv \frac{P_{in}}{SNR \cdot BW} \quad (4)$$

This metric demonstrates how efficiently $P_{in}$ is used, and can be interpreted as a cost paid in energy to achieve a desirable SNR. For a shot noise limited system, $E_Q$ can be derived, independent of $P_{in}$ and BW, by inserting Equation (3) into Equation (4):

$$E_{Q,min} \approx \frac{q \cdot \langle R \rangle}{\mathfrak{R} \cdot \Delta R^2} \quad (5)$$

The form of this equation makes it clear that reducing the average optical resonator reflectance $\langle R \rangle$ the expense of modulation depth $\Delta R$ at the operating wavelength can improve the noise performance of the system, as observed in [D.-J. Lee and J. F. Whitaker, "Optimization of sideband modulation in optical-heterodyne-downmixed electro-optic sensing," Appl. optics 48, 1583-1590 (2009)]. $E_Q$ is bounded from below by the incident photon energy captured by the photodetector.

Optical Voltage Sensor (OVS) Design

Some embodiments of the OVS are designed to measure grid-level AC voltages in the range of tens to hundreds of kVs via capacitive division. The system bandwidth (BW) may be set to 5 kHz, satisfying the BW requirement of most grid applications, including inverter-based solar [see L. Fan, Z. Miao, and M. Zhang, "Subcycle overvoltage dynamics in solar pvs," IEEE Transactions on Power Deliv. 36, 1847-1858 (2020)]. To minimize sensor nonlinearity and temperature sensitivity, some embodiments are designed such that the sensor has a high $E_Q$, as $d\hat{\beta}/dT \propto 1/E_Q$ and $d\hat{\beta}/dV_{in} \propto 1/E_Q$ (where $\beta$ is the sensor gain, shown in Equation (2), and $\hat{\beta}=\beta(V_{in}, T)/\beta(0,0)$ is the normalized gain). To achieve a high $E_Q$, some embodiments minimize the sensor Q-factor by designing the optical resonator as thin as possible (L=300 nm) and excluding mirrors (other than the material interfaces).

Furthermore, most previous sensors use lead zirconate titanate (PZT) as a piezoelectric material to form the optical resonator as it provides a large piezoelectric strain coefficient ($d_{33}\approx500$ pm/V [see X.-h. Du, J. Zheng, U. Belegundu, and K. Uchino, "Crystal orientation dependence of piezoelectric properties of lead zirconate titanate near the morphotropic phase boundary," Appl. physics letters 72, 2421-2423 (1998)]). However, the PZT $d_{33}$ is extremely temperature sensitive (~20% over 100° C.) [F. Li, Z. Xu, X. Wei, and X. Yao, "Determination of temperature dependence of piezoelectric coefficients matrix of lead zirconate titanate ceramics by quasi-static and resonance method," J. Phys. D: Appl. Phys. 42, 095417 (2009)]. Therefore, some embodiments use aluminum nitride (AlN) for the sensor to further minimize the sensor temperature dependence as its $d_{33}$ is independent of temperature [see K. Kano, K. Arakawa, Y. Takeuchi, M. Akiyama, N. Ueno, and N. Kawahara, "Temperature dependence of piezoelectric properties of sputtered ain on silicon substrate," Sensors Actuators A: Phys. 130, 397-402 (2006); and C. Rossel, M. Sousa, S. Abel, D. Caimi, A. Suhm, J. Abergel, G. Le Rhun, and E. Defay, "Temperature dependence of the transverse piezoelectric coefficient of thin films and aging effects," J. Appl. Phys. 115, 034105 (2014)].

Experiment Results

Figure 3:
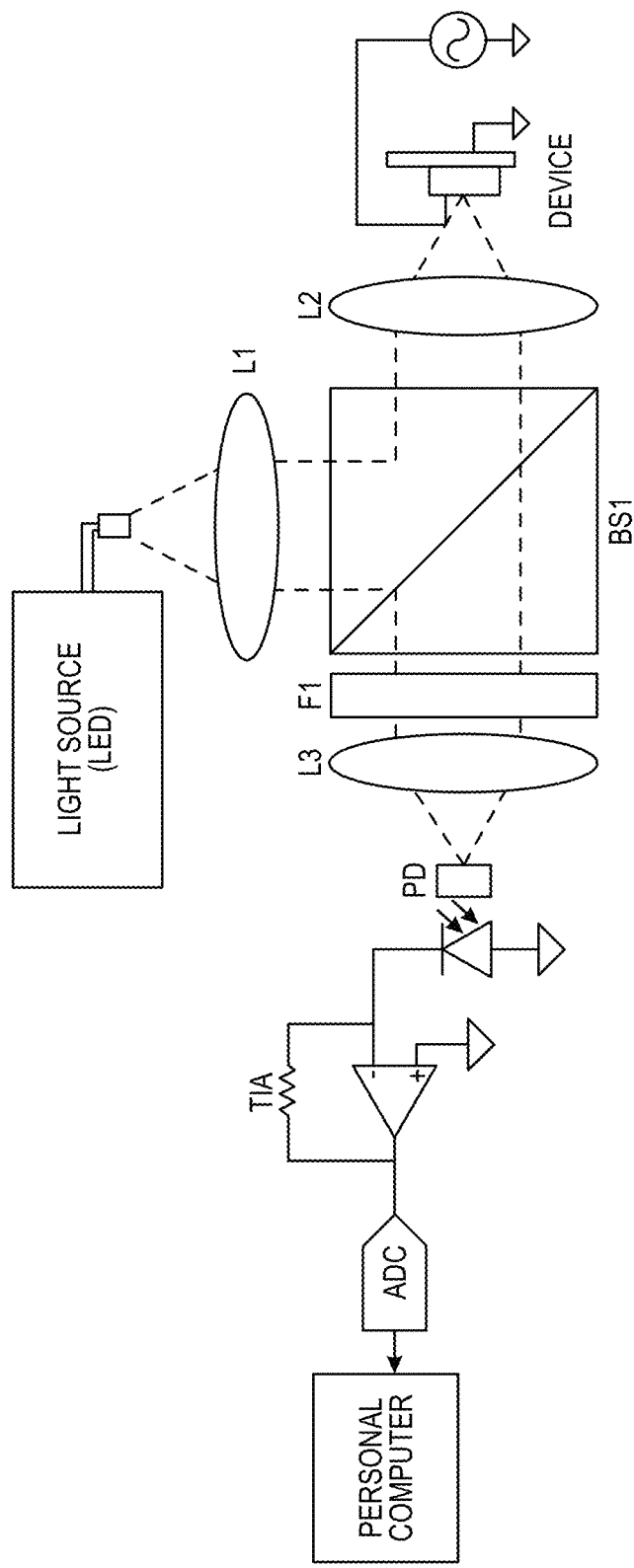
FIG. 3 illustrates an example setup for optical measurement of a voltage.

FIG. 3 illustrates one example setup. In this example, light is emitted by an LED source, focused onto device, imaged onto a photodiode, and measured with a TIA. The TIA output is sent to the ADC to be recorded in the computer.

With continuing reference to the example of FIG. 3, an LED was used with a peak intensity at ~970 nm(±10 nm) and a mean intensity at ~950 nm. The light from the LED was fiber-coupled to collimating lens L1, beam-splitter BS1, focusing lens L2, focusing lens L3, 850 nm long-pass filter F1 and Si photodiode PD. The PD was connected to a transimpedance amplifier (TIA) with a 1M feedback resistance to convert a light-induced photocurrent on the PD to a voltage. The resulting voltage was digitized by an analog-to-digital converter (ADC) with a 10 kHz sampling rate and then sent to a computer through a serial link for data storage and further analysis.

Figure 4A:
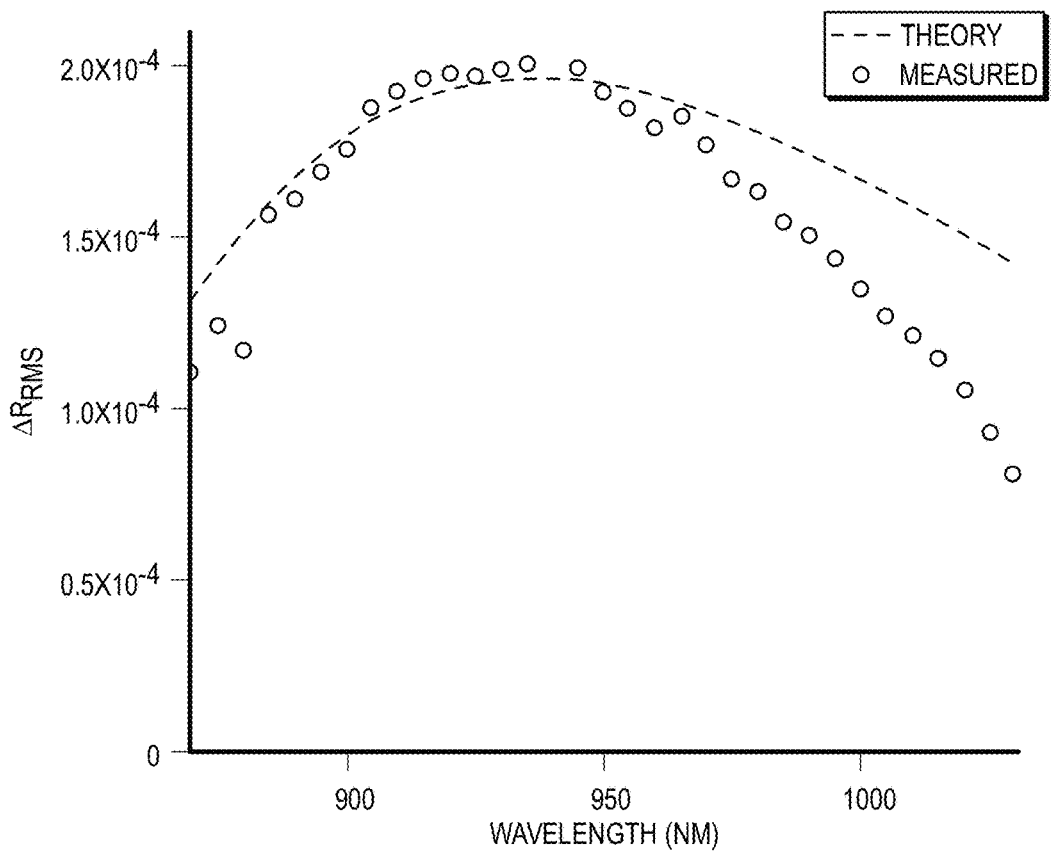
FIG. 4A depicts an example measured $\Delta R_{rms}$ spectra for a sensor operated at $V_{in}$ of $20V_{pp}$.

To extract the modulation depth ($\Delta R_{rms}$) spectrum of the OVS, some embodiments apply a 105 Hz sinusoidal signal ($V_{in}$) to the sensor and used a 2.4 nm bandwidth monochromator with the LED. Note that, in the example experiment, the monochromator was only used in the $\Delta R_{rms}$ measurement. The collected photocurrent spectrum data was normalized to the data obtained in the same manner using a 120 nm gold-coated sample. FIG. 4A depicts the measured $\Delta R_{rms}$ spectra for the sensor operated at $V_{in}$ of $20V_{pp}$, showing good agreement with the $\Delta R_{rms}$ spectra predicted from a thin-film Fresnel equation model using the parameters provided in FIG. 8F. The difference in the measured and predicted spectra can be mainly attributed to the Si substrate becoming increasingly transparent at longer wavelengths, causing the transmitted light through the AlN layer (subsequently reflected by the Si/Al interface) to partially cancel the reflected light from the optical resonator.

Figure 4B:
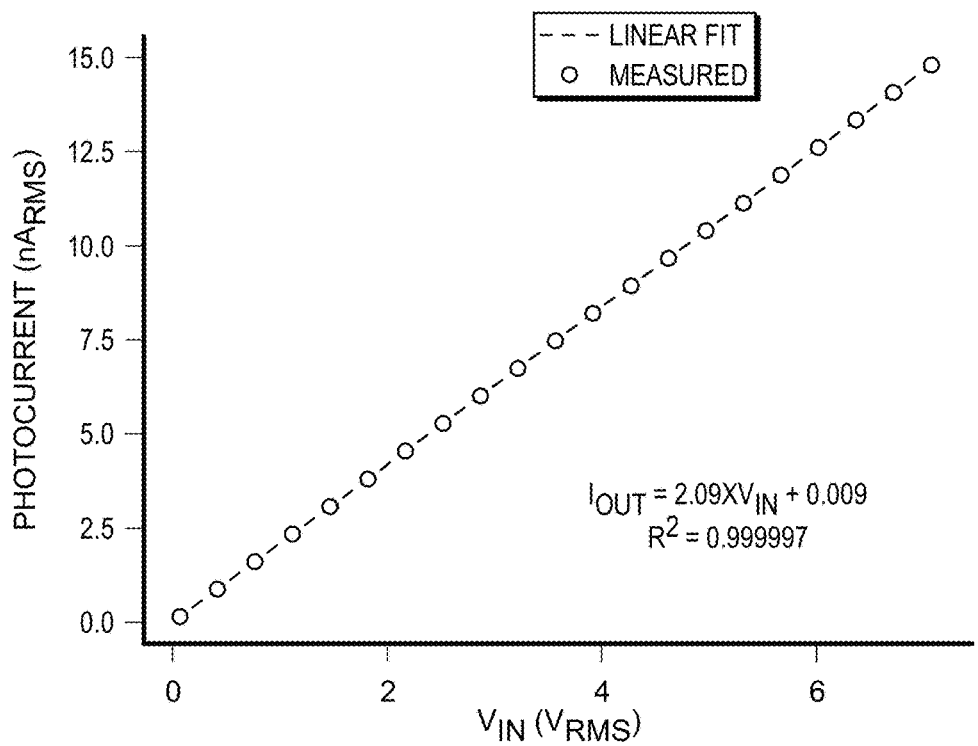
FIG. 4B depicts an example of the output photocurrent as a function of $V_{in}$.

The sensor operated with an incident optical power ($P_{in}$) of 110 µW exhibits a resolution of 170 mV$_{rms}$ in a 5 kHz bandwidth with a full scale of 140V$_{rms}$. FIG. 4B depicts the output photocurrent as a function of $V_{in}$ (105 Hz sinusoidal signal). The sensor operated with $P_{in}$ of 110 µW shows a sensitivity of 2.09 nA/V and a noise floor of 5.0 pA/$\sqrt{Hz}$, yielding a voltage resolution of 2.4 mV/$\sqrt{Hz}$, corresponding to 170 mV$_{rms}$ in a 5 kHz bandwidth. Note that the measured noise floor was in excess of the shot noise limit (2.3 pA/$\sqrt{Hz}$) by 6.6 dB, dominated by the noise from the LED.

Figure 4C:
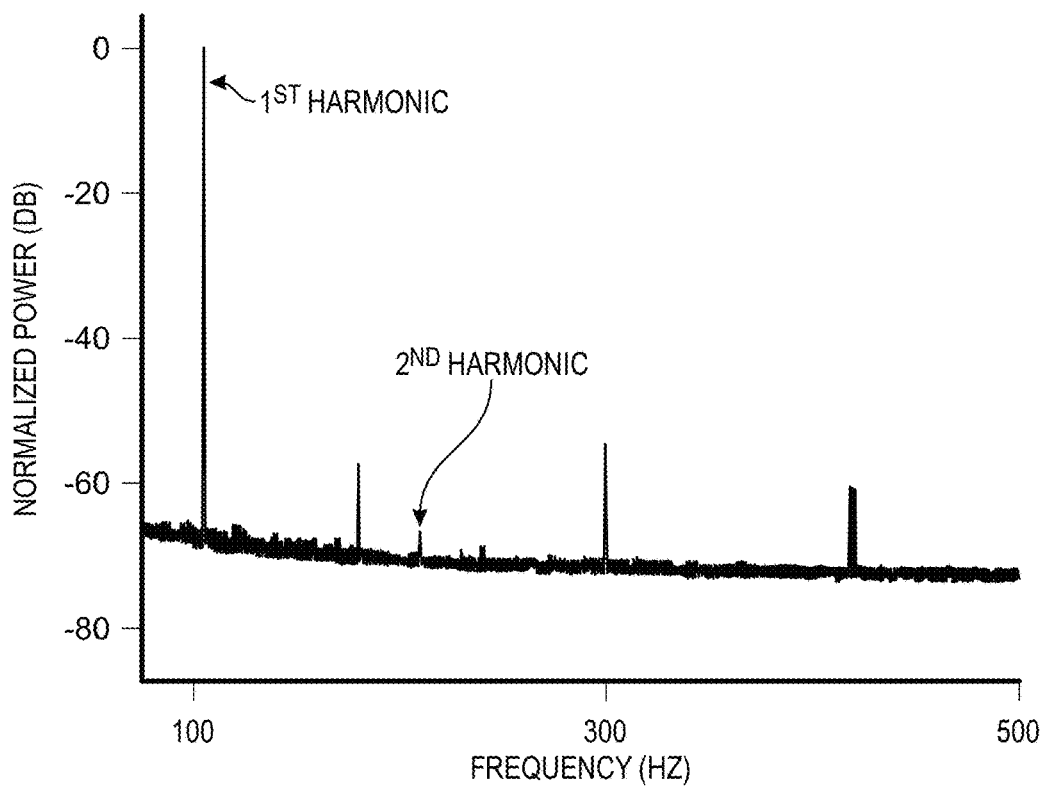
FIG. 4C shows an example normalized power spectral density of the sensor output.

The sensor nonlinearity resulted in a measurement inaccuracy of only 0.04%. In the nonlinearity test, the sensor was operated with $V_{in}$=20V$_{pp}$ and $P_{in}$=~110 µW. FIG. 4C shows the normalized power spectral density of the sensor output. The second harmonic power (−67.3 dB) corresponds to a measurement inaccuracy of 0.04% in the sensor output; this result is consistent with the nonlinearity of AlN reported in [J. A. Boales, S. Erramilli, and P. Mohanty, "Measurement of nonlinear piezoelectric coefficients using a micromechanical resonator," Appl. Phys. Lett. 113, 083501 (2018)]. The third harmonic is invisible in the spectrum as its power is below the sensor noise level. The other tones seen in FIG. 4C are the 60 Hz interference tone and its numerous harmonics.

Figure 5:
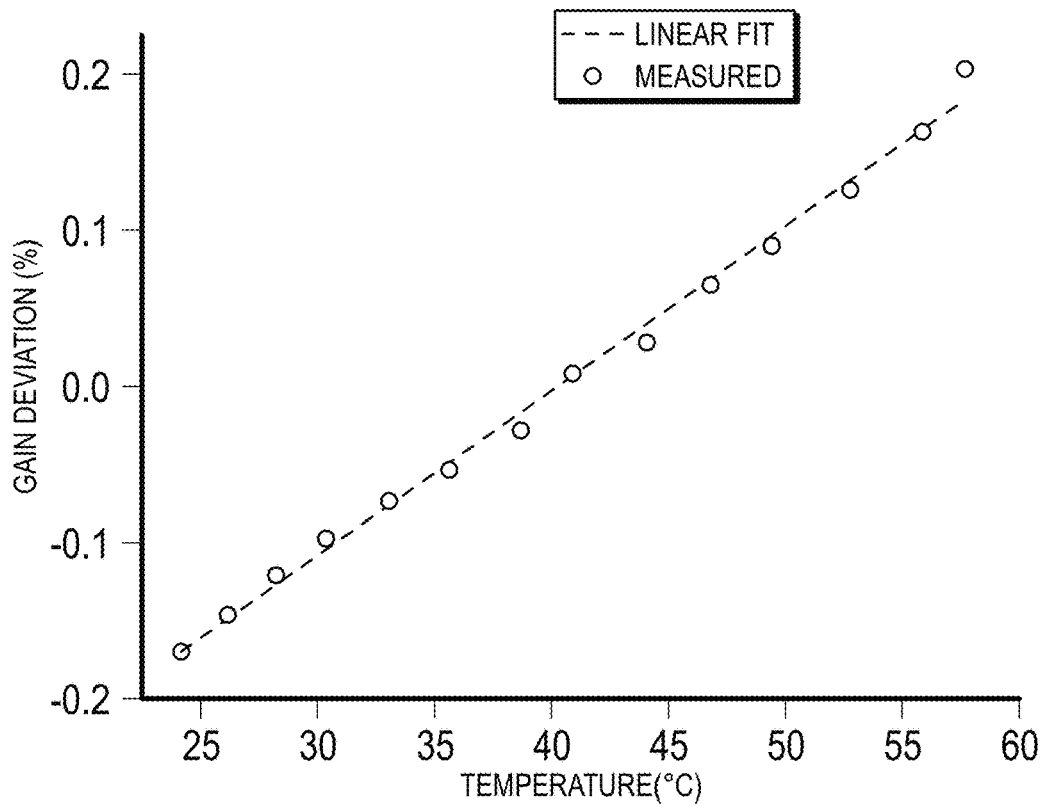
FIG. 5 illustrates an example of gain deviation vs. temperature.

The sensor output varied only +/−0.2% over a ~40° C. temperature range. This example experiment disclosed herein measured the temperature dependence of the sensor gain (β, see Equation (2)). During the measurement, the sensor, operated with a 20V$_{pp}$, 105 Hz sinusoidal signal (Vi), was placed on a 250 µm-thick polyimide heater that was controlled using a PID controller and a K-type thermocouple attached to the sensor die. The measurement result in FIG. 5 showed that the sensor gain varies only +/−0.2% in the temperature range of 23-57° C., yielding a temperature sensitivity of ~0.01%/° C. The measured ($\Delta\beta/\beta$)/$\Delta T$ may be fitted using a monochromatic Fresnel equation based optical model [E. Hecht and A. Zajac, Optics, vol. 4 (Addison Wesley San Francisco, 2002)], with the incident wavelength as the fitting parameter. From this model, the incident wavelength was fit to 940 nm, which is 10 nm lower than the LED's mean emission wavelength, within the manufacturer's tolerance. This is about 30 nm away from the optimal operation wavelength of 911 nm at which point the error is predicted to be quadratic with temperature, with a max deviation of less than +/−0.02%.

Figure 6:
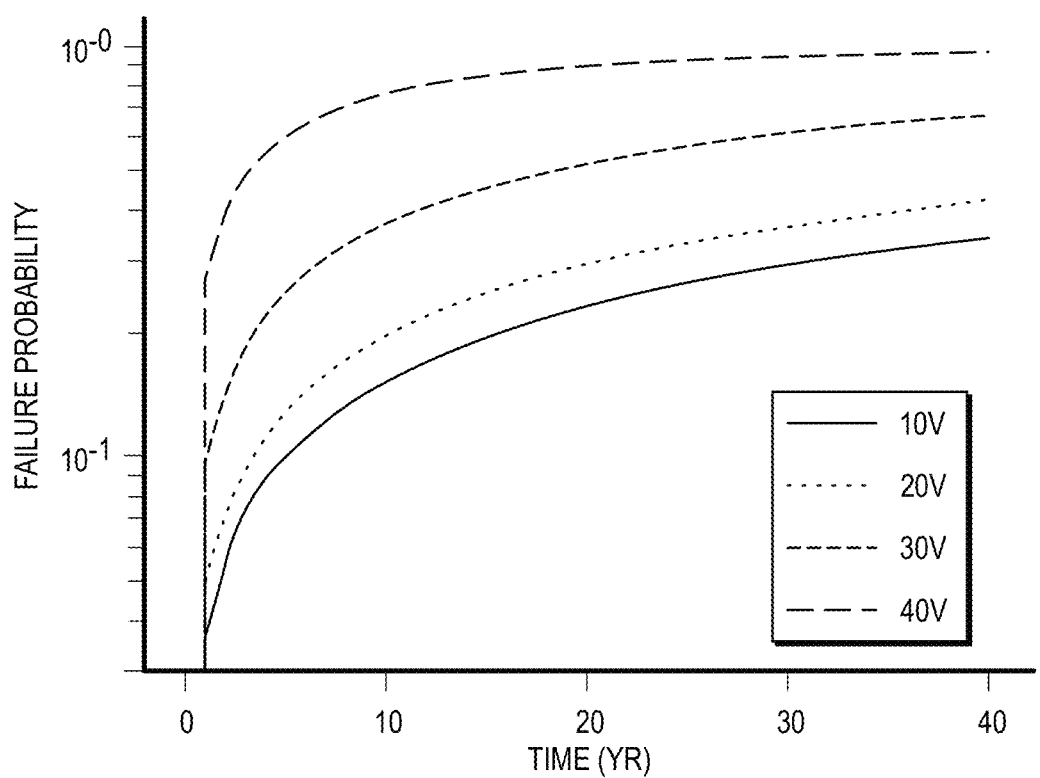
FIG. 6 illustrates an example of failure probability vs. time.

Sensor lifetime can meet or exceed that of instrument transformers. To determine the maximum electric field (E) that could be safely applied to the sensor along with the expected sensor lifetime, the experiment measured the breakdown charge $Q_{bd}$ of eight sensors with low leakage currents of less than 0.1 nA at 10V DC input voltage ($V_{in}$) [J. Verweij and J. Klootwijk, "Dielectric breakdown i: A review of oxide breakdown," Microelectron. J. 27, 611-622 (1996)]. During the measurement, these sensors were subjected to a linear voltage ramp to 43V, followed by a temperature ramp (~5° C./min) to 180° C., and recorded the current over time until the point of failure. The obtained data were fit to a Weibull distribution [J. I. McCool, Using the Weibull distribution: reliability, modeling, and inference, vol. 950 (John Wiley & Sons, 2012)], whose cumulative distribution function (CDF) is:

$$1 - e^{-\left(\frac{Q}{Q_0}\right)^\gamma} \tag{6}$$

Where $\gamma$ is the Weibull slope and $Q_0$ is the characteristic charge. The example experiment extracted values of $\gamma$=0.67 and $Q_0$=379 mC (FIG. 8B). Combining the extracted Weibull CDF (FIG. 8B) with the leakage current at room temperature (FIG. 8C), the experiment estimated the likelihood of sensor failure over time at various operating input voltages (see FIG. 6).

Discussion—Power Grid Embodiments

Monitoring grid-level voltage up to ~350 kV$_{rms}$ is possible through capacitive division. Since the optical voltage sensor (OVS) is based on a 300 nm AlN thin film, a large device capacitance (>1 nF) is possible despite the small sensor size (2 mm diameter) and relatively low-permittivity dielectric ($\epsilon_r$=9.5). One example implementation measured the sensor impedance using an LCR meter from 10 kHz-500 kHz (FIG. 8D), and extracted the device capacitance (C=0.997 nF) and resistance (R=389Ω) from fitting the measured data to a series R/C model. This relatively high capacitance allows for off-the-shelf capacitors (>~1 pF) to be used for capacitive division and hence to facilitate measuring high voltages in the order of tens to hundreds of kVs. Additionally or alternatively, fabricating the device on an insulating substrate also enables capacitive division. For example, a quartz substrate ($\epsilon_r$=4.5 [J. Krupka, K. Derzakowski, M. Tobar, J. Hartnett, and R. G. Geyer, "Complex permittivity of some ultralow loss dielectric crystals at cryogenic temperatures," Meas. Sci. Technol. 10, 387

(1999)]) with a typical thickness of 675 µm can be used to fabricate the sensor and form a capacitive divider on the same die; the quartz capacitance density (0.06 pF/mm$^2$) is much lower than the AlN film capacitance density (280 pF/mm$^2$) and allows approximately 5000:1 capacitive division for the same size sensor and capacitor. (In some embodiments, to ensure proper capacitive division, it is simply ensured that a ratio of the capacitive density of the piezoelectric layer to a capacitive density of the substrate is greater than 4,500 to 1). With a breakdown voltage of 100V, this could enable voltage sensing up to 350 kV$_{rms}$, but one can choose to operate the sensor with voltages<350 kV$_{rms}$ to extend the sensor operational lifetime.

Figure 9A:
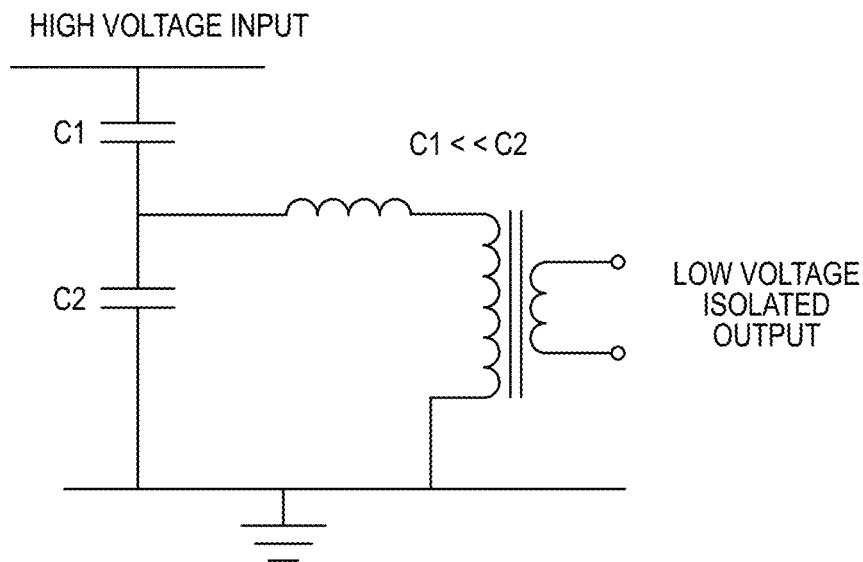
FIG. 9A illustrates an example of a high input voltage being stepped down via capacitive division.

FIG. 9A illustrates an example of a high input voltage being stepped down via capacitive division. In particular, the capacitors C1 and C2 step down the voltage, as the capacitance is such that C1<<C2. In this example, the illustrated inductive transformer further steps down and isolates the voltage for measurement.

Figure 9B:
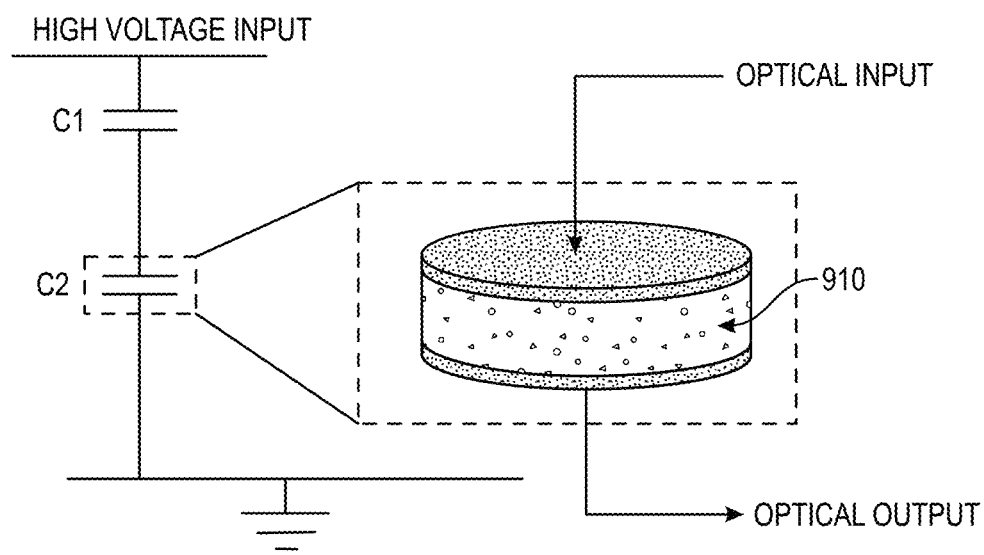
FIG. 9B illustrates an example a high input voltage being stepped down via capacitive division, including a piezoelectric layer.

FIG. 9B illustrates an example a high input voltage being stepped down via capacitive division, including an piezoelectric layer 910. As in the example of FIG. 9A, the voltage is stepped down because the capacitance is such that C1<<C2. However, in the example of FIG. 9B, the capacitance of C1 and C2 may be provided by an optical voltage sensor, as discussed above. For instance, C1 may be provided by a substrate made of quartz (e.g., having a capacitive density of 0.06 pF/mm$^2$) or other low capacitive density material; and C2 may be provided by a piezoelectric layer 910 comprising a high capacitive density material, such as AlN (e.g., 280 pF/mm$^2$).

The OVS systems disclosed herein may be low-cost and can be built using inexpensive optical components. These disclosed systems include novel OVS systems that use an LED for operation, rather than a specialized light source such as an amplified spontaneous emission source (ASE) [Q. Yang, Y. He, S. Sun, M. Luo, and R. Han, "An optical fiber bragg grating and piezoelectric ceramic voltage sensor," Rev. Sci. Instruments 88, 105005 (2017); and M. N. Gonçalves and M. M. Werneck, "A temperature-independent optical voltage transformer based on fbg-pzt for 13.8 kv distribution lines," Measurement 147, 106891 (2019)] or superluminescent LED (SLED) [A. Dante, R. M. Bacurau, A. W. Spengler, E. C. Ferreira, and J. A. S. Dias, "A temperature-independent interrogation technique for fbg sensors using monolithic multilayer piezoelectric actuators," IEEE Transactions on Instrumentation Meas. 65, 2476-2484 (2016)] (see FIG. 7). The disclosed low Q-factor device enables using a conventional broadband light source LED without the need of an optical filter, which allows sensor operation at higher powers near baseband with lower noise floors. This is because LEDs do not suffer from the same low-frequency excess noise that other narrowband light sources, such as lasers, do and can approach very closely to the shot noise limit [S. Rumyantsev, M. Shur, Y. Bilenko, P. Kosterin, and B. Salzberg, "Low frequency noise and long-term stability of noncoherent light sources," J. applied physics 96, 966-969 (2004)]. Additionally, the sensor can be interrogated at an angle or in a transmissive configuration; this allows input and output fibers to be coupled directly to the sensor, without the necessity of using optical circulators or beamsplitters. Since this device is a relatively large size (mm-scale) it does not require precise alignment. Taken together, these properties can enable building an optical voltage sensing system based on our sensor and inexpensive optical components (LEDs and optical fibers), which could bring the cost of production below that of a commonly used instrument transformer or prior OVS systems [Q. Yang, Y. He, S. Sun, M. Luo, and R. Han, "An optical fiber bragg grating and piezoelectric ceramic voltage sensor," Rev. Sci. Instruments 88, 105005 (2017); M. N. Gonçalves and M. M. Werneck, "A temperature-independent optical voltage transformer based on fbg-pzt for 13.8 kv distribution lines," Measurement 147, 106891 (2019); and 6. A. Dante, R. M. Bacurau, A. W. Spengler, E. C. Ferreira, and J. A. S. Dias, "A temperature-independent interrogation technique for fbg sensors using monolithic multilayer piezoelectric actuators," IEEE Transactions on Instrumentation Meas. 65, 2476-2484 (2016)].

The OVS trades energy per quanta ($E_Q$) for temperature insensitivity and linearity. Some embodiments of the disclosed sensor represent one extreme within the spectrum of all possible OVSs by deliberately excluding mirrors to reduce the Q-factor; the low Q-factor allows for some embodiments of the sensor to achieve better total harmonic distortion (THD) and temperature-induced relative gain error ($\Delta\beta/\Delta T$)) (without any compensation) than that of prior work, as shown in FIG. 7.

As demonstrated, the noise efficiency of OVSs, represented by $E_Q$, can be traded directly with nonlinearity and temperature dependence of the sensor output; $E_Q$ can be improved at the expense of an increase in nonlinearity and temperature sensitivity by increasing the sensor's Q-factor (as will be described further below in the "additional measurements and data section"). For a sensor that is desired to be operated with a low $E_Q$, the sensor design can be modified to incorporate mirrors on either side of the piezoelectric AlN thin film; this will improve the sensor Q-factor and hence improve the $E_Q$. Alternatively, the sensor thickness can be increased to increase the Q-factor (as will also be described further below in the "additional measurements and data section") and reduce $E_Q$, allowing the sensor to operate at higher input voltages.

Some implementations of the disclosed OVS operate within 6.6 dB of the shot noise limit with no source feedback. Previous systems, as shown by their high $E_Q$ values (see FIG. 7), are operating well above the shot noise limit, wasting input photons. Some embodiments of the disclosed systems operate within 6.6 dB of the shot noise limit, with the primary excess noise due to the optical source. This efficient use of photons allows a low noise floor to be achieved despite a low modulation depth; this eliminates the need for closed-loop feedback to reduce the noise of the optical source, further reducing the cost and complexity of a potential OVS system.

There are, however, some limitations of the energy per quanta ($E_Q$) metric. The $E_Q$ is a useful figure of merit when trying to use optical systems as sensors rather than (digital) communication devices because it is not a direct measure of energy per information (bit) used to express the energy efficiency in digital communication systems. Here, it represents a lower limit of noise performance for a shot noise limited optical voltage sensor (OVS) operated at a fixed bandwidth (BW) and incident optical power ($P_{in}$) and reveals the trades between sensor SNR, BW, and $P_{in}$. In order to design an efficient OVS, the operating BW can be traded directly for SNR, and $P_{in}$ can be traded for either BW, or SNR.

Power Grid Embodiments—Additional Measurements and Data

The following illustrates measurements and data from an example device as disclosed herein.

Breakdown Field

Figure 8A:
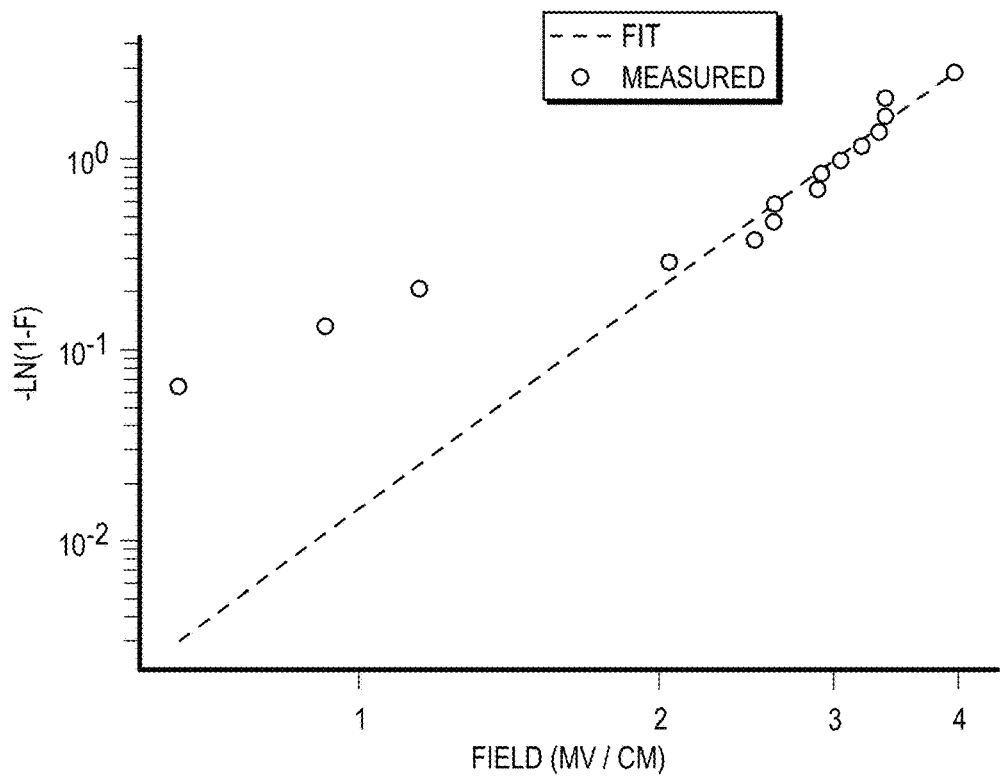
FIG. 8A illustrates measurements from an example device as disclosed herein of cumulative number of failures vs. applied electric field.
Figure 8B:
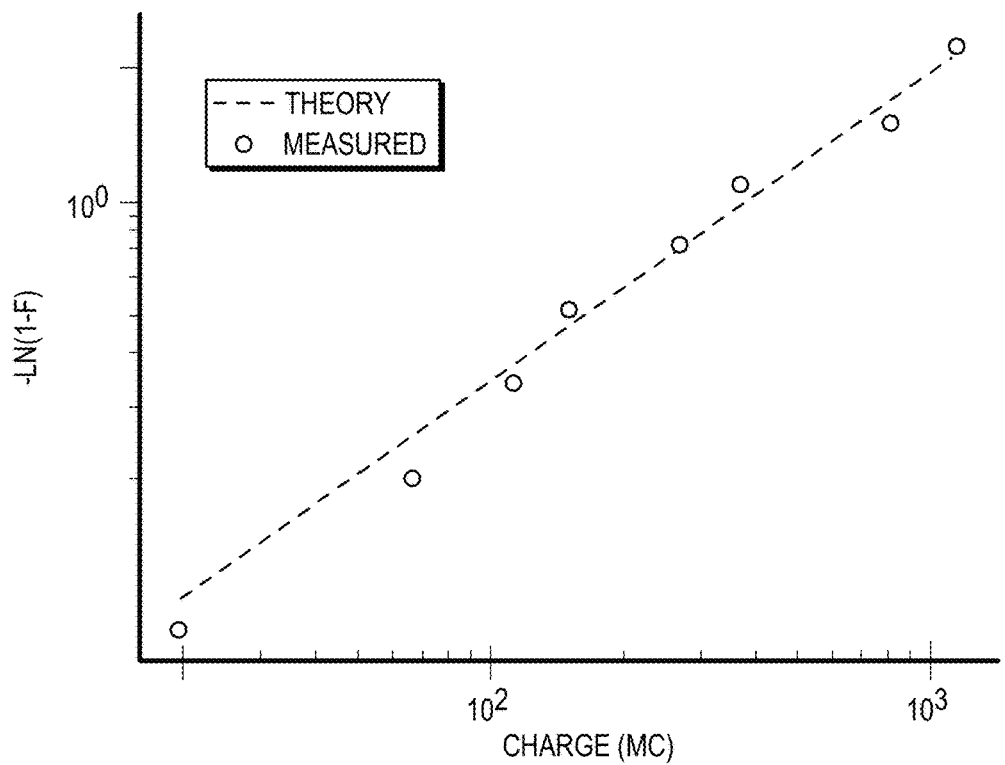
FIG. 8B illustrates measurements from an example device as disclosed herein of cumulative number of failures vs. applied charge.

FIG. 8A, in a Weibull plot, illustrates measurements from an example device as disclosed herein of cumulative number of failures vs. applied electric field. Furthermore, FIG. 8A includes a CDF of the failure probability distribution. The overall Weibull slope γ for the breakdown field was measured to be 3.8, with a characteristic field $E_0$ of 3.0 MV/cm.

Breakdown Charge

FIG. 8B, in a Weibull plot, illustrates measurements from an example device as disclosed herein of cumulative number of failures vs. applied charge. Furthermore, FIG. 8A includes a CDF of the failure probability distribution. The overall Weibull slope γ for the breakdown charge was measured to be 0.67 with a characteristic field $E_0$ of 380 mC, which corresponds to a characteristic breakdown charge density of 12 C/cm$^2$.

Leakage Current Over Voltage, Temperature

Figure 8C:
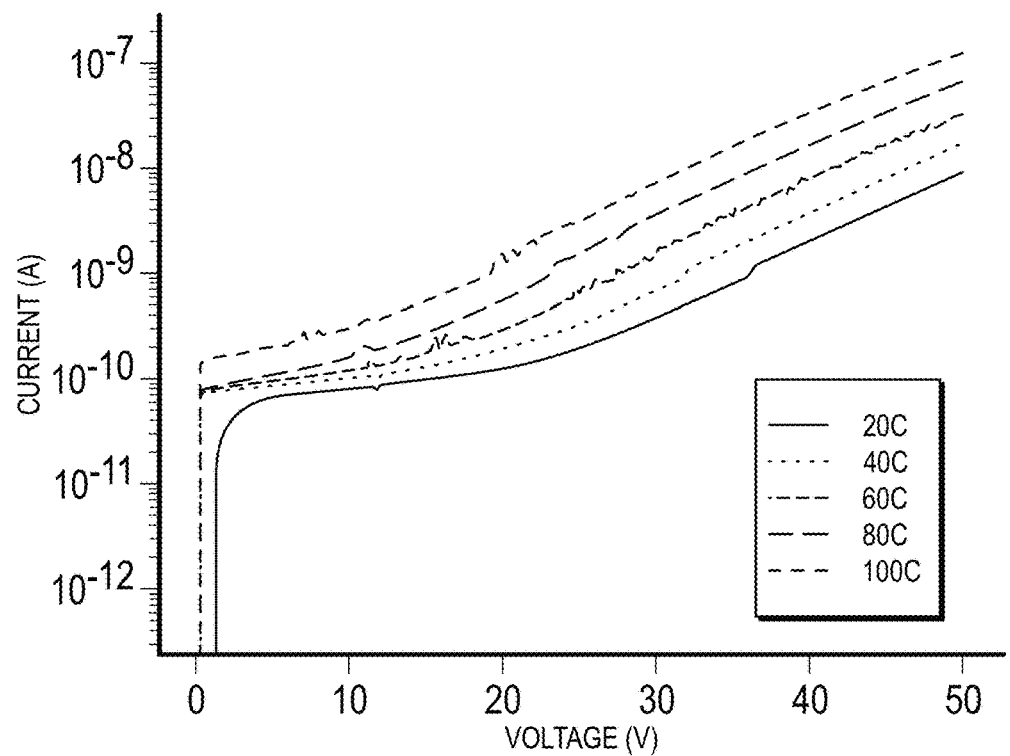
FIG. 8C illustrates examples of leakage current vs. voltage at various temperatures from 20° C. to 100° C.

FIG. 8C illustrates examples of leakage current vs. voltage at various temperatures from 20° C. to 100° C., thus ensuring the conclusions were valid at elevated temperatures. Measuring at this range of temperatures is advantageous also in that it helps predict the lifetime versus operating condition. Above approximately 20V, the leakage current increases by an order of magnitude from 20° C.-100° C., but only by a factor of 2 between 20° C. and 60° C. Colder temperatures would have lower leakage currents than shown here, and it may be expected that the average temperature over the device lifetime would be near room temperature.

Device Impedance

Figure 8D:
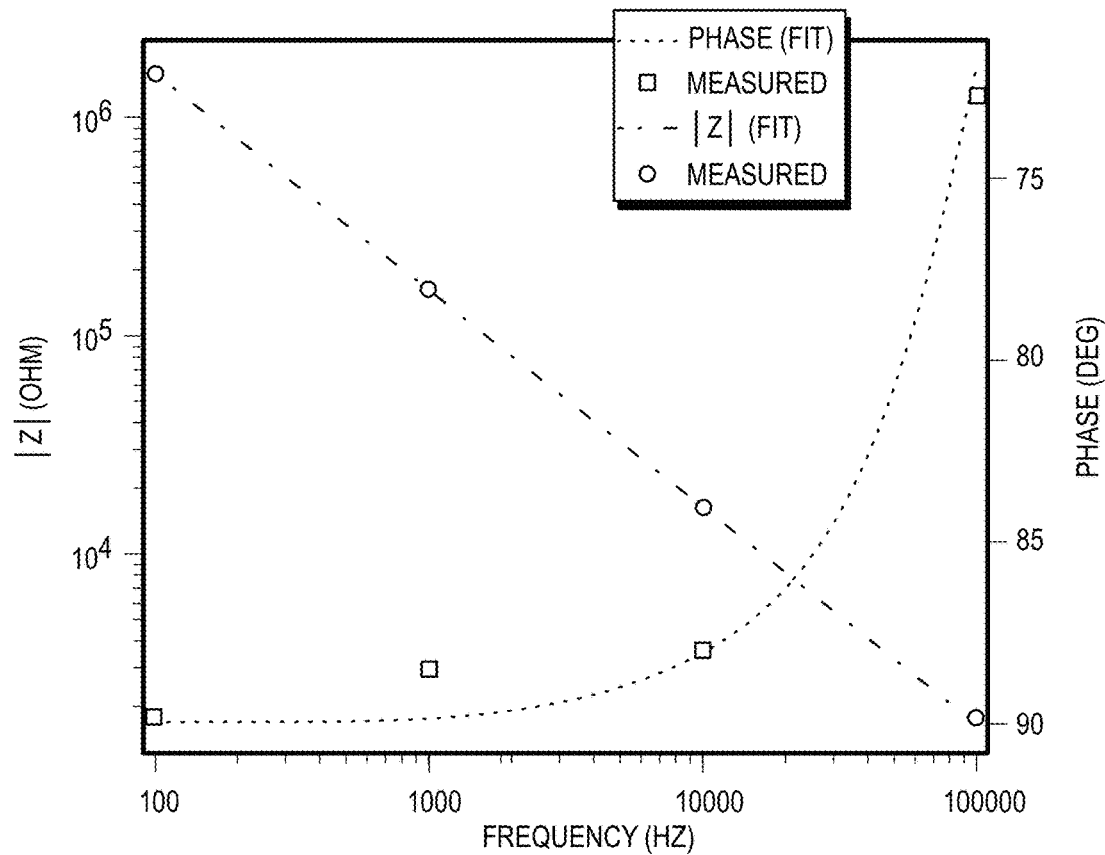
FIG. 8D illustrates an example of representative device impedance vs. frequency from 10 Hz-500 kHz.

FIG. 8D illustrates an example of representative device impedance vs. frequency from 10 Hz-500 kHz. With reference thereto, a theoretical curve was fit using an R/C series model, including fitting to the logarithm of the magnitude of Z and the phase directly using the python symfit package. Fitted series resistance was 389Ω and fitted capacitance was 997 pF.

Device Reflectance Spectra, Model Fitting

Figure 8E:
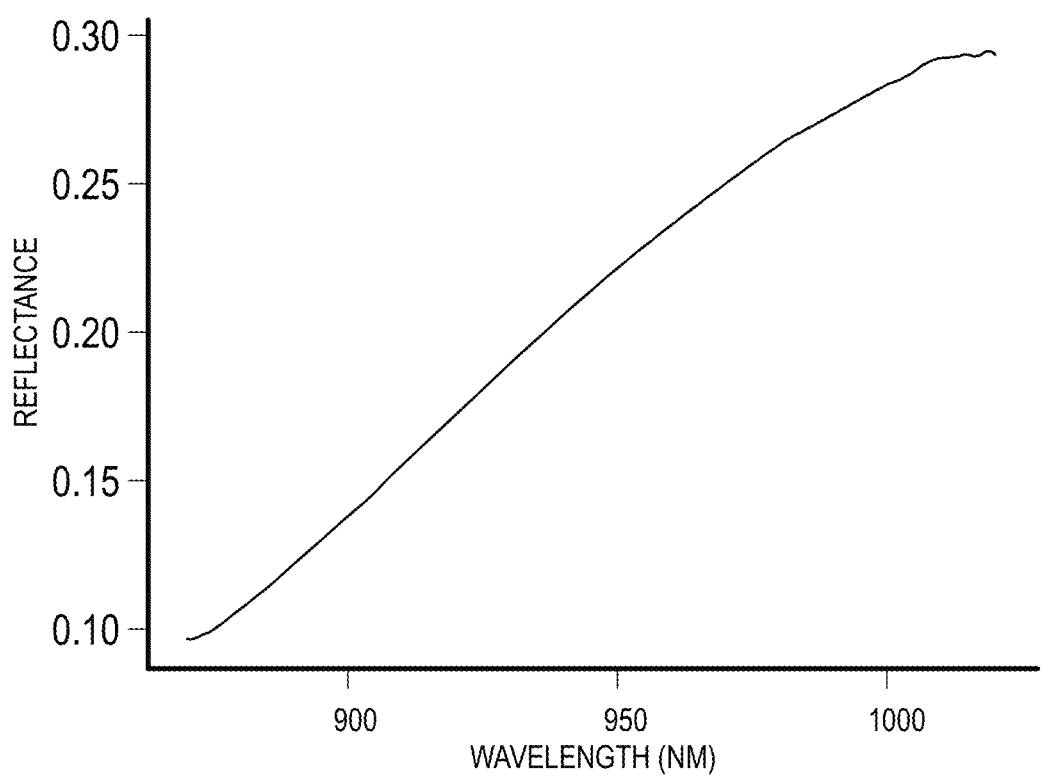
FIG. 8E illustrates an example of measured reflectance spectra of optical modulator.

FIG. 8E illustrates an example of measured reflectance spectra of optical modulator. With reference thereto, the reflectance of a single device was measured in the range 870-1020 nm. This was fit to a Lorentzian function with Q and $R_{max}$ as fitting parameters which are shown in FIG. 8F.

Example Fabrication Process

The following illustrates an example fabrication process with numbering corresponding to the example process of FIG. 2A. Prior to this example process, 0.3 um of UV210 resist was deposited, and alignment marks were patterned for layer-to-layer alignment in a ASML 5500/300 DUV stepper. Six alignment marks were then etched into the Si substrate in a Poly-Si etcher with 300 W plasma power, 150 W substrate power, 50 standard cubic centimeters per minute (sccm) chlorine gas ($Cl_2$), 150 sccm hydrogen bromide (HBr), 4 sccm helium (He), at a process pressure of 12 mTorr for 40 seconds, with a target etch depth of 120 nm.

At 201: Al Sputtering and Anneal. The example process first sputter etched the backside of the wafer at 200 W RF Power/10 sccm argon (Ar) flow for 120 seconds. Without breaking vacuum, the process then sputtered ~300 nm of aluminum (Al) at 4.5 kW DC power/15 sccm Ar flow for 60 seconds. The target was conical and 99.999% pure. To make the backside Al contact ohmic to minimize contact resistance and nonlinearity, the process annealed the wafer in an AccuThermo 610 at 300 C for 15 minutes, with an initial ramp rate of ~20° C./s at atmospheric pressure flowing pure $N_2$. The specific contact resistance at 0V dropped from 600MΩ·µm$^2$ to 5MΩ·µm$^2$ (~110× improvement), and became linear instead of rectifying.

At 202: AlN Deposition. Prior to each deposition, the process ran a bare Si conditioning wafer Al sputter to remove built-up AlN from the target. The process sputtered the target at 4 kW/6 sccm Ar flow for 5 minutes, followed by a brief (30 second) period where the process introduced $N_2$ gas, flowing 7 sccm Ar and 22 sccm $N_2$ at 4 kW power. The process then sputter etched the frontside of the device wafer at 200 W RF Power/10 sccm Ar flow for 120 seconds. Without breaking vacuum, the process then sputtered ~300 nm of aluminum nitride (AlN) at 4.5 kW, flowing 7 sccm Ar and 22 sccm $N_2$ for 420 seconds at a chamber pressure of 5 mTorr. The chamber used was dedicated to only deposit AlN.

At 203: Topside ITO Deposition. The process deposited ITO from an 8" target at 500V DC and 2 mTorr, flowing 40 sccm of Ar into the chamber for 60 seconds, for a target ITO thickness of 20 nm.

At 204: Topside ITO patterning. The process spun on 0.3 µm of UV-210 photoresist in an automated Picotrack system, exposed a full wafer of 10 mm×10 mm dies in an ASML DUV stepper (Model 5500/300) at 20 mJ/cm$^2$ dose. The process then developed the resist in MF26A developer for 60 seconds in the same automated Picotrack coating system, and UV-hard baked the resist in a Fusion Systems M200PCU. The process then ion milled the ITO layer in a Pi Scientific ion mill at 500V/250 mA at an angle of 20 degrees away from normal incidence for 60 seconds, followed by an etch at 70 degrees away from normal incidence for 20 seconds. The resist was then removed by pressurized and heated NMP (20 MPa/80° C./1000 rpm).

At 205: Al bond pad patterning. The process then spun on 1 µm of LoR-5A liftoff resist in an automated track coater (SVG 8626) for subsequent liftoff, followed by 0.87 µm of UV210 resist in an automated resist coating system (Picotrack). The process then patterned the bond pads and traces connecting the pads to the ITO layer in an ASML 5500/300 DUV stepper. The process then evaporated 20 nm titanium (Ti)/300 nm Al in an electron beam evaporator (CHA Solutions). The process deposited the Ti at 10 kV beam voltage/90 mA beam current and the Al at 10 kV/50 mA. The thickness was monitored with a 6 MHz crystal monitor.

Following the main fabrication process, individual 10 mm×10 mm chips were coated with 2 µm of protective i-Line resist and then diced in an automated dicing saw. The resist was then removed with acetone, and individual chips removed for subsequent bonding onto a PCB. The process bonded the Al-coated backside of each die to an IPA-cleaned gold (Au) 10 mm×10 mm pad on a custom PCB with two-component silver epoxy, cured at 50° C. for 30 minutes. The process then wirebonded the top 150 µm×150 µm Al bond pad to a bond pad on the PCB with 50 µm Al wire with a manual wirebonder.

Device Transfer Function, Gain

This device operates by a shift the resonant frequency, and the change in output reflectance ΔR can be linearly related to the input voltage $V_{in}$ through the gain β:(ΔR=β·$V_{in}$). The lineshape may be approximated as a Lorentzian (this approximation is equivalent to a small-angle approximation, and improves with increasing Q):

$$R(x) \approx R_{max}\left(1 - \frac{1}{1+x^2}\right) \tag{7}$$

Where x, the normalized frequency, is equal to $$\frac{\omega_r - \omega_{in}}{FWHM/2},$$

where FWHM is the full-width-halfmax of the spectral lineshape, $\omega_r$ is the resonant frequency at which destructive interference occurs, and $\omega_{in}$ is the input frequency. By expanding this in terms of derivatives and finite differences, it is found that:

$$\Delta R \approx \frac{dR}{dx} \cdot \Delta x \qquad (8)$$

$$\frac{dR}{dx} = \frac{-2R_{max}x}{(1+x^2)^2} \qquad (9)$$

$$\left(\frac{dR}{dx}\right)_{max} = \mp \frac{-2R_{max}3\sqrt{3}}{8} \qquad (10)$$

$$\Delta x = \frac{\Delta \omega_r}{FWHM/2} \qquad (11)$$

$$\Delta \omega_r \approx \omega_{r0}\left(\frac{\Delta L}{L_0} + \frac{\Delta n}{n_0}\right) \qquad (12)$$

A change in physical length occurs due to the converse piezoelectric effect:

$$\frac{\Delta L}{L_0} = \frac{d_{33} * V_{in}}{L_0} \qquad (13)$$

And a change in refractive index due to the Pockels effect:

$$\frac{\Delta n}{n_0} = \frac{n_0^2 r_{33} * V_{in}}{2L_0} \qquad (14)$$

Combining these equations together at the point of maximum gain, and recognizing that $Q=\omega_{r0}/FWHM$, it is found that:

$$\beta = \frac{3\sqrt{3}}{4}\frac{R_{max}Q}{L_0}\left(d_{33} + \frac{1}{2}n_0^2 r_{33}\right) \qquad (15)$$

Q-Factor Length Dependence

By solving the Fresnel equations [see E. Hecht and A. Zajac, Optics, vol. 4 (Addison Wesley San Francisco, 2002)] for an optical resonator with equal mirror reflectivities, it is possible to find an exact form of the optical resonator reflected intensity:

$$R = 1 - \frac{1}{1 + F * \sin^2(\phi)} \qquad (16)$$

Where F is the coefficient of finesse, which can be written in terms of the mirror reflectivity $R_m$:

$$F = \frac{4R_m}{(1-R_m)^2} \qquad (17)$$

It is possible to solve the above equations for the full-width-half-max of the spectra, and possible to obtain a form of the quality factor which depends on the incident wavelength $\lambda_{in}$ and the length and refractive index of the optical resonator:

$$Q = \frac{2\pi n L}{FWHM_\phi \lambda_{in}} \qquad (18)$$

Where $$FWHM_\phi = 2\text{Arc}\sin\left(\frac{1}{\sqrt{2+F}}\right).$$

Gain Temperature Dependence

The prior section generalizes to anything which changes the resonant frequency of the device—it need not be voltage. Thus, it is possible to take the results above to apply for temperature as well—the energy per quanta trades off linearly temperature sensitivity, as quantified by the normalized change in the gain $$E_Q \propto 1 \Big/ \frac{\Delta G}{G_{max}}(T).$$

By expanding the relative gain change $$\frac{dH}{H}$$

in terms of the resonant frequency:

$$\frac{d\beta}{\beta} = -\frac{9}{4}\Delta x^2 \qquad (19)$$

Where $\Delta x$ is the shift in normalized resonant frequency away from its optimal value, dH is the absolute change in gain and H is the gain.

$$\Delta x = \frac{\Delta \omega_r}{\gamma/2} \qquad (20)$$

Where $\omega_r$ is the resonant frequency (rad/s), and $\gamma$ is the full-width-half-max linewidth of the spectra.

$$\Delta \omega_r = \omega_r \Delta T(\alpha_n + \alpha_L) \qquad (21)$$

Where $\Delta T$ is the change in temperature, $\alpha_n$ is the relative change in refractive index (sometimes called the thermo-optic coefficient), and $\alpha_L$ is the relative change in length. Putting these three equations together, and recalling that $Q \equiv \omega_r/\gamma$, the relative change in gain is found to be:

$$\frac{d\beta}{\beta} = -9Q^2 \Delta T^2 (\alpha_n + \alpha_L)^2 \qquad (22)$$

In addition, for the parameters used to model this example device, it is expected that the change in gain over the temperature range is 0.05%.

Discussion—Neural Recording Embodiments

Some of the embodiments described above are advantageous for measuring grid-level voltages because their gain is robust to temperature and source drift, they easily perform optical alignment, and they are very linear. In addition to measuring grid-level voltages, however, the techniques described herein may be used to measure voltages within a human or animal subject; and, in this regard, some embodiments relate to neural recording.

Figure 10:
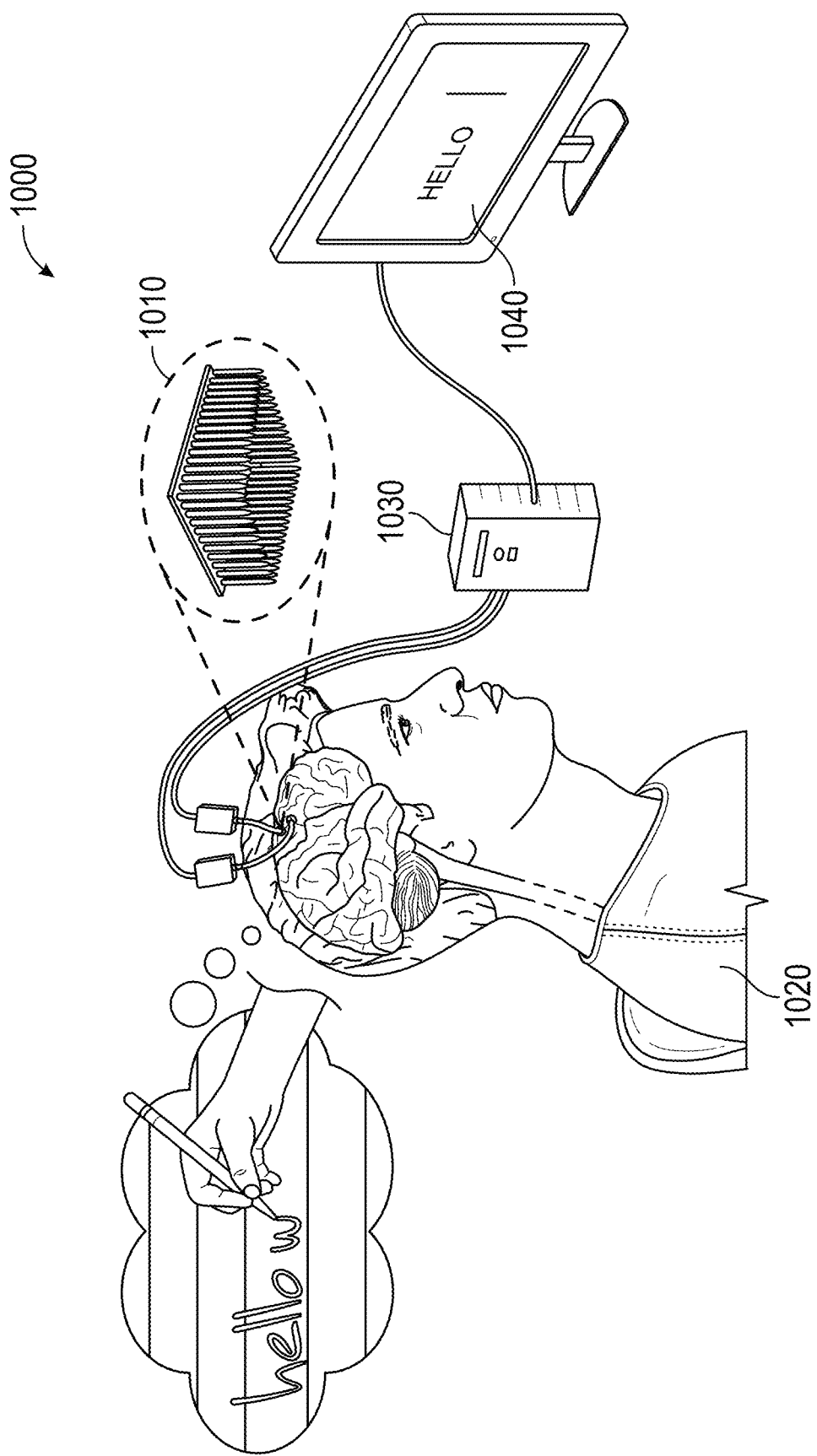
FIG. 10 illustrates an example neural recording and data processing system.

In this respect, FIG. 10 illustrates neural recording and data processing system 1000. The example system 1000 includes neural recording sensors 1010 to measure neural signals (e.g., voltages) within the subject 1020. The measured neural signals may then be processed by the computer 1030, to determine information to display on the display 1040. In the illustrated example, the subject 1020 is "thinking" of writing the word "hello," and thus, via the signals measured by the sensors 1010, the computer 1030 is able to determine to display the word "hello" on the display 1040. However, any type of information may be displayed on the display 1040. For example, the display 1040 may simply display what voltages or signals are being received by the sensors 1010. In another example, the display may display other information of the subject determined from the signals (e.g., the subject is sleeping, awake, etc.).

In addition, although the example of FIG. 10 illustrates a wired connection between the sensors 1010 and the computer 1030, the connection may instead be wireless via any suitable wireless technique.

Moreover, known electronic recording methods are generally power- and space-limited; and both of these factors constrain the number and quality of recording channels. The techniques disclosed herein solve these problems and others.

The considerations for neural recording are different than the considerations for measuring grid-level voltages. In the neural recording applications, the temperature required range is very narrow, as the human body tightly regulates its own temperature to within ~1-2° C. normal core body temperature (37° C.). The voltages involved are also very small (~μV-mV scale), so linearity in practice is a given. In this case, the device should be optimized for an extremely low power dissipation per unit noise bandwidth ($E_Q$), so as not to increase the temperature of the surrounding tissue, at the expense of linearity and temperature sensitivity. Some embodiments do this in one of either two ways: (1) modifying the material to have a high $d_{33}$ and/or $r_{33}$, which increases the overall system gain β; or (2) adding mirrors on either side of the active piezoelectric material, which increases the Q-factor of the device and hence the overall gain (β).

The device should also be made much smaller (~20 μm diameter instead of ~2 mm) in order to minimize invasiveness in the body. For the material, some embodiments use either barium titanate (BTO) or potassium sodium niobate (KNN), although any ferroelectric material with high $d_{33}$ may be used (bismuth ferrite (BFO), zirconate titanate (PZT), etc.). Regarding the mirrors, some implementations fabricate Distributed Bragg reflectors using alternating layers of $SiO_2$ and amorphous Si using plasma enhanced chemical vapor deposition (PECVD). Any deposition process (sputtering, CVD, evaporation, etc.) may be used for this and any alternating set of materials with different refractive indices may be used. If the mirror is conductive, this will work as-is. If it is not conductive (as is the case with the embodiments using Bragg mirrors), additional transparent electrodes should be deposited sandwiching the active piezoelectric layer prior to depositing the mirrors.

Figure 11:
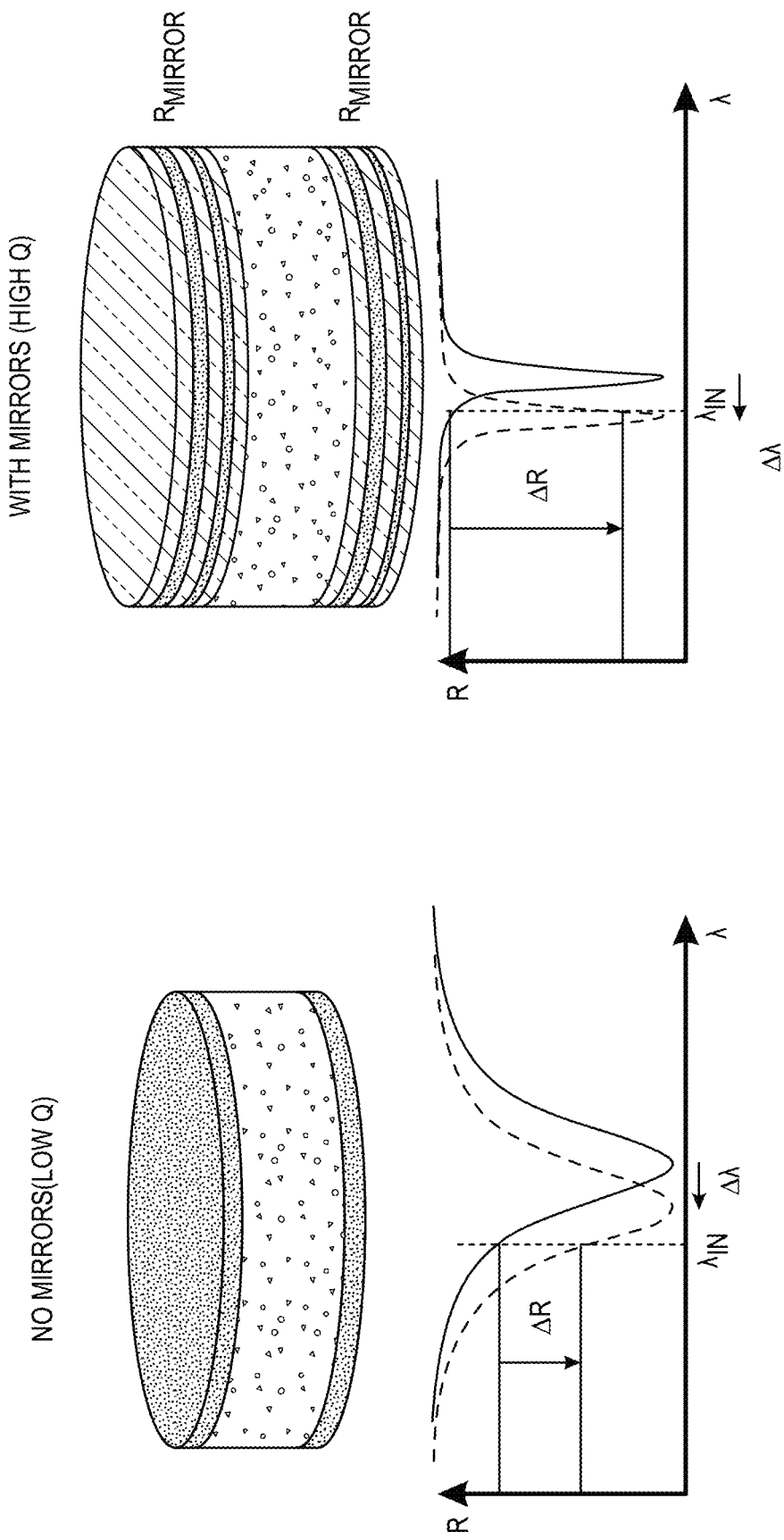
FIG. 11 illustrates an example of how adding mirrors changes the reflectance curve.

FIG. 11 illustrates an example of how adding mirrors changes the reflectance curves. As mentioned above, adding mirrors on either side of the active piezoelectric material increases the Q-factor of the device and hence the overall gain (β). This is because the mirrors "isolate" the optical system, thus minimizing the optical leakage, and thus increasing Q. In this regard, in some embodiments, the Q-factor changes as:

$$Q \approx \frac{\pi}{1 - R_{mirror}} \quad (23)$$

Figure 12:
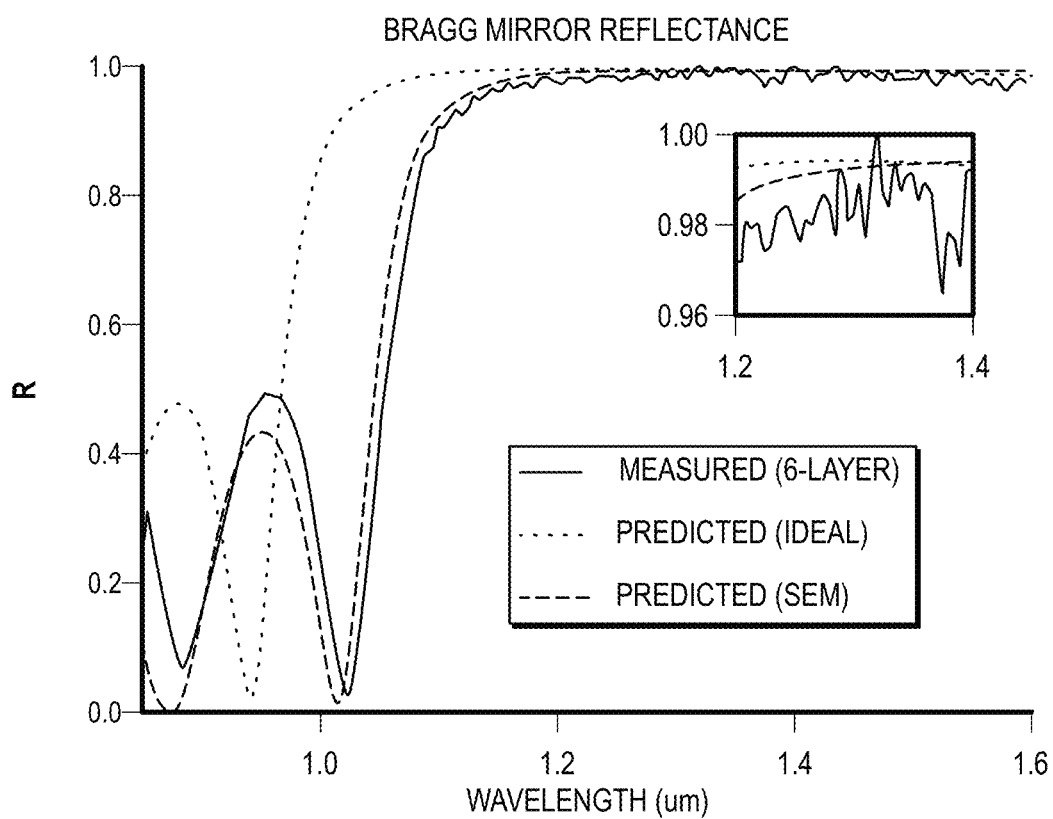
FIG. 12 shows reflectance vs. wavelength in an example including a 3-layer Bragg mirror.

In one example, a 3-layer Bragg mirror was used, which achieved a reflectance of ~0.985 (uncertainty 0.01). The reflectance vs. wavelength is shown in FIG. 12.

In some embodiments, the mirrors include through-hoes (e.g., vias) to allow contact between electrodes sandwiching a mirror layer. In this regard, a material filling the through-holes may be the same material as the electrodes on top and on bottom of the mirror layer.

The fabrication process for the neural recording embodiments often is more complex than for the embodiments which measure grid level voltages. For example, for the neural recording embodiments, the fabrication process involves film transfer via wafer bonding after deposition of the first electrode/mirror pair, and then deposition of the second electrode/mirror pair.

Figure 13:
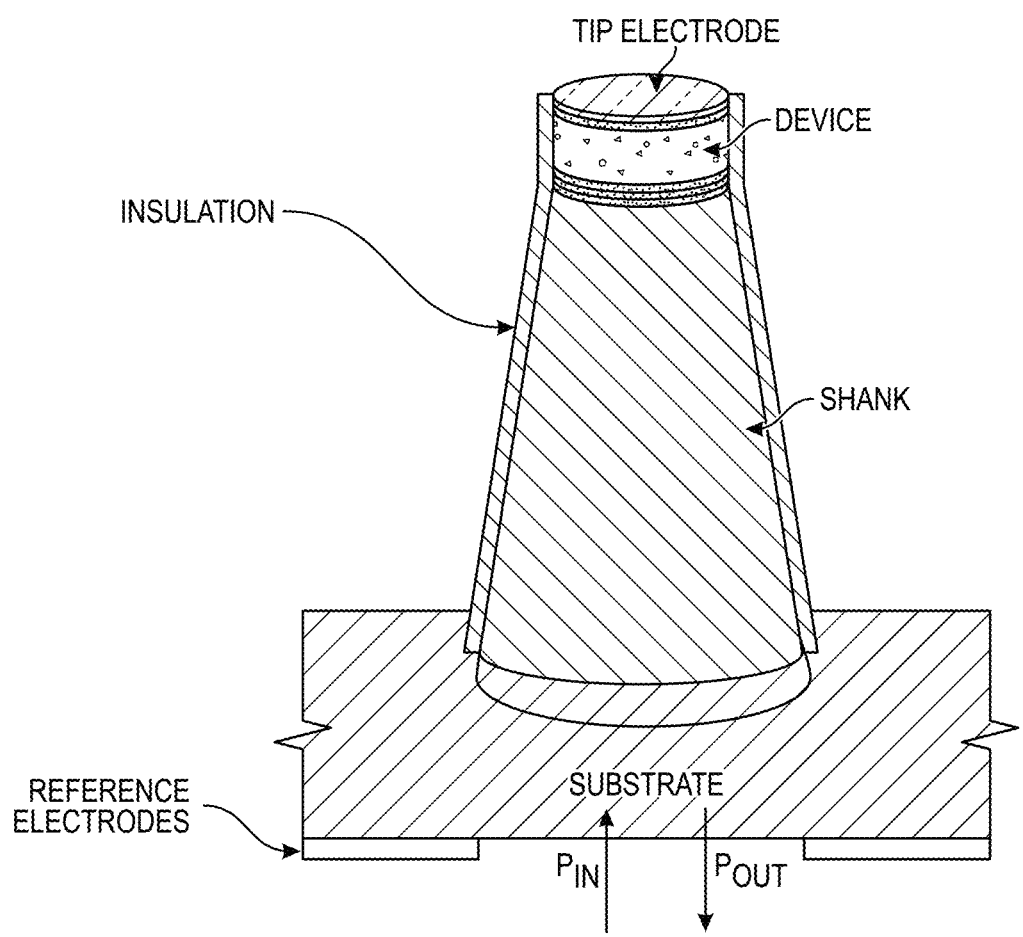
FIG. 13 illustrates an example embodiment including a shank.

In addition, in some embodiments, following fabrication of the neural recording device, a shank may be created via a deep etch, as illustrated in FIG. 13.

The theory of operation in both the neural recording embodiments and the grid voltage measuring embodiments is the same, as a shift in the resonant frequency due to an applied voltage causes a change in the device reflectance and hence measured photocurrent. The interrogation scheme is reflective in the neural recording embodiments, as only reflected intensity can be measured, and thus some embodiments involve focusing optics and an external imaging/aberration correction system.

Example Fabrication of Mirror Layers

Mirror Layer Optimization

To allow for arbitrarily thick mirrors to be deposited, there are at least three possible concerns. First, excess stress can cause failure of films, especially α-Si, which experiments of this disclosure have revealed to be particularly temperamental and prone to high stress. High stress also may cause warping of the underlying substrate, which restricts the equipment that can be subsequently used, particularly the lithography stepper. Second, film roughness causes degradation of mirror reflectivity, and often increases with an increasing number of layers. Third, the films should have low optical absorption near a wavelength of interest. Due to time- and resource-constraints, the experiments disclosed herein did not optimize for low absorption, but primarily for low stress and roughness.

To optimize the $SiO_2$ film, some embodiments use a plasma enhanced chemical vapor deposition (PECVD) tool. Some such PECVD tools can provide variable silane, $N_2O$, and Ar flow, and can vary the temperature, pressure, and RF power to the plasma. Some implementations use parameters that sustain a plasma and be feasibly controlled by the tool, shown in Table 1.

TABLE 1

Factor ranges chosen for statistically designed experiment for SiO$_2$ deposition

| | |
|---|---|
| Silane flow (sccm) | 5-50 |
| N$_2$O flow (sccm) | 400-1000 |
| Ar Flow (sccm) | 0-200 |
| Temperature (C.) | 200-350 |
| Pressure (mtorr) | 600-1500 |
| Power (W) | 15-50 |

One aspect included a 17-run definitive screening experiment, which advantageously allowed to run whole cassettes of wafers without much difficulty. This experimental design further allowed for quadratic effects to be estimated and provided slight confounding of two-factor interactions. This experiment was generated using statistical software that ensured run order randomization and running two additional center points. All films were deposited for 21 minutes on bare Si wafers. The thickness was measured using a reflectometer, and stress was measured using an optical interferometer for wafer bow measurement. The films had measured thicknesses between 250 nm and 2900 nm, stresses between −4 and −530 MPa, and roughnesses between 0.16 and 9.16 nm rms. A film was chosen which had both excellent roughness (0.8 nm rms for a 1700 nm thick film) and reasonable stress (−250 MPa), which had the process parameters shown in the following Table 2.

TABLE 2

Process parameters for optimal SiO$_2$ deposition

| | |
|---|---|
| Silane flow (sccm) | 50 |
| N$_2$O flow (sccm) | 700 |
| Ar Flow (sccm) | 200 |
| Temperature (C.) | 350 |
| Pressure (mtorr) | 600 |
| Power (W) | 15 |

To optimize the α-Si film, the same PECVD tool was used as for SiO$_2$ deposition. The factors and ranges shown in Table 3 were also used. One aspect started with thermally oxidized Si wafers, as these films were to be deposited on top of SiO$_2$. Deposition onto bare Si was found to yield bizarre formation of large (>200 μm) spherical mounds on the surface, which did not occur with deposition onto SiO$_2$.

TABLE 3

Factor ranges chosen for statistically designed experiment for α − Si deposition

| | |
|---|---|
| Silane flow (sccm) | 5-50 |
| H$_2$ flow (sccm) | 0-100 |
| Ar Flow (sccm) | 0-500 |
| Temperature (C.) | 200-350 |
| Pressure (mtorr) | 600-1500 |
| Power (W) | 10-50 |

One aspect designed a similar 17-run experiment for α-Si optimization, but was terminated after 9 runs, as an acceptable film was found at 9 runs. All films were deposited for 21 minutes on bare Si wafers. The thickness was measured using a reflectometer, and stress was measured using a optical interferometer for wafer bow measurement. The films had roughnesses between 0.5 and 3.4 nm rms, stress between −200 and −1900 MPa, and thicknesses between 30 and 101 nm. The best film of these had a stress of −200 MPa and a roughness of 0.7 nm rms, which had the process parameters listed in Table 4. Conveniently, the temperature was the same as for the SiO$_2$, allowing to avoid temperature ramping between layers, a time-consuming process.

TABLE 4

Process parameters for optimal α − Si deposition

| | |
|---|---|
| Silane flow (sccm) | 5 |
| H$_2$ flow (sccm) | 0 |
| Ar Flow (sccm) | 500 |
| Temperature (C.) | 350 |
| Pressure (mtorr) | 600 |
| Power (W) | 10 |

Once these mirror layers were optimized, they were sent out for optical characterization of refractive index in the range of 600 nm-1700 nm.

Step 1: ARC, Mirror Deposition

On some wafers, an ARC was deposited consisting of 50 nm of sputtered Ti followed by 260 nm of CVD α-Si, using the same recipe discussed above. After that layer, a 9-layer stack was deposited as the bottom mirror, starting and ending with SiO$_2$ layers. The target thickness for the SiO$_2$ layers was 240 nm, and the target thickness for the α-Si was 90 nm. The deposited 9-layer mirror had a total roughness of 0.8 nm rms, similar to what was expected from the films themselves.

Figure 14:
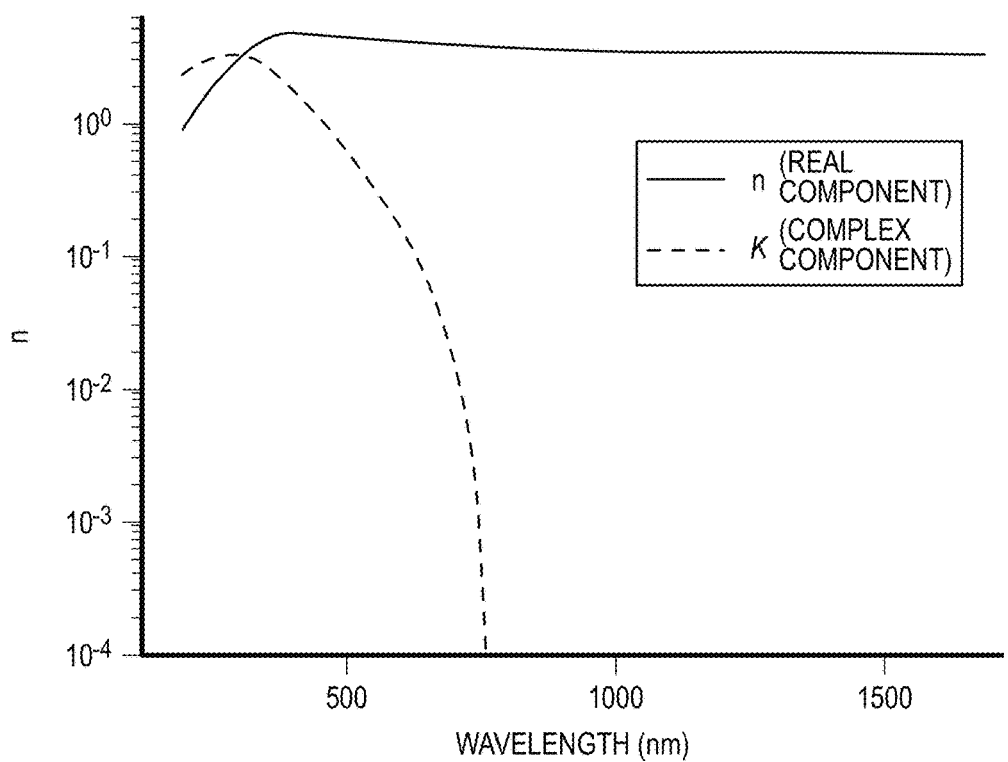
FIG. 14 shows an exemplary α-Si complex refractive index from 250 nm-1700 nm, deposited on Fused Silica substrate.

FIG. 14 shows an exemplary α-Si complex refractive index from 250 nm-1700 nm, deposited on Fused Silica substrate. Complex index at 1300 nm is 3.61+0i.

Figure 15:
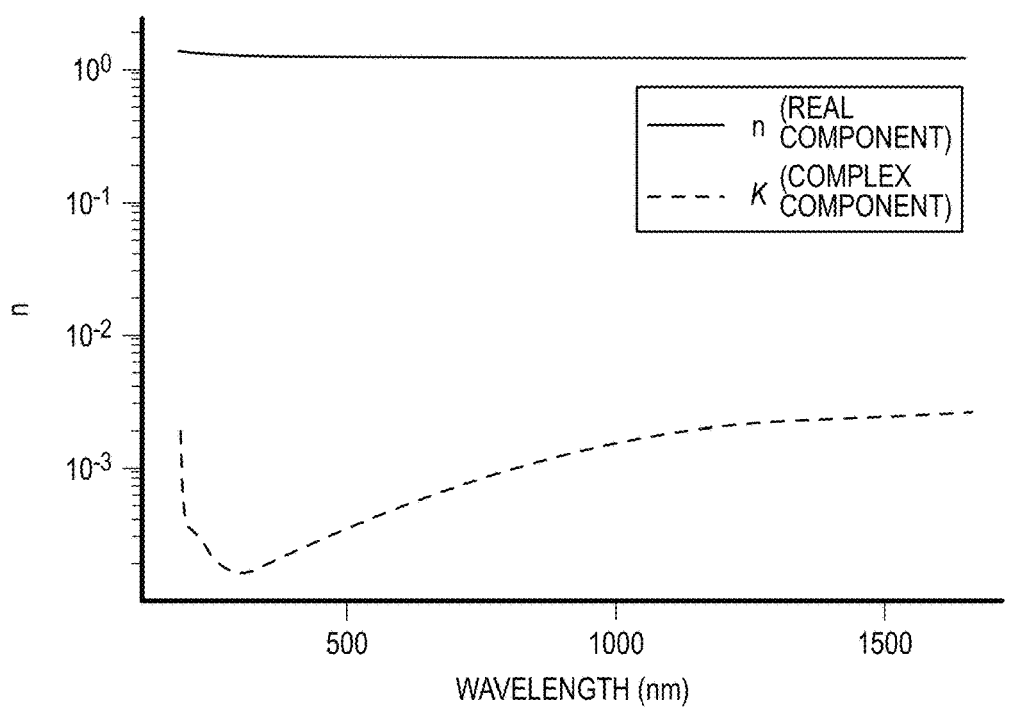
FIG. 15 shows $SiO_2$ complex refractive index from 250 nm-1700 nm deposited on Fused Silica substrate.

FIG. 15 shows SiO$_2$ complex refractive index from 250 nm-1700 nm deposited on Fused Silica substrate. Complex index at 1300 nm is 1.47+0.0016 i.

Step 2: AlN Sputtering

Some aspects used previously-developed process recipes for sputtering aluminum nitride. Some aspects used a reactive sputter tool having a conical aluminum target and capable of flowing N$_2$ gas during deposition. Some aspects used 7 sccm of Ar and 22 sccm of N$_2$ with 4.5 kW of DC power, typically for 350-450s. The typical deposition voltage was 395-401V.

Prior to deposition, for each wafer, some aspects also ran a conditioning wafer which first cleaned the target for 100s with 4 kW of power and 6 sccm of Ar gas, followed by a brief 30s target poison using 4.5 kW of power, 22 sccm N2/7 sccm Ar. As the thickness of this layer may change the device resonant wavelength, some aspects ran pre- and post-thickness monitor wafers to ensure the deposition thickness was within spec, and calibrate the depositing time and potential deposition rate drift.

Step 3: Top Mirror Deposition

To deposit the topside mirror, some aspects used the same process as in step 1.

Step 4: Al/W Sputtering

To form a backside contact to p-Si, some aspects use aluminum, as this works well to create ohmic contacts with p-Si. However, after deposition of the mirrors and AlN layers, the wafer was highly bowed, typically between 60 and 90 μm. This posed a challenge for the lithography stepper, which can only tolerate bows <50 μm. To compensate for this, after depositing 10 nm of Al to form the contact, an additional 100 nm of tungsten was deposited to de-bow the wafer. Some aspects chose tungsten, as it can tolerate large stresses before film failure, and as-deposited was highly stressy (~1-1.4 GPa). This reduced the wafer bow to ~30 μm to allow for subsequent lithography.

Step 5: SiO$_2$/α-Si/AlN Etching

To isolate individual "devices," some aspects patterned circular mesas using 2.5 μm of UV26 negative resist, exposed at 35 mJ/cm$^2$ in the DUV lithography stepper, and developed with a 130° C. post-exposure bake and 45 seconds of soak time in MF-26A. The resist was then hard baked at 120° C. for 30 minutes.

To etch through the topside mirror, some embodiments alternated between using an inductively coupled plasma oxide etcher and a transformer-coupled plasma etcher. In some examples, each SiO$_1$ layer etch ran for 80 seconds with a strike pressure of 10 mtorr, a process pressure of 4 mtorr, with C$_4$F$_8$/H$_2$/He flow of 15/8/174 sccm, a coil power of 1500 W, and a bias power of 350 W at 13.56 MHz. The α-Si etch ran for 30 seconds with a TCP RF power of 300 W, a bias power of 150 W, Cl$_2$/HBr flows of 50/150 sccm at a pressure of 12 mtorr.

Some embodiments alternated between the two different etchers until the underlying AlN layer was reached. To confirm the final oxide layer had been breached, a small drop of MF-26A developer was applied to the surface, and it was confirmed that it etched the AlN.

To etch through the AlN, some aspects etched the AlN in a dedicated aluminum etch chamber using a Cl$_2$ based etch. Some aspects used a plasma power of 800 W, a bias power of 85 W, a pressure of 5 mtorr. Some aspects used the gases Cl$_2$/H$_2$/Ar/BCl$_3$ sat flows of 50/50/70/5 sccm for 240 seconds. Some aspects used the same MF-26A spot test to confirm that the AlN was fully cleared across the wafer.

Once the AlN was cleared, the remaining photoresist was removed using a 1 kW oxygen plasma.

Step 6: ITO Sputtering, Patterning

To form the top device contact, some aspects sputtered 60 nm of ITO using a multi-target co-sputtering system. The system used a 3" ITO target with a process pressure of 3 mtorr, Ar flow of 200 sccm, and target power of 100 W. In some aspects, no process optimization was attempted. Some aspects sent out a thick film of ITO for optical constant characterization.

To pattern the ITO, some aspects spun on 2.5 μm of UV26 negative resist, exposed in the DUV lithography stepper, developed with a post-exposure bake of 130° C. and an MF-26A soak of 45 seconds, and hard-baked at 120° C. for 30 minutes. Some aspects then ion milled the ITO at 30 degrees for 5 minutes at 500V/250 mA, followed by a 70-degree polish for 1 minute. Some aspects targeted an over-etch of 50% to ensure the ITO was fully cleared. After the ion mill, some aspects used a probe station to confirm the layer was non-conductive, and removed the resist with a heated soak in NMP heated to 80° C.

Figure 16:
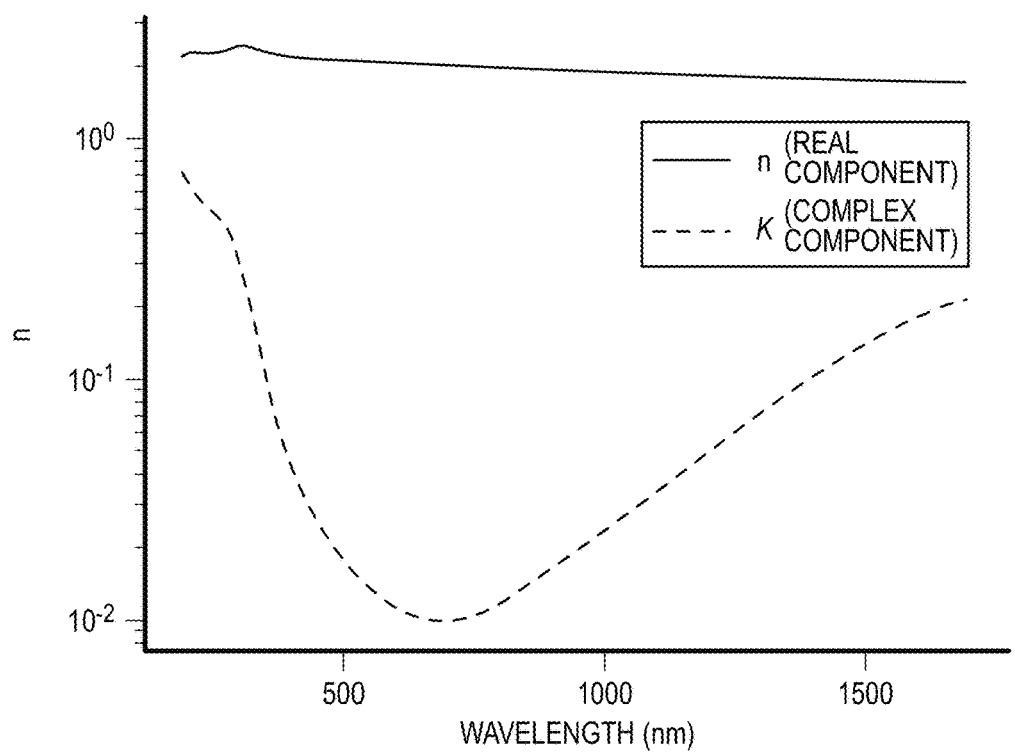
FIG. 16 shows an example ITO complex refractive index from 250 nm-1700 nm.

FIG. 16 shows an example ITO complex refractive index from 250 nm-1700 nm. In the illustrated example, the complex index at 1300 nm is 1.78+0.071 i.

Step 7: Al Evaporation, Liftoff, Dicing

To make contacts to the devices, some aspects used aluminum deposited using a liftoff process. First, 1 μm of LoR-5A resist was deposited, followed by 0.87 μm of UV-210 negative resist. The resist was patterned in the ASML stepper used previously, and developed with a 130° C. post-exposure bake using 45 seconds of MF-26A. Some aspects then evaporated 300 nm of Al and performed a gentle liftoff (as the adhesion to the underlying ITO was poor) by soaking in NMP at 80° C. for 30 minutes. Some aspects then coated the wafers in 2 μm of i-line resist to protect during dicing, diced 5 mm×5 mm square chips, and rinsed them in acetone to remove the protective resist. Some aspects made electrical contact to the substrate by bonding each die to a printed circuit board with printed epoxy, and the top of each die by wirebonding to bond pads.

Resonance Tuning

Due to the nature of nanofabrication, it may be difficult to control film thicknesses across the same wafer and wafer-to-wafer. In practice, with the AlN deposition tool, it is possible to achieve <1% within-wafer thickness variation with 1-2% wafer-to-wafer thickness variation. This 1% change in the piezoelectric layer thickness corresponds to a ~13 nm shift in resonant wavelength, which means the laser source must be tunable to within the uncertainty of the piezoelectric layer thickness. While this device is more sensitive to changes in the piezoelectric layer thickness, changing the Bragg mirror layer thicknesses changes the phase of the mirror and also shifts the resonant frequency.

Device Reflectance Model

To calculate the reflectance spectra of some devices, some aspects used a custom-built python module rcwa, available on the python package index, using the script theory_reflectance.py. This module implements the Transfer Matrix Method, which models stacks of thin films which are uniform and infinite along x- and y-, and finite or semi-infinite along z. For the simulation setup, some aspects used layer thicknesses and refractive indices according to those in Table 5. Since the index of the α-Si did not vary substantially over the simulation domain, some aspects used a constant refractive index. Somewhat surprisingly, the imaginary part of the SiO$_2$ index of <0.0002 fit the measured data better than the much higher values. This may be due to the different substrates on which the SiO$_2$ was deposited (fused silica for characterization purposes and AlN/α-Si for the Bragg mirrors).

Figure 17:
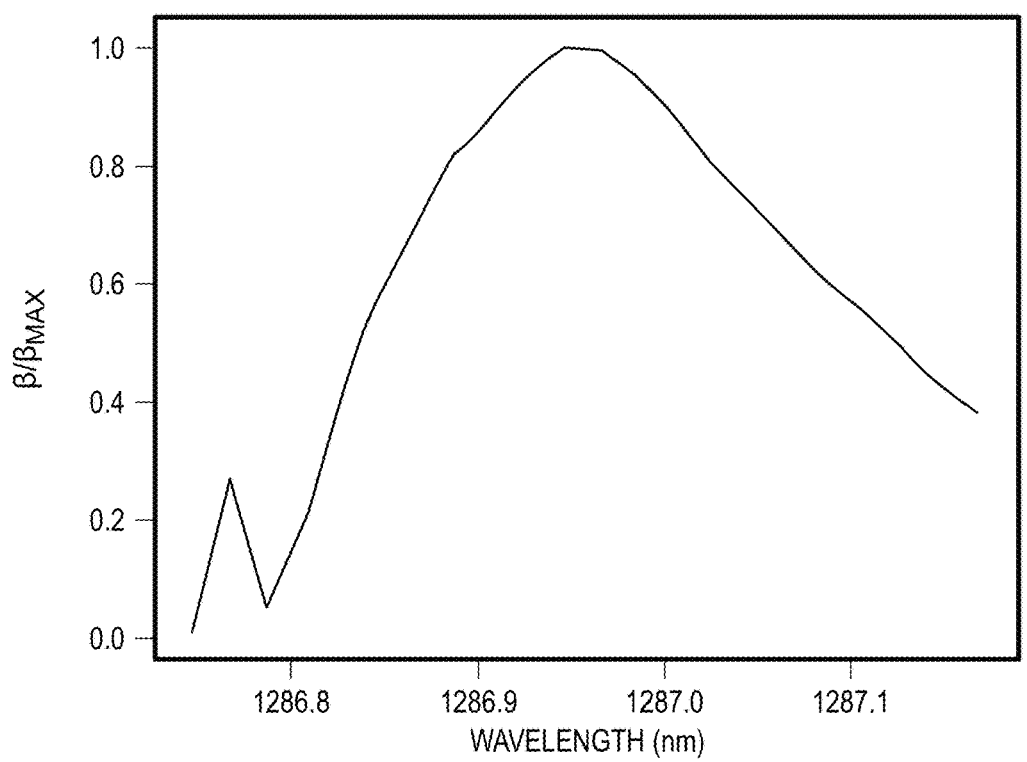
FIG. 17 shows an example measured gain vs. wavelength near the optimal off-resonance location.

FIG. 17 shows an example measured gain vs. wavelength near the optimal off-resonance location. For this example, the optimal wavelength corresponds to 1287.0 nm.

TABLE 5 shows the exemplary parameters used in the calculation of sensor gain and reflectance for analytical model and TMM model

| Symbol | Description | Value |
| --- | --- | --- |
| $r_{33}$ | Pockels Coefficient | 1 pm/V |
| $d_{33}$ | Piezoelectric Coefficient | 5 pm/V |
| $R_{max}$ | Maximum Reflectance dip | 0.5 |
| Q | Q-factor | 2900 |
| $\epsilon_{r,ox}$ | Oxide relative permittivity | 3.9 |
| $\epsilon_{r,\alpha-Si}$ | Amorphous Si relative permittivity | 11.4 |
| $\epsilon_{r,AlN}$ | AlN relative permittivity | 8.5 |
| $t_{\alpha-Si}$ | Amorphous Si layer thickness | 90 nm |
| $t_{SiO2}$ | SiO$_2$ layer thickness | 210 nm |
| $t_{AlN}$ | AlN layer thickness | 310 nm |
| $N_{SiO2}$ | Number of SiO$_2$ layers in single mirror | 5 |
| $N_{\alpha-Si}$ | Number of α − Si layers in single mirror | 4 |
| $n_{AlN}$ | AlN Refractive Index | 2.13 |
| $n_{SiO2}$ | SiO$_2$ refractive index | 1.47 |
| $n_{\alpha-Si}$ | α − Si refractive index | 3.61 |
| $n_{ITO}$ | ITO refractive index | Data table |

Device Gain

As described above, the change in device reflectance can be expressed as:

$$\Delta R = \beta V_{in}$$

Where β is given by:

$$\beta = \frac{3\sqrt{3}}{4} \frac{R_{max}Q}{t}\left(d_{33} + \frac{1}{2}n_0^2 r_{33}\right)$$

Where each of these parameters is described in Table 5.

However, this is in terms of the voltage across the piezoelectric layer, but in some aspects, there may also be capacitive division across the mirrors. To obtain the voltage across the piezoelectric layer from the voltage across the entire device, one may use capacitive division:

$$v_{active} = \alpha v_{in}$$

where $$\alpha = \frac{C_{mirror}/2}{C_{active} + C_{mirror}/2}$$

Where $C_{mirror}$ is the capacitance of a single one of the Bragg mirrors and $C_{AlN}$ is the capacitance of the AlN layer.

$$C_{mirror} = \frac{1}{N_{SiO2}/C_{SiO2} + N_{\alpha-Si}/C_{Si}}$$

Using this, the revised complete gain expression is below:

$$\beta = \alpha * \frac{3\sqrt{3}}{4} \frac{R_{max}Q}{t}\left(d_{33} + \frac{1}{2}n_0^2 r_{33}\right)$$

The parameters used to find the gain are found in Table 5. The calculated parameters are found in Table 6.

Figure 18:
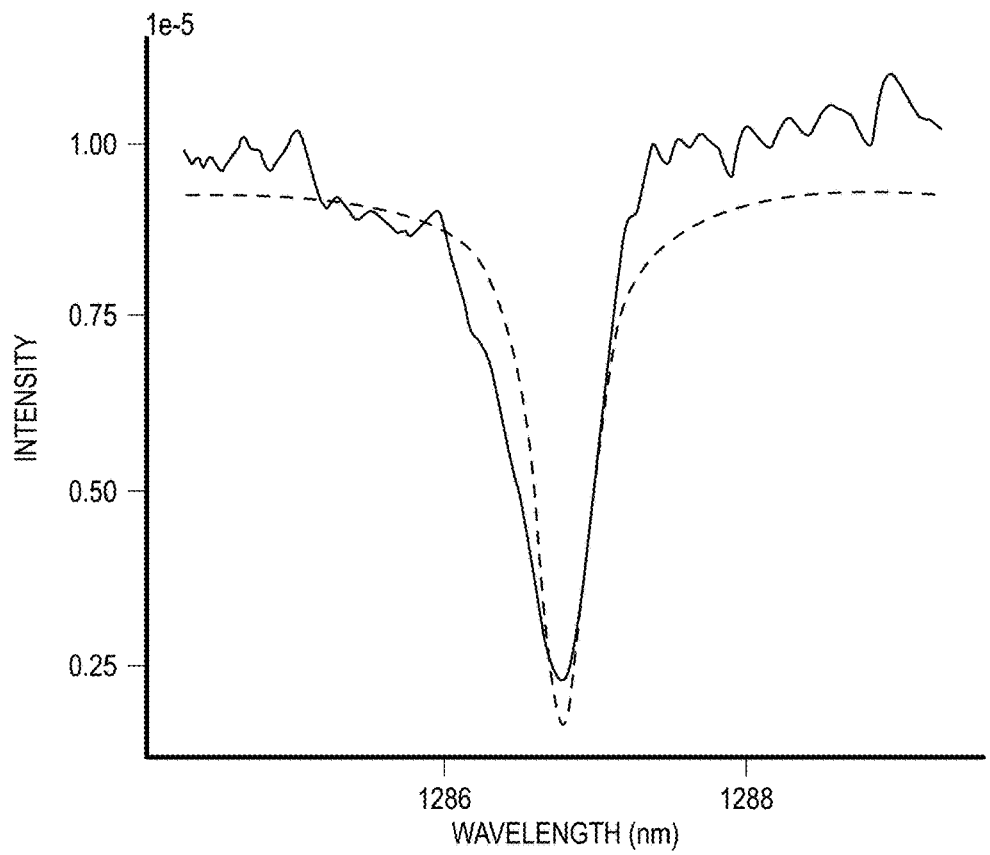
FIG. 18 shows example raw laser power near resonance vs. wavelength (solid) and fitted Lorentzian function with Q=2900 (dashed).

FIG. 18 shows example raw laser power near resonance vs. wavelength (solid) and fitted Lorentzian function with Q=2900 (dashed).

TABLE 6

Parameters used in the calculation of sensor gain for analytical model and TMM model

| Symbol | Description | Value |
| --- | --- | --- |
| $C_{SiO2}$ | Oxide layer capacitance density | 164 pF/mm$^2$ |
| $C_{\alpha-Si}$ | Amorphous Si capacitance density | 1120 pF/mm$^2$ |
| $C_{mirror}$ | Mirror capacitance density | 22.4 pF/mm$^2$ |
| $C_{AlN}$ | AlN capacitance density | 243 pF/mm$^2$ |
| $\alpha$ | Capacitive division factor | 0.057 |
| $\beta_0$ | Unmodified gain | 3.2 * 10$^{-2}$V$^{-1}$ |
| $\beta$ | Modified gain | 2.5 * 10$^{-3}$ |

Figure 19:
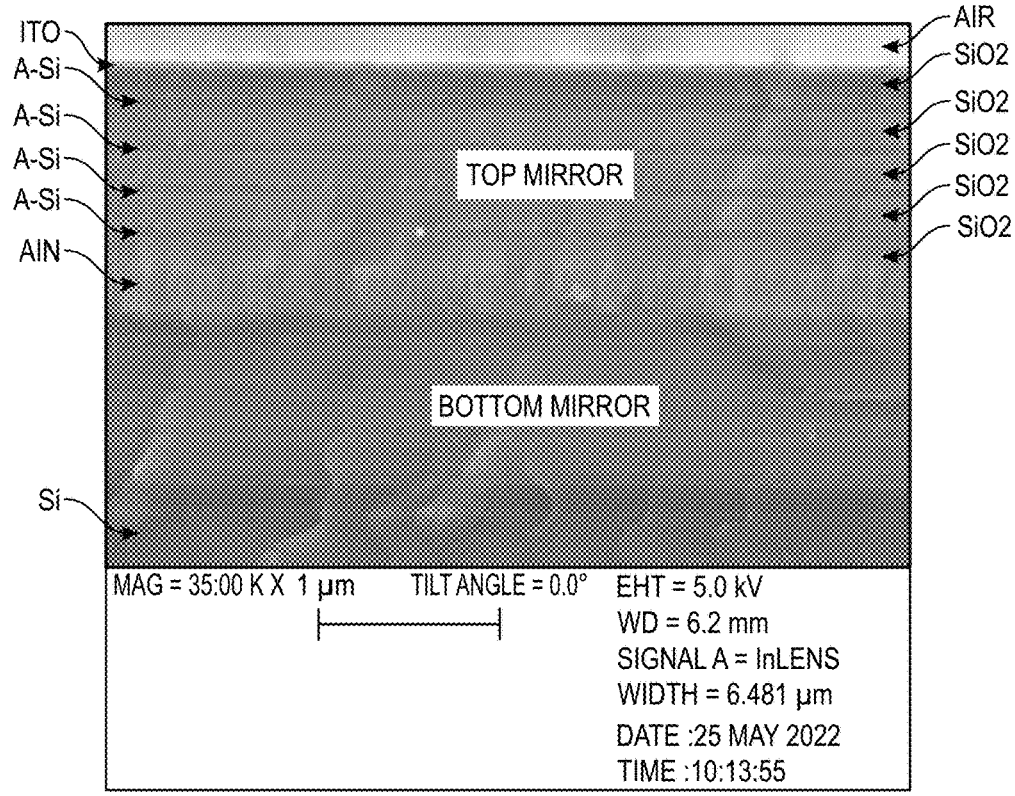
FIG. 19 shows an example cross-sectional Scanning Electron Microscope (SEM) of film stack of a device wafer without an anti-reflection coating (ARC).

FIG. 19 shows an example cross-sectional SEM of film stack of a device wafer without ARC. In the illustrated example, the approximate thicknesses of the layers are as follows: ITO: 60 nm, SiO$_2$: 240 nm (mean, top) and 240 nm (mean, bottom), ($\alpha$-Si): 100 nm (mean, top) and 100 nm (mean, bottom), AlN: 330 nm.

Figure 20:
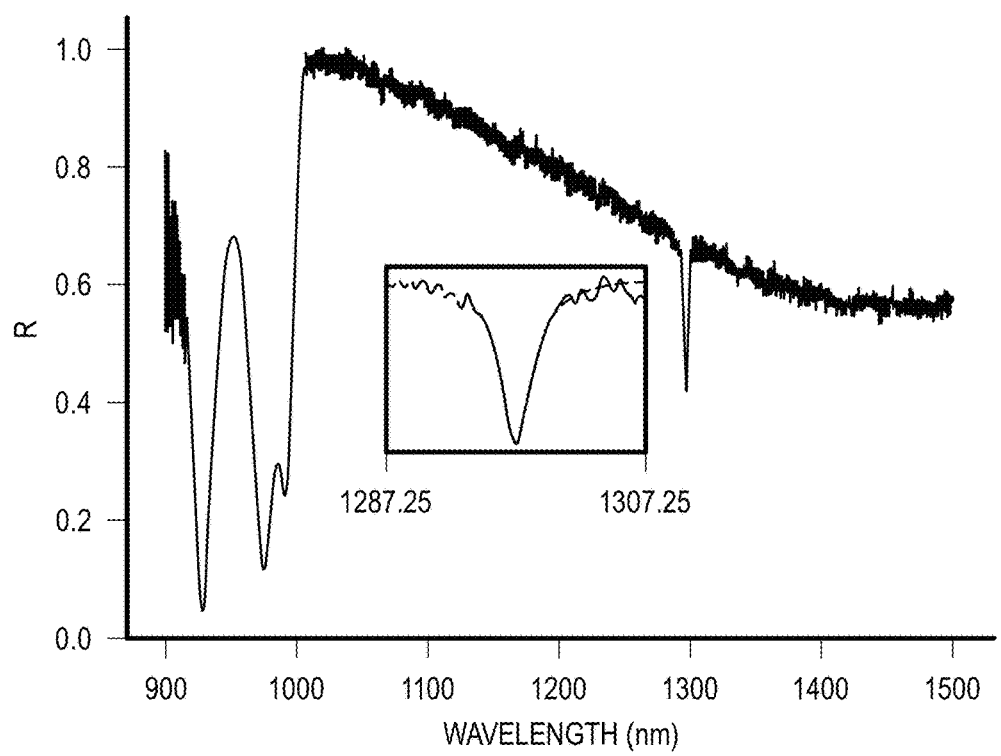
FIG. 20 shows an example reflectance of planar film without ARC.

FIG. 20 shows an example reflectance of planar film without ARC. In the illustrated example, the peak is broader (best-fit Q is 430), and has a shallower depth compared to with ARC coating.

Figure 21:
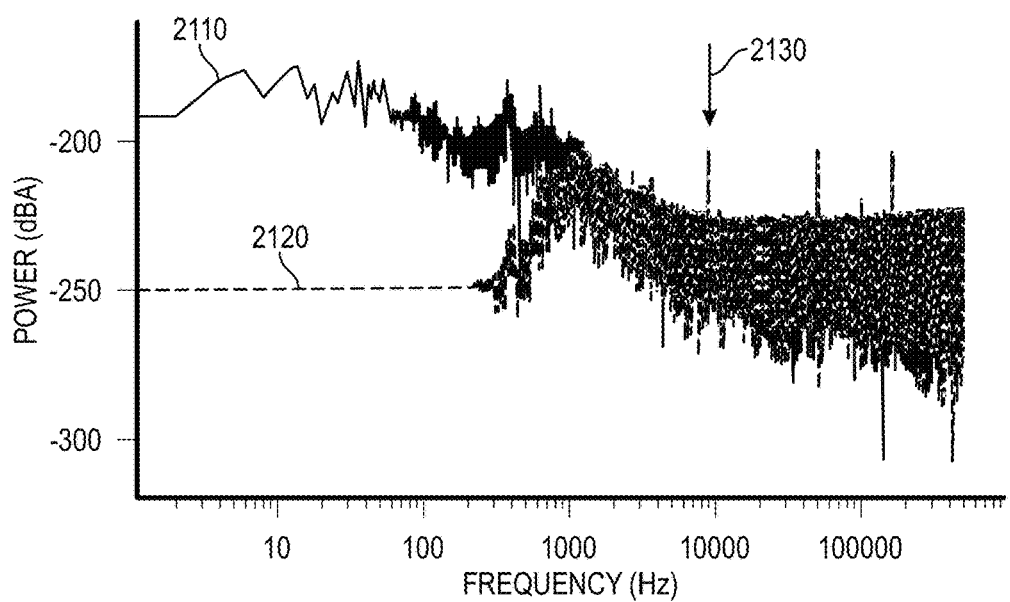
FIG. 21 shows an example, typical power spectral density of unfiltered data and 1 kHz highpass-filtered data.

FIG. 21 shows an example, typical power spectral density of unfiltered data 2110 and 1 kHz highpass-filtered data 2120. In the illustrated example, arrow 2130 indicates location of input sinusoid, which, in this plot, had a 10 mV input amplitude.

Neural Recording—Example Digital Communication Embodiments

Some of the neural recording embodiments also involve digital communication. In this regard, it should be understood that existing devices for optical communication either are not CMOS (complementary metal-oxide semiconductor) compatible, require large bias voltages to operate, or consume substantial amounts of power. Advantageously, the following presents a high-Q CMOS-compatible electro optic modulator that enables establishing an optical data uplink to implants. The modulator acts as a pF-scale capacitor, requires no bias voltage, and operates at CMOS voltages of down to 0.5V. This technology may provide a path towards the realization of millimeter (mm)- and sub-mm scale wireless implants for use in bio-sensing applications.

It is known in the bioelectronics field that reducing the size of wireless medical implants provides certain advantages, such as minimizing immediate tissue damage, minimizing long-term impact on surrounding tissue, and easing subsequent removal of the implant.

Most existing implantable wireless systems use radio frequency (RF) electromagnetic (EM) waves in the GHz frequency range to transfer power to and data from the implant [W. Biederman, D. J. Yeager, N. Narevsky, A. C. Koralek, J. M. Carmena, E. Alon, and J. M. Rabaey, "A fully-integrated, miniaturized (0.125 mm$^2$) 10.5 µw wireless neural sensor," IEEE J. Solid-State Circuits 48, 960-970 (2013); Lee, V. Leung, A.-H. Lee, J. Huang, P. Asbeck, P. P. Mercier, S. Shellhammer, L. Larson, F. Laiwalla, and A. Nurmikko, "Neural recording and stimulation using wireless networks of microimplants," Nat. Electron. 4, 604-614 (2021)]. However, coupling these EM waves through an RF coil (antenna) to sub-mm implants can be severely inefficient [M. L. Wang, S. Baltsavias, T. C. Chang, M. J. Weber, J. Charthad, and A. Arbabian, "Wireless data links for next-generation networked micro-implantables," in 2018 IEEE Custom Integrated Circuits Conference (CICC), (2018), pp. 1-9]. This arises because GHz EM waves experience high attenuation in tissue [J. Thimot and K. L. Shepard, "Bioelectronic devices: Wirelessly powered implants," Nat. Biomed. Eng. 1, 0051 (2017)], and the miniaturization of the RF antennas to sub-mm scales results in a small coil impedance, making it challenging to harvest enough RF energy to power up the implant [A. Khalifa, Y. Liu, Y. Karimi, Q. Wang, A. Eisape, M. Stanaćević, N. Thakor, Z. Bao, and R. Etienne-Cummings, "The microbead: A 0.009 mm3 implantable wireless neural stimulator," IEEE Transactions on Biomed. Circuits Syst. 13, 971-985 (2019)]. Ultrasound waves with sub-mm wavelengths have recently gained attention, as they enable comparatively more efficient coupling to mm-scale implants placed deep in tissue implants [D. K. Piech, B. C. Johnson, K. Shen, M. M. Ghanbari, K. Y. Li, R. M. Neely, J. E. Kay, J. M. Carmena, M. M. Maharbiz, and R. Muller, "A wireless millimetre-scale implantable neural stimulator with ultrasonically powered bidirectional communication," Nat. Biomed. Eng. 4, 207-222 (2020); S. Sonmezoglu, J. R. Fineman, E. Maltepe, and M. M. Maharbiz, "Monitoring deep-tissue oxygenation with a millimeter-scale ultrasonic implant," Nat. Biotechnol. 39, 855-864 (2021)]. However, the miniaturization of ultrasonic implants to sub-mm scales is challenging, and the scaling down of the piezoelectric bulk crystal (antenna) used in ultrasonic implants degrades power transfer efficiency and data transfer reliability of the acoustic link in tissue [T. C. Chang, M. J. Weber, J. Charthad, S. Baltsavias, and A. Arbabian, "End-to-end design of efficient ultrasonic power links for scaling towards submillimeter implantable receivers," IEEE Transactions on Biomed. Circuits Syst. 12, 1100-1111 (2018); S. Sonmezoglu, A. Darvishian, K. Shen, M. J. Bustamante, A. Kandala, and M. M. Maharbiz, "A method and analysis to enable efficient piezoelectric transducer-based ultrasonic power and data links for miniaturized implantable medical devices," IEEE Transactions on Ultrason. Ferroelectr. Freq. Control. 68, 3362-3370 (2021)]. Light, on the other hand, is potentially attractive for communicating with wireless implants at the sub-mm or even µm scales given the comparably short wavelengths (sub-µm and µm scale), enabling efficient coupling and the efficient conversion of light to electrical energy through a semiconductor photovoltaic cell is possible [S. Ayazian and A. Hassibi, "Delivering optical power to subcutaneous implanted devices," in 2011 Annual International Conference of the IEEE Engineering in Medicine and Biology Society, (IEEE, 2011), pp. 2874-2877; A. C. Molnar, S. Lee, A. Cortese, P. McEuen, S. Sadeghi, and S. Ghajari, "Nanoliter-scale autonomous electronics: Advances, challenges, and opportunities," in 2021 IEEE Custom Integrated Circuits Conference (CICC), (IEEE, 2021), pp. 1-6]. In biosensing applications, the wireless optical implants sometimes consist of a sensor and an integrated circuit (IC) incorporating interface electronics, power management, and data communication components [M. Mujeeb-U-Rahman, D. Adalian, C.-F. Chang, and A. Scherer, "Optical power transfer and communication methods for wireless implantable sensing platforms," J. Biomed. Opt. 20, 1-9 (2015); S. Lee, A. J. Cortese, A. P. Gandhi, E. R. Agger, P. L. McEuen, and A. C. Molnar, "A 250 m×57 m microscale opto-electronically transduced electrodes (motes) for neural recording," IEEE Transactions on Biomed. Circuits Syst. 12, 1256-1266 (2018)].

Some aspects of the present disclosure focus specifically on an optical wireless data communication modality to advance the realization of low-power wireless implants with ultrasmall footprints. In practice, uplink data (data emitted by the implant) can be transmitted from the inside to the outside of the body by using SiGe optical modulators or light sources (LEDs or lasers) [M. Mujeeb-U-Rahman, et al.; S. Lee, et al.; P. Chaisakul, V. Vakarin, J. Frigerio, D. Chrastina, G. Isella, L. Vivien, and D. Marris-Morini, "Recent progress on ge/sige quantum well optical modulators, detectors, and emitters for optical interconnects," in Photonics, vol. 6 (MDPI, 2019), p. 24; D. M. Ackermann, B. Smith, X.-F. Wang, K. L. Kilgore, and P. H. Peckham, "Designing the optical interface of a transcutaneous optical telemetry link," IEEE Transactions on Biomed. Eng. 55, 1365-1373 (2008); A. J. Cortese, C. L. Smart, T. Wang, M. F. Reynolds, S. L. Norris, Y. Ji, S. Lee, A. Mok, C. Wu, F. Xia, N. I. Ellis, A. C. Molnar, C. Xu, and P. L. McEuen, "Microscopic sensors using optical wireless integrated circuits," Proc. Natl. Acad. Sci. 117, 9173-9179 (2020)]. However, SiGe modulators require large reverse bias voltages (1-3V), restricting the circuitry that can be used to drive them. Therefore, light sources, including LEDs and lasers, have recently gained popularity for optical data transfer, mainly due to their ease of integration with CMOS IC. However, these light sources require turn-on voltages with specialized drive circuitry to operate and consume substantial amounts of power.

The present disclosure presents a high-Q electro-optic modulator (EOM) based on piezoelectric actuation that is fabricated using standard microfabrication techniques. The above disclosure demonstrates a low-Q optical voltage sensor based on the same operating principle as the EOM for measuring high voltages in the order of tens of volts [see also J. L. Edmunds, S. Sonmezoglu, J. Martens, A. Von Meier, and M. M. Maharbiz, "Optical voltage sensor based on a piezoelectric thin film for grid applications," Opt. Express 29, 33716-33727 (2021)]. As now discussed below, the device may incorporate high-reflectance mirrors on both sides of the piezoelectric film and anti-reflection coating (ARC), thereby enabling high-Q operation and hence operation at small voltage amplitudes. This EOM shows great promise of establishing an optical wireless link to an implant for high-bandwidth uplink data transfer while avoiding the drawbacks of the current optical data transfer methods mentioned above. The EOM was designed to operate at a wavelength of ~1300 nm to minimize light attenuation mainly due to scattering in tissue [Y. Duan and B. Liu, "Recent advances of optical imaging in the second near-infrared window," Adv. materials 30, 1802394 (2018)]. The device may operate as a simple capacitor, eliminating the need for active power consumed by the device to initiate uplink data transfer. In some examples, the device can be heterogeneously integrated with a low-power CMOS IC, required for sensing, energy harvesting, and data communication to achieve extreme implant miniaturization, and be operated at voltages down to 0.5V, compatible with CMOS electronics, with extremely minimal drive circuitry requirements. The device size is demonstrated to be scaled down to micrometers (<100 µm).

Figure 22:
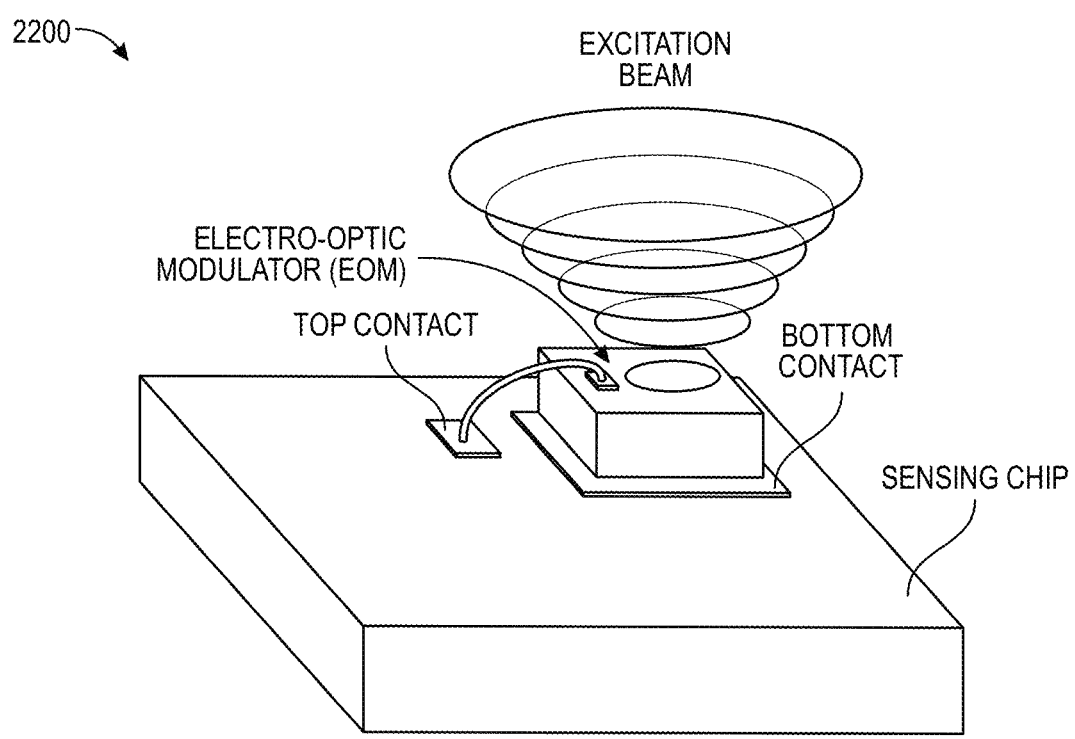
FIG. 22 shows an example integrated sensing system incorporating an electro-optic modulator (EOM).

FIG. 22 shows an example integrated sensing system 2200 incorporating separately-fabricated EOM. In the illustrated example, the excitation beam is coupled into the EOM. The intensity of the beam reflected from the modulator surface can be modulated by the voltage provided by the sensing chip (e.g., a sensor, such as a CMOS sensor) applied between the top and bottom contact. In some embodiments, the sensing chip senses a voltage of a subject (e.g., such as a voltage of a brain of the subject 1020 of FIG. 10), and amplifies the voltage so that the amplified voltage may be read by the EOM. Thus, in some aspects, the EOM optically interrogates the sensing chip. In this regard, the use of the sensing chip enables digital communication.

Design and Fabrication

The electro-optic modulator (EOM) operates as a normal-incidence reflective optical intensity modulator requiring a narrowband tunable light source. In some embodiments, the EOM may be a resonant cavity with a half-wavelength piezoelectric layer sandwiched between two high-reflectance mirrors. In some embodiments, the piezoelectric layer is formed by Aluminum Nitride (AlN), and the mirrors are distributed Bragg reflectors [C. Sheppard, "Approximate calculation of the reflection coefficient from a stratified medium," Pure Appl. Opt. J. Eur. Opt. Soc. Part A 4, 665 (1995)]. The operating principle of the EOM is the same as discussed above with respect to FIG. 1B. When light is incident on this device at its resonance wavelength ($\lambda_r$), the reflected light intensity is at a minimum. Moving away from $\lambda_r$, the intensity increases until it reaches a maximum after roughly a linewidth. By using incident light at a wavelength between these two extremes, a slight shift in the $\lambda_r$ can be made to result in a change in the reflected light intensity.

An applied voltage ($V_{in}$) across the device produces an electric field inside the active AlN layer that causes it to change its thickness, resulting in a shift in the $\lambda_r$ and hence a change in the reflectance (R). In practice, it is easier to work with the relative change in reflectance, $\Delta R$. For the EOM operated at a wavelength ($\lambda_{in}$) where the R slope is the steepest near $\lambda_r$, the modulation depth $\Delta R$ can be approximated by $$\Delta R = \beta V_{in}$$

-continued $$\beta \approx \frac{3\sqrt{3}}{4} \frac{R_{max}Q}{r}\left(d_{33} + \frac{1}{2}n_0^2 r_{33}\right)$$

where $\beta$ is the modulation gain of the device, $R_{max}$ is the amplitude of the resonant dip, Q and t are the device quality factor and piezoelectric layer thickness, and $d_{33}$ is the thickness mode piezoelectric coefficient [see also J. L. Edmunds, S. Sonmezoglu, J. Martens, A. Von Meier, and M. M. Maharbiz, "Optical voltage sensor based on a piezoelectric thin film for grid applications," Opt. Express 29, 33716-33727 (2021)].

The EOM operates without the need of a bias current or voltage, and acts as a simple capacitor. Electrically, the device may contain no active components, does not operate using charged carriers, and is well-modeled as a single capacitor. Any electric field applied within the inner piezoelectric layer may cause it to deform, but this requires no bias current, other than leakage through the layer.

The device was designed to operate at a wavelength of 1310 nm that is a minimally scattering wavelength for transmission through biological tissue. One problem for optical communication through tissue is overcoming absorption and scattering in tissue [R. Horstmeyer, H. Ruan, and C. Yang, "Guidestar-assisted wavefront-shaping methods for focusing light into biological tissue," Nat. photonics 9, 563-571 (2015)]. At increasingly longer wavelengths, Mie and Rayleigh scattering becomes less problematic, but at wavelengths above ~2 µm, absorption by water begins to dominate the optical loss [S. L. Jacques, "Optical properties of biological tissues: a review," Phys. Medicine & Biol. 58, R37 (2013)]. Along with the availability of efficient optical detectors in this region [A. Rogalski, "Infrared detectors: an overview," Infrared physics & technology 43, 187-210 (2002)], this has led researchers to conclude that the 1.0 µm to 1.7 µm near infrared region is an optimal one for imaging in biological tissue [Y. Duan and B. Liu, "Recent advances of optical imaging in the second near-infrared window," Adv. materials 30, 1802394 (2018)]. Fortunately, the near IR is also a minimally-absorbing wavelength in glass used in optical fibers [G. Keiser, Optical fiber communications, vol. 2 (McGraw-Hill New York, 2000)], and optical telecommunications components are readily available in this region. Operation at wavelengths>1 µm also minimizes the absorption of several materials commonly used in microfabrication (among them SiN, $SiO_2$, α-Si). For these reasons, some embodiments chose a target wavelength of 1310 nm.

Figure 23A:
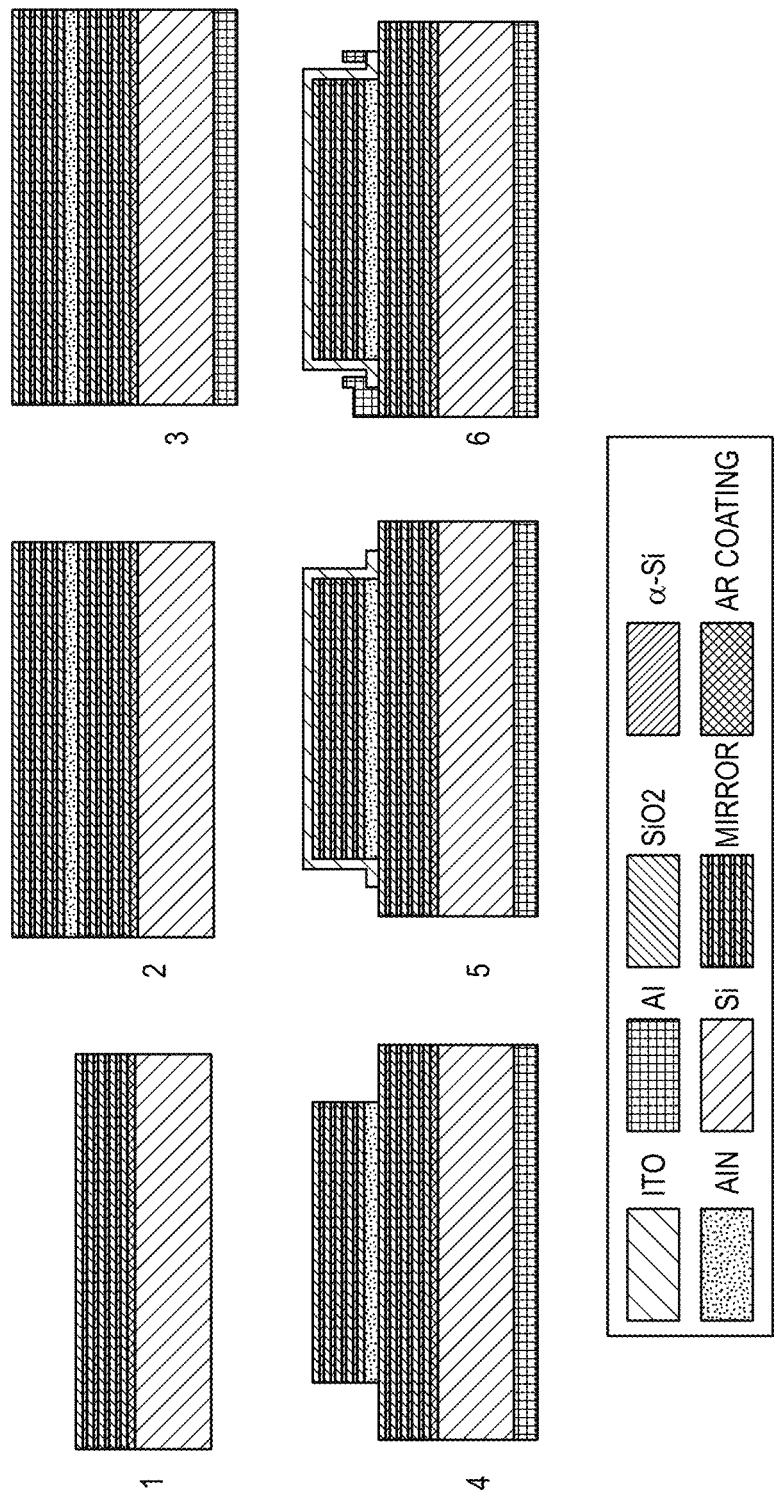
FIG. 23A shows example fabrication steps of an example electro-optic modulator (EOM).
Figure 23B:
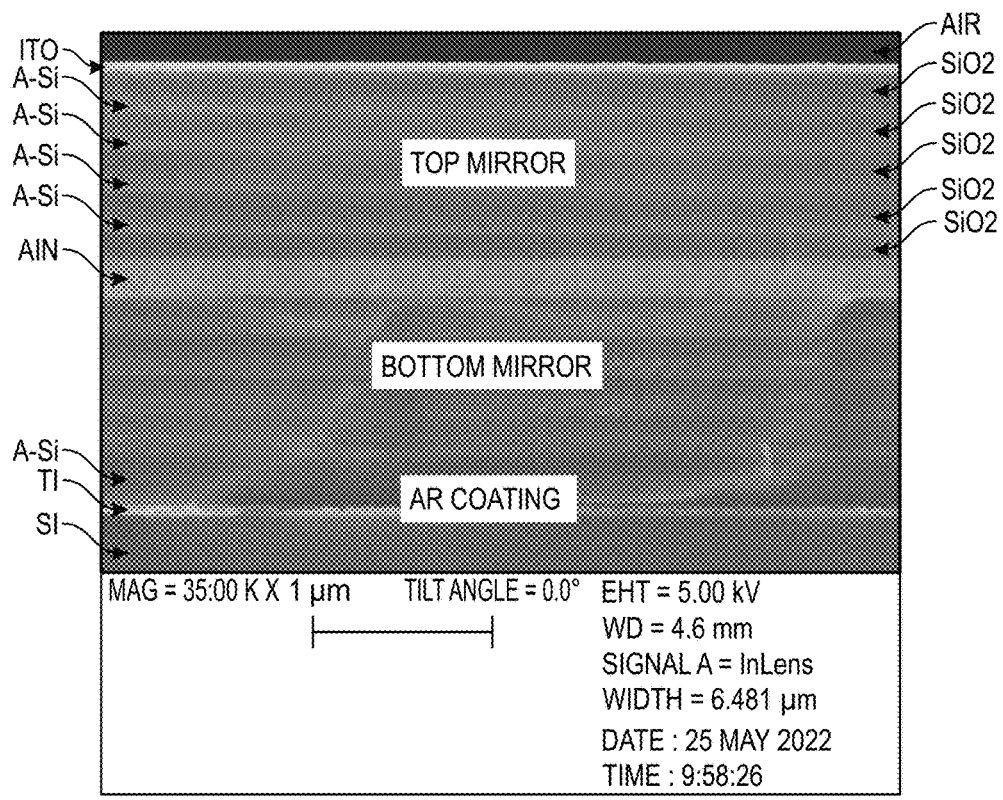
FIG. 23B shows an example cross-section of an example EOM.
Figure 23C:
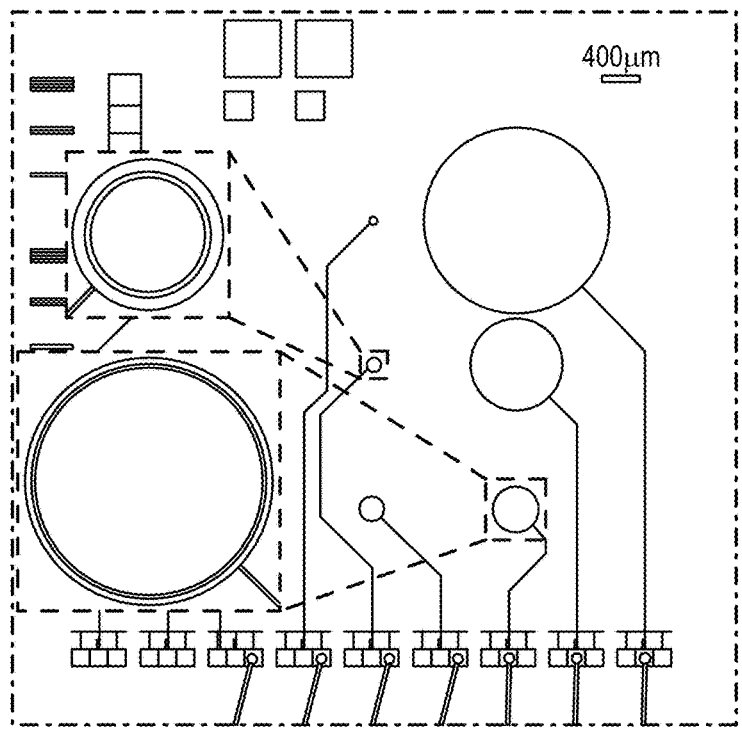
FIG. 23C shows an optical micrograph of an example fabricated 5×5 $mm^2$ die containing example different size EOMs, and further shows inset close-up top views of the 320 μm and 80 μm diameter example EOMs.

In an experiment disclosed herein, the electro-optic modulator (EOM) was fabricated using CMOS-compatible micromachining techniques. FIG. 23A shows the example fabrication steps, and FIG. 23B shows the cross-sectional SEM of the EOM. Briefly, in the example of FIG. 23A, an anti-reflection (ΔR) coating of 50 nm titanium (Ti) and 200 nm amorphous Si (α-Si) was deposited on a bare p-Si wafer. 9 quarter-wavelength layers of alternating 240 nm silicon dioxide ($SiO_2$) and 90 nm α-Si were then deposited using PECVD at 350° C. A 310 nm-thick aluminum nitride (AlN) layer was then sputtered, and second set of 9 alternating $SiO_2$ and α-Si layers was then deposited for the top mirror. The disclosed experiment then lithographically patterned circular regions with sizes between 5 µm and 1280 µm and etched the top mirror and the AlN layer. The disclosed experiment confirmed full clearing of the AlN layer with an AlN etchant (dilute TMAH) drop test. Next, the disclosed experiment sputtered 10 nm titanium (Ti)/100 nm Al on the backside of the wafer to compensate for film stress and provide an ohmic contact to the p-Si. After this, the disclosed experiment sputtered a 60 nm-thick layer of indium tin oxide (ITO) on top of the entire structure, lithographically patterned it, and ion milled all but a circle overlapping the original devices. Finally, the disclosed experiment patterned a final liftoff layer and evaporated 300 nm-thick Al on the surface of the wafer to form bond pads. The fabricated 5×5 $mm^2$ die containing different size devices and test structures, shown in FIG. 23C, was bonded with conductive silver epoxy and wire-bonded to a printed circuit board (PCB) for testing. Note that multiple devices were placed on the same die to enable fair performance comparison of different size devices.

Fabrication of high-quality and extremely smooth $SiO_2$ and α-Si layers allows the entire structure to be deposited at once. A challenge with deposition of Bragg mirrors is that as the number of layers increases, the mirror roughness tends to increase [M. Cho, J.-H. Seo, D. Zhao, J. Lee, K. Xiong, X. Yin, Y. Liu, S.-C. Liu, M. Kim, T. J. Kim et al., "Amorphous si/sio2 distributed bragg reflectors with transfer printed single-crystalline si nanomembranes," J. Vac. Sci. & Technol. B, Nanotechnol. Microelectron. Materials, Process. Meas. Phenom. 34, 040601 (2016)]. This degrades the reflectivity (R) of the mirror, lowering the device quality factor (Q). To avoid this, one implementation of this disclosure performed a 17-run definitive screening experiment for $SiO_2$ films deposited on bare Si substrates and for α-Si layers deposited on thermally oxidized substrates. The implementation varied temperature, pressure, and available gas flows, and measured: the deposition rate with cross-sectional SEM, film roughness using AFM, and stress using wafer curvature.

Both optimal $SiO_2$ and α-Si recipes achieved rms roughnesses of <1 nm and film stresses of ~200 MPa. Fully-deposited 9-layer mirrors maintained rms roughnesses of 0.8 nm, and the roughness did not increase substantially with an increasing layer number.

Experiment Results

Figure 24A:
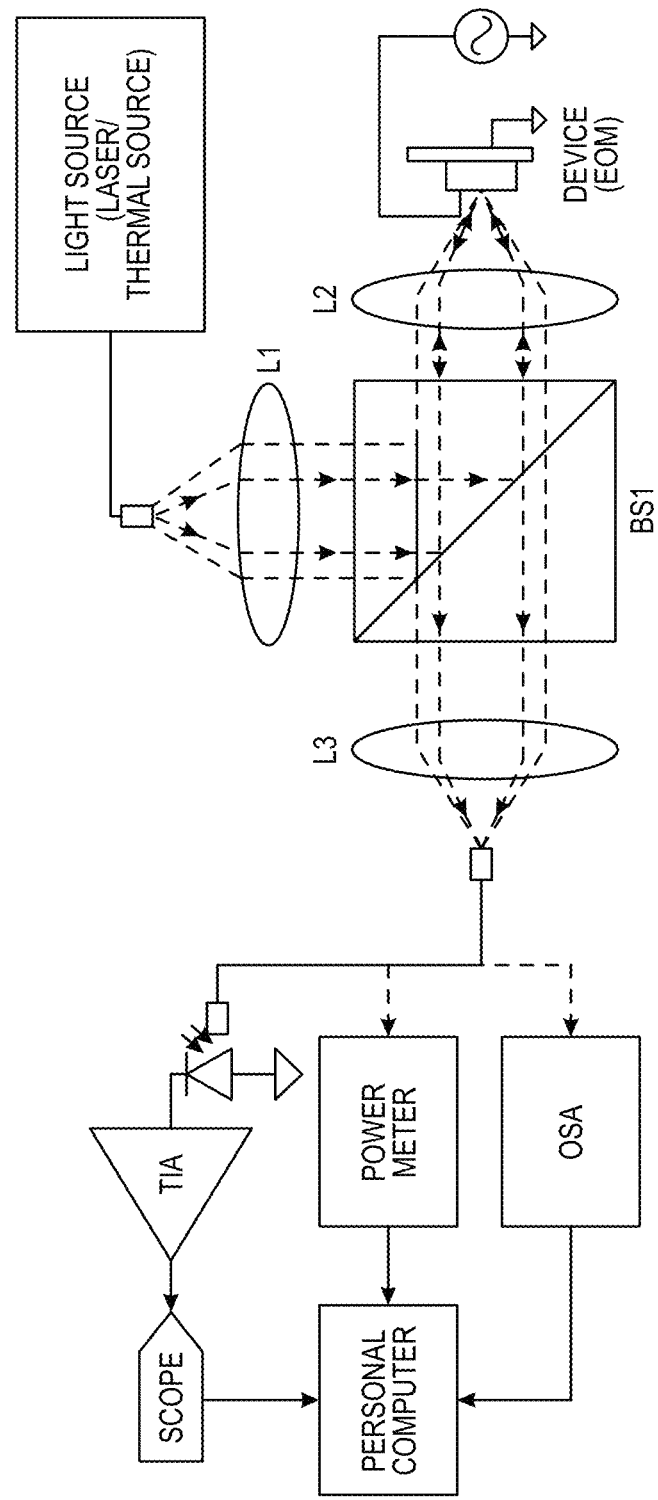
FIG. 24A shows a schematic diagram of an example setup used to measure the EOM reflectivity.
Figure 24B:
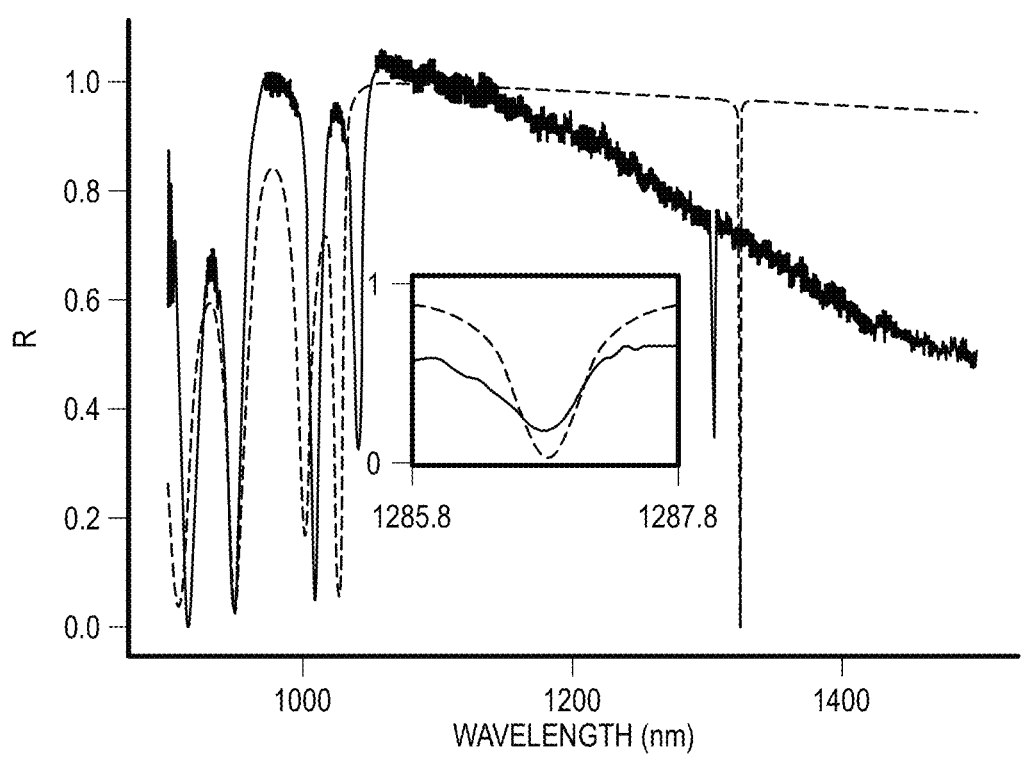
FIG. 24B shows an example reflectance of planar film with anti-reflection coating (ARC) measured using a thermal source and an optical spectrum analyzer (OSA), with a dashed line representing simulation results using a transfer-matrix method (TMM) package.

Some embodiments measured reflectance (R) spectra of the electro-optic modulator (EOM) using a beamsplitter-based cage system reflectometer. FIG. 24A shows a schematic diagram of an example setup used to measure the EOM reflectivity. In this setup, some embodiments used a fiber-coupled thermal broadband light source. The light was collimated with a 15 mm fixed-focus collimation package L1, reflected with a 50/50 plate beamsplitter BS1, and focused onto the device with a 40 mm piano-convex lens L2. The reflected light from the device was then coupled through a focusing lens L3 into a 100 µm core/0.1 NA fiber, which was measured by an optical spectrum analyzer. To obtain a R spectra of the EOM, the measured spectrum data was normalized to the data collected in the same manner using a 100 nm gold-coated reference sample; the sample has approximately unity reflectance above 800 nm [J. M. Bennett and E. Ashley, "Infrared reflectance and emittance of silver and gold evaporated in ultrahigh vacuum," Appl. Opt. 4, 221-224 (1965)]. FIG. 24B shows the measured and predicted R spectra of the EOM with anti-reflection coating (ARC), showing that the experiment data agree well with the data predicted from a transfer matrix model using the device parameters provided in Table 5. It is likely that this indicates that the difference in the measured and predicted spectra mainly results from difficult-to-predict variations in the oxide absorption coefficient throughout the layer stack.

Figure 25A:
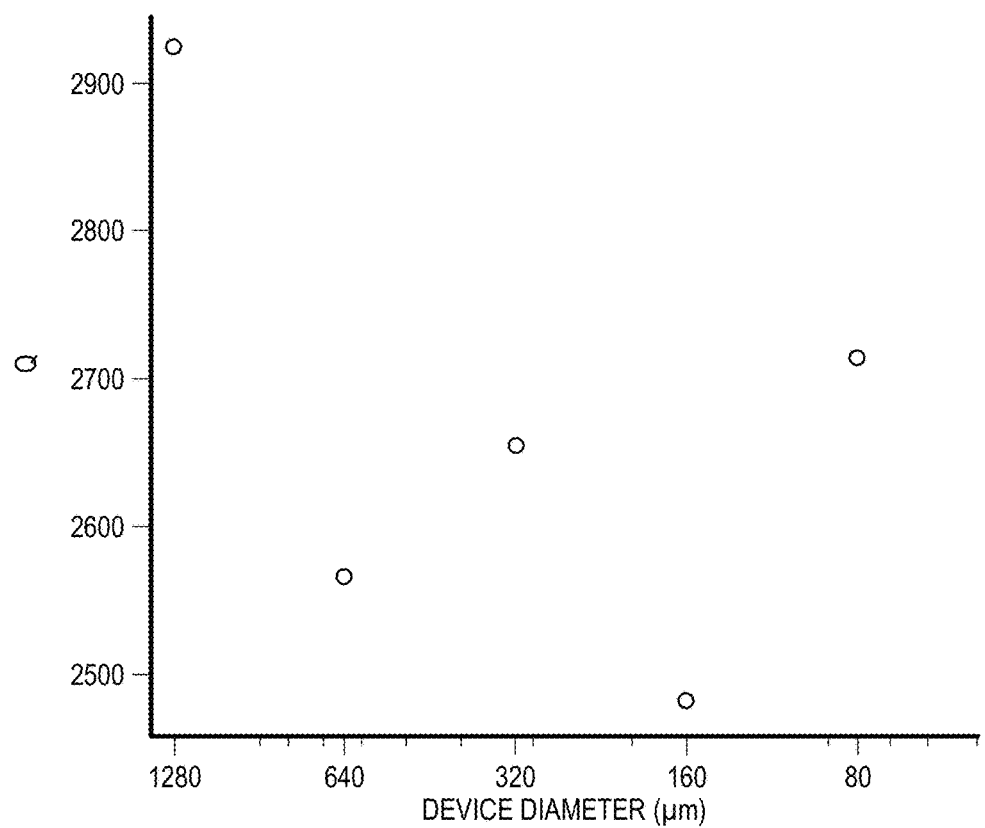
FIG. 25A illustrates example measured quality factor (Q) values for example devices with differently-sized diameters, from 80 μm to 1280 μm.

The ARC devices achieved a maximum quality factor (Q) of 2900, but optical coupling reduces modulation gain (β) at smaller device sizes. Some embodiments measured the Q of each device by sweeping the tunable laser source near resonance, and fitting the resultant measured spectra to a Lorentzian at a fixed Q using least-squares linear regression. An example fit curve is shown in FIG. 18. The Q measured for the five different device sizes tested are shown in FIG. 25A, and range from ~2500 to ~2900. These are representative of devices measured elsewhere on the same wafer and across wafers, with typical Q values in the range of 1000-3000. The largest device Q (~2900) measured with the tunable laser was almost three times that (~1000) measured with the optical spectrum analyzer. It is suspected that this is due to the poor $M^2$ of the fiber-coupled thermal source compared to the tunable laser, and the resultant much wider range of incident angles present when using the thermal source, leading to a smeared-out spectra near resonance.

Figure 25B:
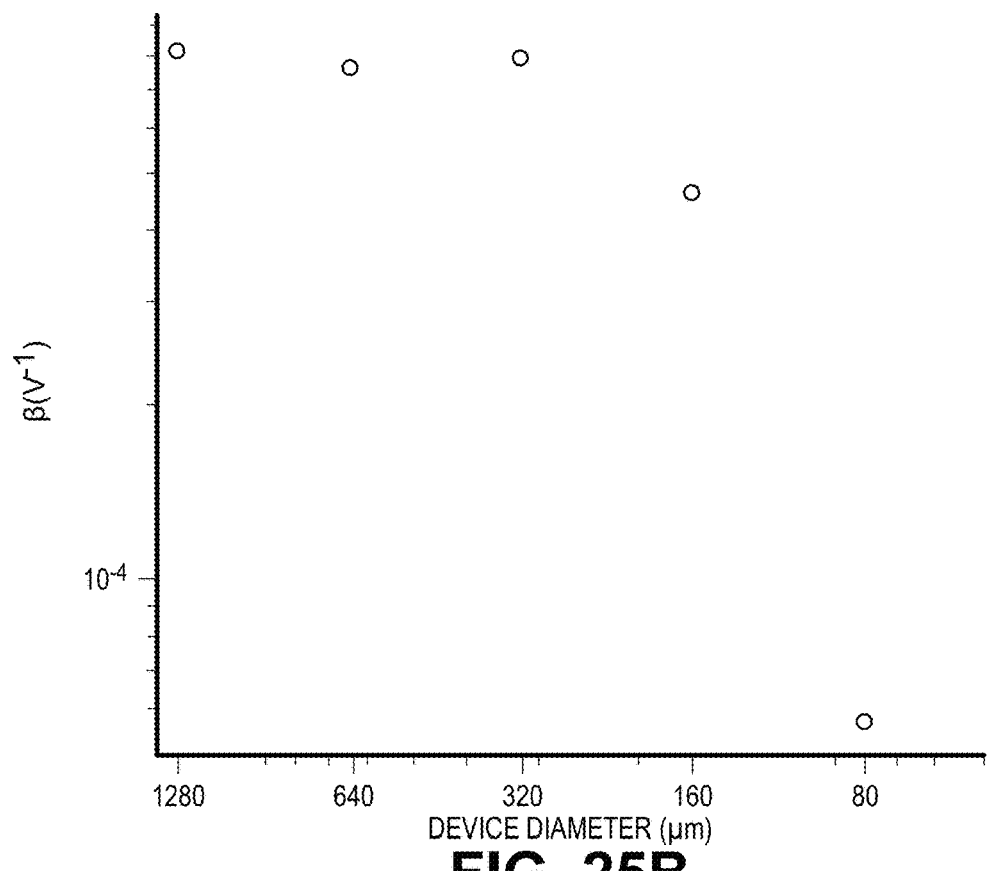
FIG. 25B illustrates example measured modulation gain (β) for example differently-sized devices.

While the Q-factor for smaller devices remained high, the device β decreased substantially from $2.3*10^{-3}V^{-1}$ to $9*10^{-5}V^{-1}$ (FIG. 25B). This may primarily be due to the poor optical coupling from the beam to the device, due to the relatively high reflectance observed when aligning to the device.

The anti-reflection coating (ARC) enables achieving high quality factor (Q) by eliminating back reflection of light due to the transparent substrate. One challenge of operating the device at a wavelength of around 1300 nm is that Si substrate is transparent in this region. This is because the incident light near resonance that passes through the device layers will be reflected off the bottom electrode surface, degrading the device's Q and therefore capability of modulating light intensity. Some embodiments alleviate this problem by adding an ARC based on a α-Si (n≈3.5) layer on top of a Ti layer underneath the bottom mirror; these materials have high compatibility with standard fabrication tools. Any light near the device resonance which makes it through the bottom mirror is absorbed by the ARC, eliminating the effect of the substrate on the device performance. FIG. 20 shows an example measured and predicted reflectance (R) spectra of the device without ARC, revealing that the device without ARC has a substantially lower Q (440) than that (2900) of the device with ARC as expected.

Figure 26A:
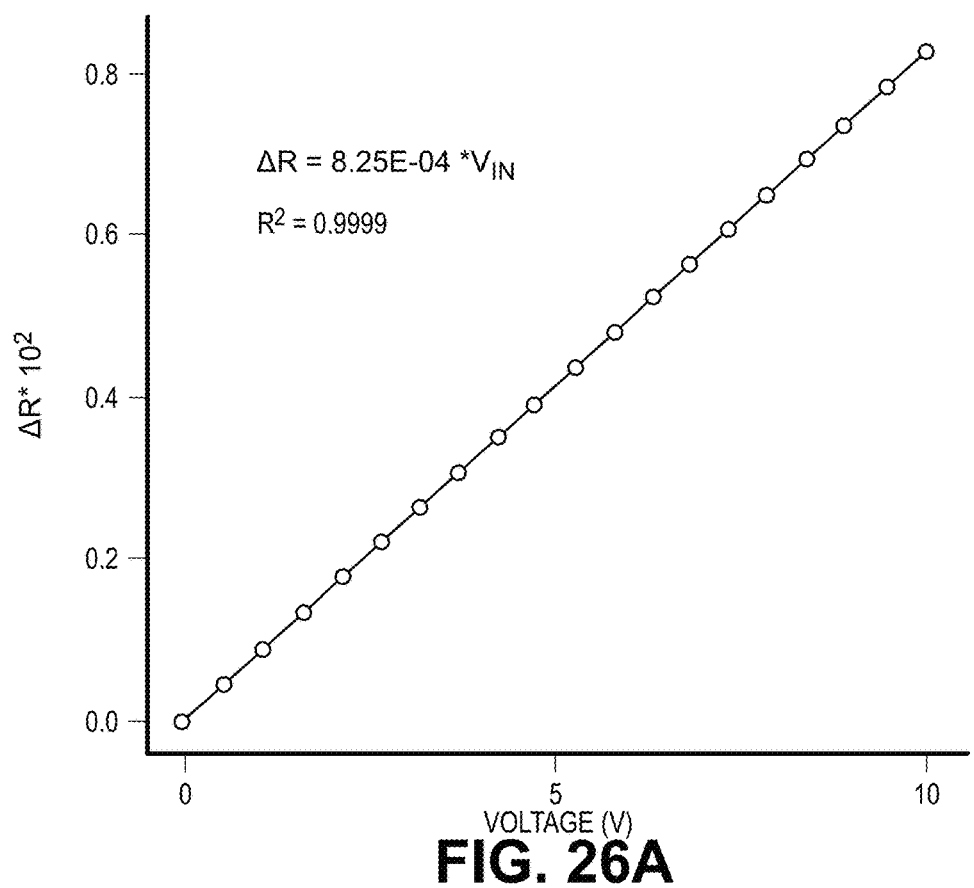
FIG. 26A shows an example measured modulation depth (ΔR) versus input voltage in free space.

To extract the modulation depth (ΔR) of the electro-optic modulator (EOM), some embodiments utilized the same cage system with a fiber-coupled tunable laser source. As this device has a high-Q, the optical source linewidth must be much smaller than the resonant peak linewidth for light intensity amplitude modulation to function properly. The only light source capable of providing this at sufficient power is the laser. Therefore, some embodiments used a tunable O-band laser as a light source, coupled to a 8 μm core diameter fiber. Some embodiments measured the change in device photocurrent using an integrated fiber-coupled photodiode and a transimpedance amplifier (TIA) with a gain of $10^5$ V/A and a bandwidth of 4 MHz. The TIA output may be digitized using an oscilloscope with a 5 MHz sampling rate and then sent to a computer for data storage. Prior to ΔR measurements, some embodiments swept the laser wavelength around the resonant wavelength to precisely identify the operating wavelength. To maximize the ΔR during operation, the laser wavelength may be set slightly off-resonance where the resonant slope was the steepest. In the example measurement, a 100 Hz sinusoidal signal was applied with various peak amplitudes from 10 mV to 10V to the EOM and measured the change in optical power reflected off the device. The measured power value at 100 Hz was normalized to the DC level to extract the ΔR. FIG. 26A depicts the measured ΔR versus voltage amplitude applied to the EOM with a diameter of 1280 μm, showing that the device is highly linear ($R^2=0.9999$) in the typical CMOS voltage range of 0.5-5V and maintains linearity even well above the typical maximum voltage tolerated by CMOS electronics. The measured device gain β of $0.8*10^{-3}V^{-1}$ is slightly lower than the predicted value from analytical model value of $2.5*10^{-3}V^{-1}$ (See Table 6). The most likely cause of the discrepancy is the relatively poor fit of a Lorentzian lineshape to the measured reflection spectra—leading to an inaccurate estimation of the true slope. It is also possible that the deposited AlN had slightly lower values of $d_{33}$ and/or $r_{33}$ due to direct deposition on oxide.

Figure 26B:
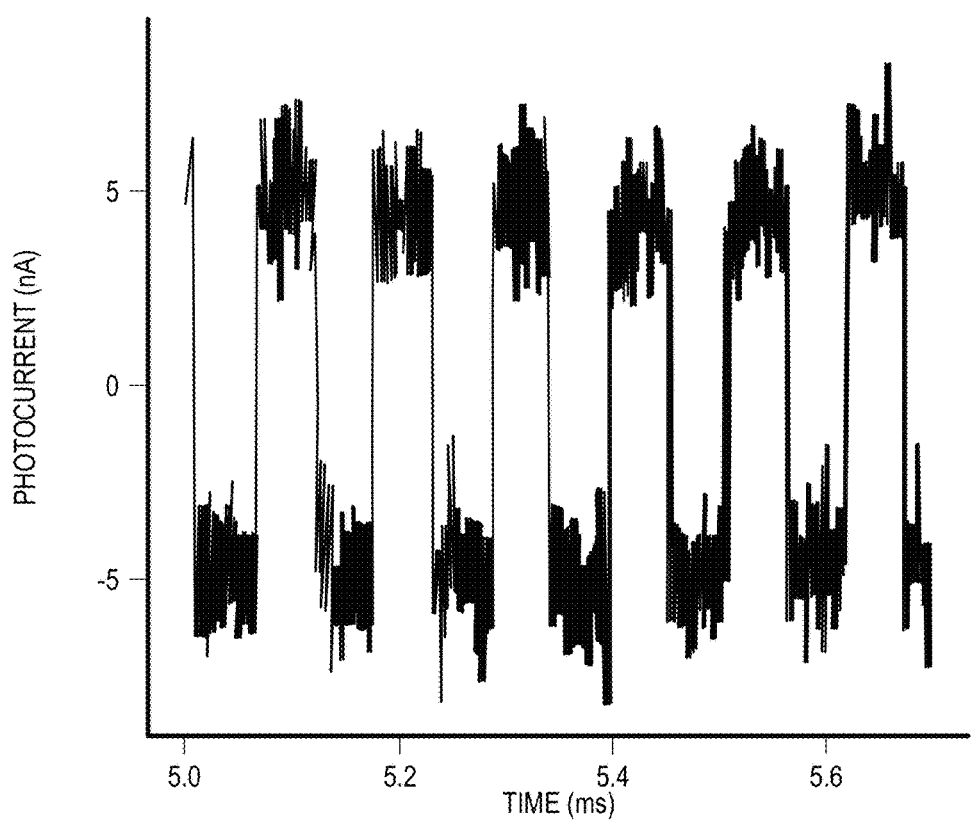
FIG. 26B shows example time-domain transient optical response of the EOM operated with a $0.5V_{pp}$, 9 kHz square-wave signal at a 1 MHz sampling frequency.
Figure 26C:
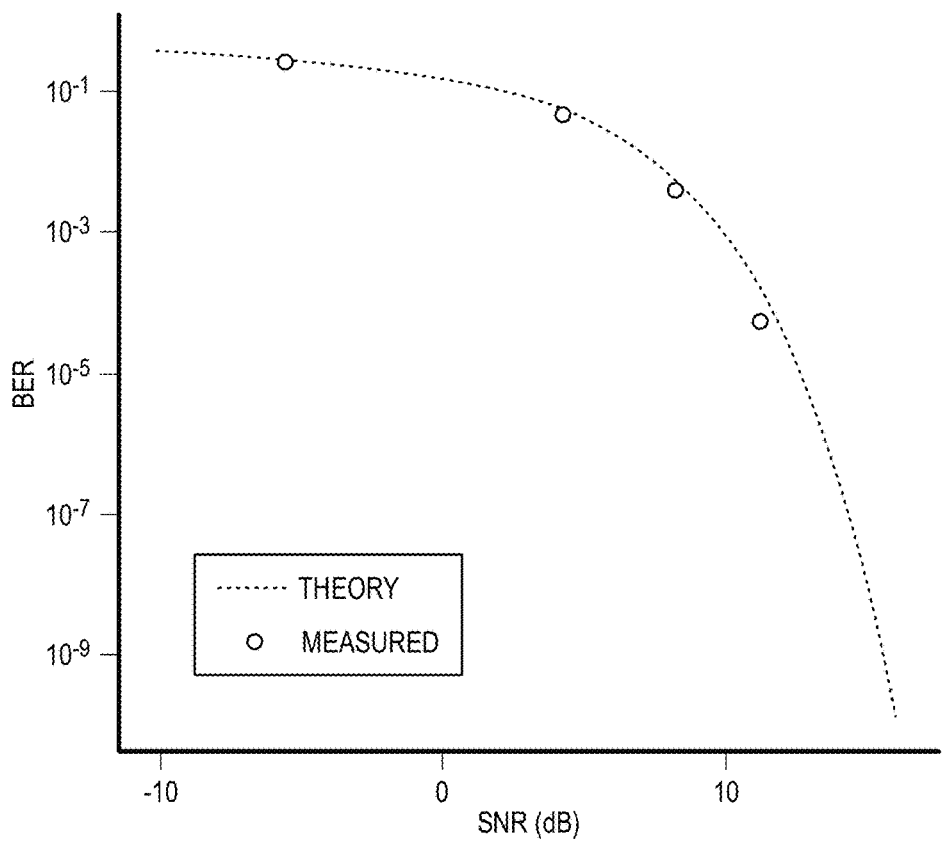
FIG. 26C illustrates an example plot of BER versus SNR, obtained by varying incident optical power from 0.3 mW to 10 mW.

The electro-optic modulator (EOM) can enable uplink data communication with implants through digital amplitude modulation of the reflected light from the device with a bit error rate (BER) of $<10^{-5}$ in a bandwidth of 4 MHz. To test the system's ability to transmit digital data, the same setup was used as was in the ΔR experiment and operated the 1280 μm diameter EOM with square-wave voltages with a peak-to-peak amplitude of 0.5V and frequencies of 9 kHz and 100 kHz, generated by a function generator. To reduce the effect of laser low-frequency noise, such as 1/f noise, on the output, the data was post-filtered from the device at 1 kHz through a 3rd-order butterworth high-pass filter. FIG. 26B shows the time-domain transient optical response of the EOM operated with a 9 kHz square-wave signal at a 1 MHz sampling frequency. For the BER measurement, 500,000 data points were collected from the device operated with a 100 kHz square-wave signal at a 5 MHz sampling frequency, and the first and last five time constants (5000 points) of the data due to filtering were excluded. This disclosed experiment measured the signal-to-noise ratio (SNR) by summing the power of the first harmonic and all subsequent odd harmonics, taking this to be the signal power, and the remaining power to be the noise power. This experiment took each individual sample of the data to be a "bit," excluding the samples during a high-to-low or low-to-high transition, as well as the adjacent samples. To experimentally calculate the BER as a function of SNR, the laser optical power was varied between 0.3 mW and 10 mW during the measurement. FIG. 26C shows the example measured BER versus SNR, showing perfect agreement with the BER predicted using AWGN channel model. It may be noted that the BER performance of the device can be improved when the device is operated with larger modulation voltages, as applying higher voltages increases the device ΔR. Further regarding the example of FIG. 26C, the data was collected at 5 MHz sampling rate with a 4 MHz TIA bandwidth and a 50% duty-cycle, 100 kHz square-wave input modulation signal. The BER was predicted using an AWGN channel model, and calculated treating all individual sample points as bits, excluding the square wave HIGH→LOW and LOW→HIGH transition points.

SNR increased roughly linearly with output power, from −5 dB to +11 dB when increasing the power from 0.3 mW to 10 mW. Most experiments done here, when highpass filtered at 1 kHz, were within 1 dB of the shot noise limit. At frequencies<1 kHz, the laser drift and 1/f noise becomes dominant.

Figure 26D:
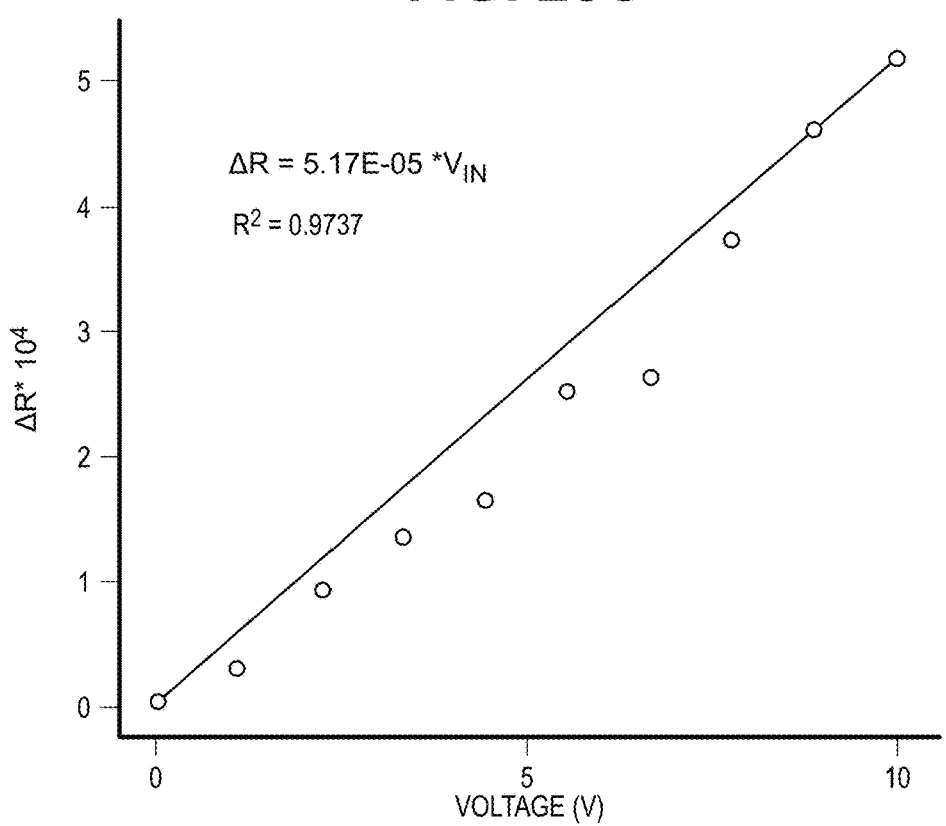
FIG. 26D shows example ΔR versus input voltage measured through 0.8 mm-thick chicken skin resting on the device.

In one experiment disclosed herein, the device operated through 0.8 mm-thick dry chicken skin, thus demonstrating robust operation. As a proof-of-principle to determine whether this device could be implanted subcutaneously, an experiment measured the ΔR of the 1280 μm diameter EOM as a function of applied modulation voltage by placing it below the 0.8 mm-thick dried chicken skin layer. For this experiment, the laser power was set to 1 mW and used a measurement frequency of 9 kHz. The measurement result is depicted in FIG. 26D, showing that the device exhibited a 30 times lower ΔR than the device operated in free space. The ΔR reduction is mainly due to tissue light scattering and results in a concomitant reduction in the BER. Furthermore, the reflected light power from the device coupled into the output fiber was approximately 10 times lower than without the skin present due to the light attenuation in tissue.

Figure 27A:
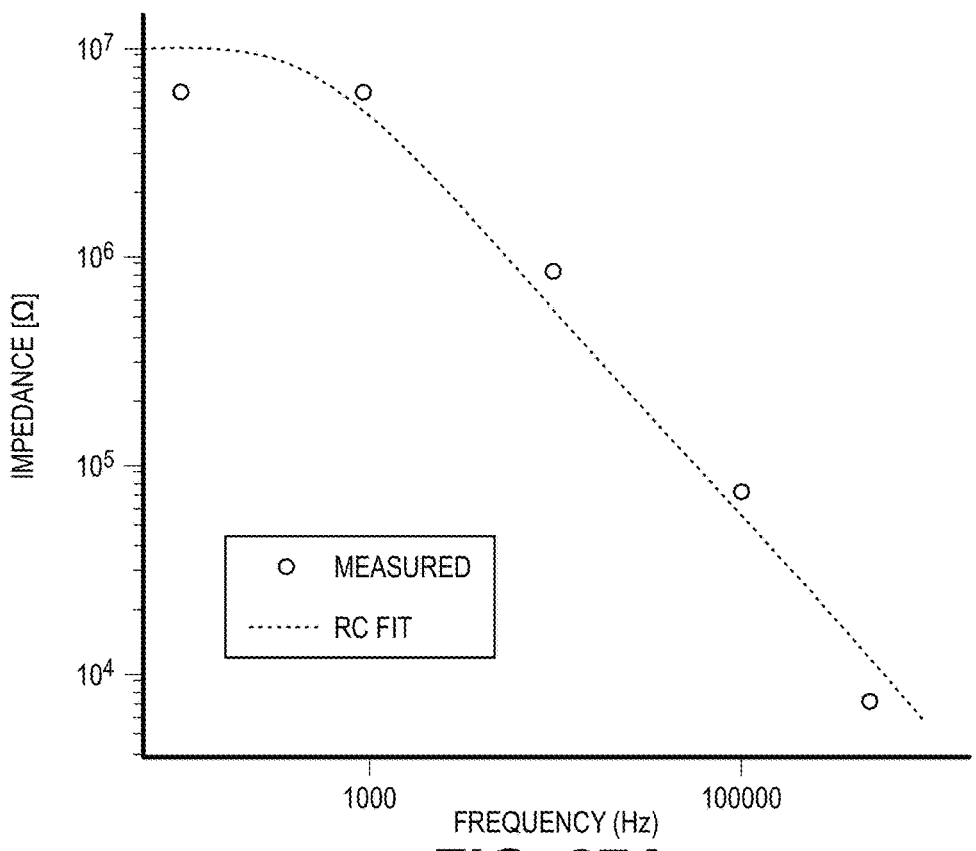
FIG. 27A shows example device impedance of a representative 1280 μm diameter device. The dashed line represents lumped element parallel RC model, with a fitted R value of 1 kΩ and C value of 28 pF (zero at ~5 MHz). This example uses a theoretical C value from literature permittivities and SEM thicknesses is 32 pF.
Figure 27B:
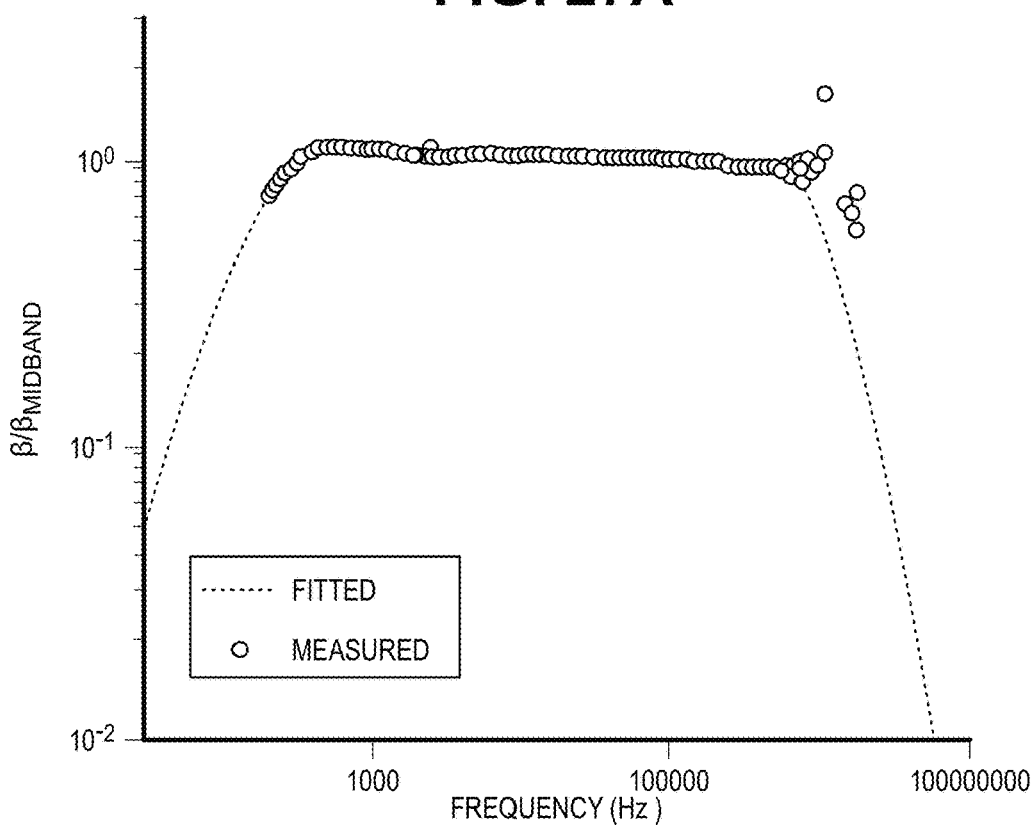
FIG. 27B shows an example device normalized gain versus frequency for a 1280 μm device. In this example, fitted single-pole corner frequencies of 9 Hz and 8 MHz using a transimpedance amplifier (TIA) bandwidth (BW) of 4 MHz. $\beta_{midband}$ refers to gain at 10 kHz. Some other device sizes have virtually identical frequency responses limited by the TIA BW.

The 1280 µm diameter device can operate with a 5 MHz bandwidth (BW), which increases to ~300 MHz for the smallest 80 µm device. The underlying mechanism by which this device operates may be a mixture of the piezoelectric and electro-optic effects. The speed of piezoelectric actuation is ultimately limited by the speed at which the material can deform—the speed of sound. For these devices operating in the longitudinal mode along the thickness direction, which have an active thickness of 300 nm, this yields a theoretical BW of ~30 GHz using a speed of sound of 104 m/s in AlN [D. Gerlich, S. Dole, and G. Slack, "Elastic properties of aluminum nitride," J. Phys. Chem. Solids 47, 437-441 (1986)]. For this reason, the device operating BW in this work is set by its electrical BW, or its RC time constant. Some experiments disclosed herein extracted the device series resistance R and capacitance C by fitting the lumped element RC model to the measured impedance data, shown in FIG. 27A for the example 1280 µm device. As some embodiments used a thin layer of relatively low-quality ITO, the device series resistance was obtained to be ~1 kΩ for all device sizes. Device capacitance values from fitting vary from ~28 pF for the largest 1280 µm device to ~0.5 pF for the smallest 80 µm device, after correcting for bond pad capacitance. This makes the theoretical BW range from ~6 MHz for the largest device to ~300 MHz for the smallest device. FIG. 27B shows the measured optical frequency response of the example 1280 µm device that matches well with the theoretical BW predicted using the R and C values from the fitting. The fitted high-frequency rolloff fitted to 8 MHz was close to that expected (4 MHz from the limiting TIA or 5 MHz from the device). Also found was an unexpected low-frequency rolloff, which fitted to a pole-zero pair at 9 Hz. This may be due to leakage in the AlN layer, and would be consistent with a leakage resistance of 600MΩ. This is substantially higher (~6×) than measured, but also higher than the values the impedance meter could reliably measure, and corresponds to a resistivity of $2.6*10^{11}$ Ω·cm, in the typical AlN resistivity range of $10^{11}$-$10^{13}$ Ω·cm [K. Butcher and T. Tansley, "Ultrahigh resistivity aluminum nitride grown on mercury cadmium telluride," J. Appl. Phys. 90, 6217-6221 (2001)].

Conclusion and Discussion

The discussion herein presents a high-Q electro-optic modulator (EOM), formed by a piezoelectric AlN thin film sandwiched between two high-reflectance Bragg mirrors, and may be used for wireless medical implants. The EOM may be fabricated using standard fabrication processes with the highest temperature of 350° C., advantageously making it CMOS compatible. In some embodiments, the device may operate at a wavelength of ~1300 nm in the NIR window with low tissue absorption, enabling to establish an efficient optical wireless link to implants for high-bandwidth uplink data transmission. The device operation is successfully demonstrated ex vivo in chicken skin. Some embodiments also demonstrated that the device is scalable down to micrometer in size (<100 µm) and capable of operating at CMOS voltages down to 0.5V.

Some embodiments placed the device electrodes on the top of the Bragg mirror and the bottom of the Si substrate. This enables relatively easy fabrication, and reduces the total device capacitance, increasing the BW. However, the resulting capacitive division mainly between the mirrors with the capacitance of 25 pF/mm$^2$ and the piezoelectric layer with the capacitance of 240 pF/mm$^2$ results in a smaller voltage acting on the piezoelectric layer than the voltage applied to the device, reducing the maximum achievable β. The β can be theoretically improved by a factor of ~9 if the electrodes are sandwiched between the mirror layers and the piezoelectric layer, preventing this capacitive division. Since ITO is highly absorbing around the operating wavelength of 1300 nm (see FIG. 16), this also requires very thin ITO layers (<5 nm) to form the device electrodes, which increases the device contact resistance and therefore further reduces the BW.

The choice of a different lower-absorption transparent conducting oxide to form the device top electrode could increase the device BW by two orders of magnitude. Here, some embodiments used ITO to form an electrode. However, the ITO absorption near the operating wavelength of interest (~1300 nm) is very high (K=0.2). Thus, some embodiments use a thin ITO layer, leading to a relatively low BW due to its relatively high resistivity (~$10^{-3}$ Ω*cm). By using a different conducting oxide such as ZnO with absorption and resistivity lower than those of ITO [C. Stelling, C. R. Singh, M. Karg, T. A. König, M. Thelakkat, and M. Retsch, "Plasmonic nanomeshes: their ambivalent role as transparent electrodes in organic solar cells," Sci. reports 7, 1-13 (2017)], the device BW can be improved by two orders of magnitude.

Modification of the fabrication process would allow other piezoelectric materials to be used. Some embodiments used aluminum nitride (AlN) as the active piezoelectric material for its relatively low permittivity (E=8.5) and ability to deposit directly on top of thermal SiO$_2$, as shown in this disclosure. However, AlN has a relatively small piezoelectric constant ($d_{33}$≈5 µm/V) [C. Lueng, H. L. Chan, C. Surya, and C. Choy, "Piezoelectric coefficient of aluminum nitride and gallium nitride," J. applied physics 88, 5360-5363 (2000)] compared to other piezoelectric materials such as BTO ($d_{33}$ 300 µm/V) [M. Vijatović, J. Bobić, and B. D. Stojanović, "History and challenges of barium titanate: Part ii," Sci. Sinter. 40, 235-244 (2008)]. These materials with higher $d_{33}$ coefficients would allow for a much greater modulation depth (ΔR) at a fixed applied voltage, leading to improved SNR and hence BER, especially if the device electrodes are placed between the mirror layers and the piezoelectric layer. However, they also have much higher permittivities. BTO, for example, often has $\epsilon_r$>1000 [P. Fu, Z. Xu, R. Chu, X. Wu, W. Li, and X. Li, "Structure and electrical properties of (1−x)(na0.5bi0.5) 0.94 ba0.06tio3-x bialo3 lead-free piezoelectric ceramics," Mater. & Des. 46, 322-327 (2013)], which results in a smaller device BW.

System level improvements are possible. In one example, the system's optical insertion loss from laser output to photodiode input was ~20 dB, as some embodiments used fiber-coupled equipment for ease of switching between different pieces of equipment. Advantageously, direct coupling of light reflected off the device to a collecting photodiode without using an optical fiber could reduce the insertion loss and hence increase the received optical power by ~15 dB, and to as high as 17 dB when the device is optically biased at a DC reflectance of 50%.

Some embodiments post-processed the data from the device using a high-pass filter to reduce the effect of the laser 1/f noise on the system output. After high-pass filtering, the measured noise was typically within 1 dB of the shot-noise limit. Another improvement can be achieved by using closed-loop noise reduction techniques [P. C. Hobbs, "Reaching the shot noise limit for $10," Opt. Photonics News 2, 17-23 (1991)] that could enable to minimize the laser 1/f noise and further improve the system noise performance.

Unlike traditional integrated photonic optical modulators, the electro-optic modulator (EOM) does not require a very precise alignment of the light beam. One of the most challenging aspects of existing high-Q optical modulators—which typically make use of integrated photonics—is optical coupling into and out of the device. Traditionally, this is achieved by placing an optical fiber directly above an edge or grating coupler, and requires sub-micron to single-micron accuracy, depending on the method used [J. S. Lee, L. Carroll, C. Scarcella, N. Pavarelli, S. Menezo, S. Bernabé, E. Temporiti, and P. O'Brien, "Meeting the electrical, optical, and thermal design challenges of photonic-packaging," IEEE J. selected topics quantum electronics 22, 409-417 (2016)]. It may be necessary to dramatically relax this alignment requirement for a modulator intended to be used to build a wireless implant because such alignment precision is extremely difficult to achieve. In contrast to the existing photonic modulators, the EOM eliminates the need for high alignment accuracy, as it only requires the light beam focused to within the diameter of the device. For the largest 1280 μm diameter device, the transverse misalignment tolerance is roughly ±0.5 mm with the current setup.

The device operation may be sensitive to angular misalignment. For example, the EOM operation may be sensitive to incident angle ($\theta$) between the beam direction and the device normal due to its high-Q. Any deviation in $\theta$ may cause a shift in the device resonant wavelength that can be approximately calculated using the formula: $\lambda_r = \lambda_r \cdot (1 - \cos(\theta)^2)$ and a reduction in the power coupled to the device, which is also quadratic with $\theta$. Therefore, angular alignment of the device to the laser beam should be carefully performed during the surgical placement of an EOM-based wireless implant in tissue.

Overall, this disclosure has shown that substantial improvement is possible at the device level and at the system level, with the potential for two orders of magnitude increase in bandwidth, and two orders of magnitude improvement in noise performance from improved optical coupling. This, combined with the results presented thus far, present a compelling case for use of this device as a platform for wireless readout of digital information from implantable devices. While this disclosure has demonstrated microscope-free alignment of devices down to 80 μm in size, further reductions in size are possible with more careful beam shaping and alignment procedures. Theoretically, devices with diameters as small as a single half-wavelength (600 nm) are possible to fabricate, at the expense of increased difficulty with alignment and optical coupling.

Other Matters

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

Of course, the applications and benefits of the systems, methods and techniques described herein are not limited to only the above examples. Many other applications and benefits are possible by using the systems, methods and techniques described herein.

EXEMPLARY EMBODIMENTS

Embodiment 1. A method of measuring a voltage, the method comprising:
  applying a voltage to an optical resonator of a voltage sensor, the optical resonator comprising: (i) a top electrode layer, (ii) a piezoelectric layer, and (iii) a substrate;
  illuminating, with a light source, the optical resonator of the voltage sensor with light comprising an incident optical power at an input wavelength, wherein the input wavelength is offset from a resonant wavelength of the optical resonator at a baseline voltage; and
  measuring the applied voltage by measuring a reflected light power reflected from the illumination by the optical resonator.
Embodiment 2. The method of embodiment 1, wherein:
  the measuring of the applied voltage occurs by determining a change in reflectance of the optical resonator caused by the applied voltage.

Embodiment 3. The method of any one of embodiments 1-2, wherein the determining the change in reflectance comprises determining the change in reflectance based on: (i) the incident optical power, (ii) the measured reflected light power, and (iii) a reflectance of the piezoelectric material at the baseline voltage.

Embodiment 4. The method of any one of embodiments 1-3, wherein the measuring the applied voltage occurs by:
determining a reflectance of the optical resonator at the applied voltage based on: (i) the incident optical power, and (ii) the measured reflected light power;
determining a change in reflectance of the optical resonator from: (i) a baseline reflectance of the optical resonator at a baseline voltage to (ii) the determined reflectance of the optical resonator at the applied voltage; and
determining the applied voltage based on the determined change in reflectance of the optical resonator.

Embodiment 5. The method of any one of embodiments 1-4, wherein the measuring the applied voltage occurs by:
determining a reflectance of the optical resonator at the applied voltage based on: (i) the incident optical power, and (ii) the measured reflected light power;
determining a change in reflectance of the optical resonator from: (i) a baseline reflectance of the optical resonator at a baseline voltage to (ii) the determined reflectance of the optical resonator at the applied voltage; and
determining the applied voltage based on: (i) the determined change in reflectance of the optical resonator, and (ii) a sensor gain calculated based on:
an amplitude of a resonant dip of a reflectance curve of the piezoelectric layer;
a quality factor of the optical resonator;
a thickness of the optical resonator;
thickness mode piezoelectric strain coefficient of the piezoelectric layer;
a refractive index of the piezoelectric layer; and
a Pockels coefficient of the piezoelectric layer.

Embodiment 6. The method of any one of embodiments 1-5, wherein the input wavelength is a wavelength that is a steepest point of a reflectance curve of the piezoelectric layer.

Embodiment 7. The method of any one of embodiments 1-6, wherein the input wavelength is determined according to a full-width-half max (FWHM) property of a reflectance curve of the piezoelectric layer.

Embodiment 8. The method of any one of embodiments 1-7, wherein the piezoelectric layer has a thickness mode piezoelectric strain coefficient of greater than 50 pm/V.

Embodiment 9. The method of any one of embodiments 1-8, wherein the piezoelectric layer has a Pockels coefficient of greater than 50 pm/V.

Embodiment 10. The method of any one of embodiments 1-9, wherein the optical resonator further comprises a first mirror on a first side of the piezoelectric layer, and a second mirror on a second side of the piezoelectric layer.

Embodiment 11. The method of embodiment 10, wherein the first mirror and the second mirror each comprise alternating layers of silicon dioxide ($SiO_2$) and amorphous silicon (Si).

Embodiment 11A. The method of embodiment 11, wherein the alternating layers of both the first mirror and the second mirror are fabricated using plasma enhanced chemical vapor deposition (PECVD).

Embodiment 12. The method of embodiment 10, wherein the first mirror and the second mirror each comprise a first layer comprising a first material with a first refractive index, and a second layer comprising a second material with a second refractive index, wherein the first refractive index is different than the second refractive index.

Embodiment 13. The method of any one of embodiments 1-12, wherein the optical resonator further comprises:
a first plurality of electrodes positioned on a top side of the piezoelectric layer, wherein the first plurality of electrodes is transparent;
a second plurality of electrodes positioned on a bottom side of the piezoelectric layer;
a first mirror positioned on the first plurality of electrodes, the first mirror comprising a first layer with a first refractive index, and a second layer with a second refractive index, wherein the first refractive index of the first mirror is different than the second refractive index of the first mirror; and
a second mirror positioned on the second plurality of electrodes, the second mirror comprising a first layer with a first refractive index, and a second layer with a second refractive index, wherein the first refractive index of the second mirror is different than the second refractive index of the second mirror.

Embodiment 13A. The method of embodiment 13, wherein the second plurality of electrodes is opaque.

Embodiment 14. The method of any one of embodiments 1-13, wherein the optical resonator has a diameter of between 15 micrometers and 25 micrometers.

Embodiment 15. The method of any one of embodiments 1-14, wherein the piezoelectric layer comprises: barium titanate (BTO), potassium sodium niobate (KNN), bismuth ferrite (BFO), or zirconate titanate (PZT).

Embodiment 15A. The method of any one of embodiments 1-15, wherein the piezoelectric layer is positioned between the top electrode layer and the substrate.

Embodiment 16. An optical voltage sensor, comprising:
optical resonator comprising: (i) a top electrode layer, (ii) a piezoelectric layer, and (iii) a substrate; and
one or more processors configured to:
determine a reflected light power created by light incident on the optical resonator, the light incident on the optical resonator comprising an incident optical power at an input wavelength, wherein the input wavelength is offset from a resonant wavelength of the optical resonator; and
measure, based on the reflected light power reflected from the optical resonator, an applied voltage applied to the optical resonator.

Embodiment 17. The optical voltage sensor of embodiment 16, wherein:
the top electrode comprises an indium tin oxide (ITO) film; and
the piezoelectric layer comprises aluminum nitride (AlN).

Embodiment 18. The optical voltage sensor of any one of embodiments 16-17, wherein:
the optical resonator further comprises a backside aluminum layer; and
the piezoelectric layer is positioned on a top of the substrate, and the backside aluminum layer is positioned on a bottom of the substrate.

Embodiment 19. The optical voltage sensor of any one of embodiments 16-18, wherein:
the optical resonator further comprises a bond pad layer comprising titanium and aluminum; and
the bond pad layer is positioned both on a top side of the piezoelectric layer, and a top side of the top electrode layer.

Embodiment 20. The optical voltage sensor of any one of embodiments 16-19, wherein the top electrode layer includes a mirror layer including a plurality of through-holes connecting a top section of the top electrode layer to a bottom section of the top electrode layer.

Embodiment 21. The optical voltage sensor of embodiment 20, wherein a material of the top section of the top electrode layer is a same material as a material that fills: (i) the through-holes; and (ii) the bottom section of the top electrode layer.

Embodiment 22. The optical voltage sensor of any one of embodiments 16-21, further including a bottom electrode layer, wherein:
the bottom electrode layer includes a mirror layer including a plurality of through-holes connecting a top section of the bottom electrode layer to a bottom section of the bottom electrode layer; and
a material of the top section of the bottom electrode layer is a same material as a material that fills: (i) the through-holes of the mirror layer of the bottom electrode layer; and (ii) the bottom section of the bottom electrode layer.

Embodiment 22A. The optical voltage sensor of any one of embodiments 16-22, wherein:
the one or more processors are configured to measure the applied voltage by:
determining a reflectance of the optical resonator at the applied voltage based on: (i) the incident optical power, (ii) the determined reflected light power;
determining a change in reflectance of the optical resonator from (i) a baseline reflectance of the optical resonator at a baseline voltage to (ii) the determined reflectance of the optical resonator at the applied voltage; and
determining the applied voltage based on the determined change in reflectance of the optical resonator.

Embodiment 23. The optical voltage sensor of any one of embodiments 16-22, further comprising a sensing chip configured to sense a voltage of a subject, and amplify the voltage of the subject to produce the applied voltage applied to the optical resonator.

Embodiment 24. The optical voltage sensor of any one of embodiments 16-23, wherein the sensing chip comprises a complementary metal-oxide semiconductor (CMOS) sensor.

Embodiment 25. The optical voltage sensor of any one of embodiments 16-24, further comprising:
a bottom mirror layer, wherein the bottom mirror layer is positioned on a bottom side of the piezoelectric layer; and
an anti-reflection coating (ARC) layer positioned on a bottom side of the bottom mirror layer.

Embodiment 26. A method of measuring a voltage, the method comprising:
applying a voltage to an optical resonator of a voltage sensor, the optical resonator comprising: (i) a top electrode layer, (ii) a piezoelectric layer, and (iii) a substrate;
illuminating, with a light source, the optical resonator of the voltage sensor with light comprising an incident optical power at an input wavelength, wherein the input wavelength is offset from a resonant wavelength of the optical resonator at a baseline voltage; and
measuring the applied voltage by measuring a transmitted light power transmitted from the illumination through the optical resonator.

Embodiment 27. The method of embodiment 26, wherein the measuring of the applied voltage comprises determining a change in transmittance of the optical resonator caused by the applied voltage.

Embodiment 28. The method of any one of embodiments 26-27, wherein the measuring the applied voltage occurs by:
determining a transmittance of the optical resonator at the applied voltage based on: (i) the incident optical power, and (ii) the measured transmitted light power;
determining a change in transmittance of the optical resonator from: (i) a baseline transmittance of the optical resonator at a baseline voltage to (ii) the determined transmittance of the optical resonator at the applied voltage; and
determining the applied voltage based on the determined change in transmittance of the optical resonator.

Embodiment 29. The method of embodiment 28, wherein the baseline voltage is 0V.

Embodiment 30. The method of any one of embodiments 26-29, wherein the transmitted power is measured with a fiber optic cable coupled to the optical resonator.

Embodiment 31. The method of any one of embodiments 26-30, wherein a capacitive density of the substrate is lower than a capacitive density of the piezoelectric layer.

Embodiment 32. The method of any one of embodiments 26-31, wherein a ratio of the capacitive density of the piezoelectric layer to a capacitive density of the substrate is greater than 4,500 to 1.

Embodiment 33. The method of any one of embodiments 26-32, wherein the light source comprises a light emitting diode (LED).

Embodiment 34. The method of any one of embodiments 26-33, wherein the substrate is transparent to the input wavelength.

Embodiment 35. The method of any one of embodiments 26-34, wherein the substrate comprises quartz.

Embodiment 35A. The method of any one of embodiments 26-35, wherein the input wavelength is a wavelength that is a steepest point of a transmittance curve of the piezoelectric layer.

Embodiment 35B. The method of any one of embodiments 26-35A, wherein the input wavelength is determined according to a full-width-half max (FWHM) property of a transmittance curve of the piezoelectric layer.

Embodiment 36. An optical voltage sensor, comprising:
an optical resonator comprising: (i) a top electrode layer, (ii) a piezoelectric layer, and (iii) a substrate; and
one or more processors configured to:
determine a transmitted light power created by light incident on the optical resonator, the light incident on the optical resonator comprising an incident optical power at an input wavelength, wherein the input wavelength is offset from a resonant wavelength of the optical resonator; and
measure, based on the determined transmitted light power, an applied voltage applied to the optical resonator.

Embodiment 37. The optical voltage sensor of embodiment 36, wherein the one or more processors are configured to measure the applied voltage by:
determining a transmittance of the optical resonator at the applied voltage based on: (i) the incident optical power, and (ii) the measured transmitted light power;
determining a change in transmittance of the optical resonator from: (i) a baseline transmittance of the optical resonator at a baseline voltage to (ii) the determined transmittance of the optical resonator at the applied voltage; and determining the applied voltage based on the determined change in transmittance of the optical resonator.

Embodiment 38. The optical voltage sensor of embodiment 37, wherein the baseline voltage is 0V.

Embodiment 39. The optical voltage sensor of any one of embodiments 36-38, wherein:

the optical voltage sensor further comprises a fiber optic cable coupled to the optical resonator, and configured to receive light transmitted through the optical resonator comprising the transmitted light power.

Embodiment 40. The optical voltage sensor of any one of embodiments 36-39, wherein a capacitive density of the substrate is lower than a capacitive density of the piezoelectric layer.

Embodiment 41. The optical voltage sensor of any one of embodiments 36-40, wherein a ratio of the capacitive density of the piezoelectric layer to a capacitive density of the substrate is greater than 4,500 to 1.

Embodiment 42. The optical voltage sensor of any one of embodiments 36-41, wherein the light source comprises a light emitting diode (LED).

Embodiment 43. The optical voltage sensor of any one of embodiments 36-42, wherein the substrate comprises quartz.

The invention claimed is:

1. A method of measuring a voltage, the method comprising:

applying a voltage to an optical resonator of a voltage sensor, the optical resonator including (i) a top electrode layer, (ii) a piezoelectric layer, and (iii) a substrate;

illuminating, with a light source, the optical resonator of the voltage sensor with light including an incident optical power at an input wavelength, wherein the input wavelength is offset from a resonant wavelength of the optical resonator at a baseline voltage; and measuring the applied voltage by measuring a reflected light power reflected from the illumination by the optical resonator;

wherein the measuring of the applied voltage occurs by determining a change in reflectance of the optical resonator caused by the applied voltage; and wherein the determining the change in reflectance includes determining the change in reflectance based on: (i) the incident optical power, (ii) the measured reflected light power, and (iii) a reflectance of the piezoelectric layer at the baseline voltage.

2. A method of measuring a voltage, the method comprising:

applying a voltage to an optical resonator of a voltage sensor, the optical resonator including: (i) a top electrode layer, (ii) a piezoelectric layer, and (iii) a substrate;

illuminating, with a light source, the optical resonator of the voltage sensor with light including an incident optical power at an input wavelength, wherein the input wavelength is offset from a resonant wavelength of the optical resonator at a baseline voltage; and measuring the applied voltage by measuring a reflected light power reflected from the illumination by the optical resonator;

wherein the measuring the applied voltage occurs by:

determining a reflectance of the optical resonator at the applied voltage based on: (i) the incident optical power, and (ii) the measured reflected light power;

determining a change in reflectance of the optical resonator from: (i) a baseline reflectance of the optical resonator at a baseline voltage to (ii) the determined reflectance of the optical resonator at the applied voltage; and determining the applied voltage based on the determined change in reflectance of the optical resonator.

3. A method of measuring a voltage, the method comprising:

applying a voltage to an optical resonator of a voltage sensor, the optical resonator including: (i) a top electrode layer, (ii) a piezoelectric layer, and (iii) a substrate;

illuminating, with a light source, the optical resonator of the voltage sensor with light including an incident optical power at an input wavelength, wherein the input wavelength is offset from a resonant wavelength of the optical resonator at a baseline voltage; and measuring the applied voltage by measuring a reflected light power reflected from the illumination by the optical resonator;

wherein the measuring the applied voltage occurs by:

determining a reflectance of the optical resonator at the applied voltage based on: (i) the incident optical power, and (ii) the measured reflected light power;

determining a change in reflectance of the optical resonator from: (i) a baseline reflectance of the optical resonator at a baseline voltage to (ii) the determined reflectance of the optical resonator at the applied voltage; and determining the applied voltage based on: (i) the determined change in reflectance of the optical resonator, and (ii) a sensor gain calculated based on:

an amplitude of a resonant dip of a reflectance curve of the piezoelectric layer;

a quality factor of the optical resonator;

a thickness of the optical resonator;

thickness mode piezoelectric strain coefficient of the piezoelectric layer;

a refractive index of the piezoelectric layer; and a Pockels coefficient of the piezoelectric layer.

4. A method of measuring a voltage, the method comprising:

applying a voltage to an optical resonator of a voltage sensor, the optical resonator including: (i) a top electrode layer, (ii) a piezoelectric layer, and (iii) a substrate;

illuminating, with a light source, the optical resonator of the voltage sensor with light including an incident optical power at an input wavelength, wherein the input wavelength is offset from a resonant wavelength of the optical resonator at a baseline voltage; and measuring the applied voltage by measuring a reflected light power reflected from the illumination by the optical resonator;

wherein the input wavelength is a wavelength that is a steepest point of a reflectance curve of the piezoelectric layer.

5. The method of claim 1, wherein the input wavelength is determined according to a full-width-half max (FWHM) property of a reflectance curve of the piezoelectric layer.

6. The method of claim 1, wherein the piezoelectric layer has a thickness mode piezoelectric strain coefficient of greater than 50 pm/V.

7. The method of claim 1, wherein the piezoelectric layer has a Pockels coefficient of greater than 50 pm/V.

8. The method of claim 1, wherein the optical resonator further includes a first mirror on a first side of the piezoelectric layer, and a second mirror on a second side of the piezoelectric layer.

9. The method of claim 8, wherein the first mirror and the second mirror each include alternating layers of silicon dioxide ($SiO_2$) and amorphous silicon (Si).

10. The method of claim 8, wherein the first mirror and the second mirror each include a first layer including a first material with a first refractive index, and a second layer including a second material with a second refractive index, wherein the first refractive index is different than the second refractive index.

11. The method of claim 1, wherein the optical resonator further includes:
- a first plurality of electrodes positioned on a top side of the piezoelectric layer, wherein the first plurality of electrodes is transparent;
- a second plurality of electrodes positioned on a bottom side of the piezoelectric layer;
- a first mirror positioned on the first plurality of electrodes, the first mirror including a first layer with a first refractive index, and a second layer with a second refractive index, wherein the first refractive index of the first mirror is different than the second refractive index of the first mirror; and
- a second mirror positioned on the second plurality of electrodes, the second mirror including a first layer with a first refractive index, and a second layer with a second refractive index, wherein the first refractive index of the second mirror is different than the second refractive index of the second mirror.

12. The method of claim 1, wherein the optical resonator has a diameter of between 15 micrometers and 25 micrometers.

13. The method of claim 1, wherein the piezoelectric layer includes: barium titanate (BTO), potassium sodium niobate (KNN), bismuth ferrite (BFO), or zirconate titanate (PZT).

14. An optical voltage sensor, comprising:
optical resonator includes: (i) a top electrode layer, (ii) a piezoelectric layer, and (iii) a substrate; and
one or more processors configured to:
    determine a reflected light power created by light incident on the optical resonator, the light incident on the optical resonator including an incident optical power at an input wavelength, wherein the input wavelength is offset from a resonant wavelength of the optical resonator; and
    measure, based on the reflected light power reflected from the optical resonator, an applied voltage applied to the optical resonator;
wherein the optical resonator further includes a backside aluminum layer; and
wherein the piezoelectric layer is positioned on a top of the substrate, and the backside aluminum layer is positioned on a bottom of the substrate.

15. The optical voltage sensor of claim 14, wherein:
the top electrode layer includes an indium tin oxide (ITO) film; and
the piezoelectric layer includes aluminum nitride (AlN).

16. An optical voltage sensor, comprising:
optical resonator including: (i) a top electrode layer, (ii) a piezoelectric layer, and (iii) a substrate; and
one or more processors configured to:
    determine a reflected light power created by light incident on the optical resonator, the light incident on the optical resonator including an incident optical power at an input wavelength, wherein the input wavelength is offset from a resonant wavelength of the optical resonator; and
    measure, based on the reflected light power reflected from the optical resonator, an applied voltage applied to the optical resonator;
wherein:
the optical resonator further includes a bond pad layer including titanium and aluminum; and
the bond pad layer is positioned both on a top side of the piezoelectric layer, and a top side of the top electrode layer.

17. An optical voltage sensor, comprising:
optical resonator including: (i) a top electrode layer, (ii) a piezoelectric layer, and (iii) a substrate; and
one or more processors configured to:
    determine a reflected light power created by light incident on the optical resonator, the light incident on the optical resonator including an incident optical power at an input wavelength, wherein the input wavelength is offset from a resonant wavelength of the optical resonator; and
    measure, based on the reflected light power reflected from the optical resonator, an applied voltage applied to the optical resonator;
wherein the top electrode layer includes a mirror layer including a plurality of through-holes connecting a top section of the top electrode layer to a bottom section of the top electrode layer.

18. The optical voltage sensor of claim 17, wherein a material of the top section of the top electrode layer is a same material as a material that fills: (i) the plurality of through-holes; and (ii) the bottom section of the top electrode layer.

19. The optical voltage sensor of claim 18, further including a bottom electrode layer, wherein:
the bottom electrode layer includes a mirror layer including a plurality of through-holes connecting a top section of the bottom electrode layer to a bottom section of the bottom electrode layer; and
a material of the top section of the bottom electrode layer is a same material as a material that fills: (i) the through-holes of the mirror layer of the bottom electrode layer; and (ii) the bottom section of the bottom electrode layer.

20. An optical voltage sensor, comprising:
optical resonator including: (i) a top electrode layer, (ii) a piezoelectric layer, and (iii) a substrate;
one or more processors configured to:
    determine a reflected light power created by light incident on the optical resonator, the light incident on the optical resonator including an incident optical power at an input wavelength, wherein the input wavelength is offset from a resonant wavelength of the optical resonator; and
    measure, based on the reflected light power reflected from the optical resonator, an applied voltage applied to the optical resonator; and
a sensing chip configured to sense a voltage of a subject, and amplify the voltage of the subject to produce the applied voltage applied to the optical resonator.

21. The optical voltage sensor of claim 20, wherein the sensing chip includes a complementary metal-oxide semiconductor (CMOS) sensor.

22. The optical voltage sensor of claim 14, further comprising:
- a bottom mirror layer, wherein the bottom mirror layer is positioned on a bottom side of the piezoelectric layer; and
- an anti-reflection coating (ARC) layer positioned on a bottom side of the bottom mirror layer.

* * * * *